(12) United States Patent
Dalton et al.

(10) Patent No.: US 12,186,488 B2
(45) Date of Patent: Jan. 7, 2025

(54) SELECTIVE ATTACHMENT DEVICE WITH MULTIPLE FLUID SOURCES FOR MAINTAINING POSITIVE FLUID PRESSURE

(71) Applicant: Legacy Innovation Inc., Boise, ID (US)

(72) Inventors: Jeffrey Travis Dalton, Boise, ID (US); Kim Reeves, Boise, ID (US); William Mack Buchanan, Boise, ID (US); Lance Gordon Matheson, Boise, ID (US); Jordan Francis Clifford, Boise, ID (US); Travis Andrew Dean, Boise, ID (US)

(73) Assignee: Legacy Innovation Inc., Boise, ID (US)

( * ) Notice: Subject to any disclaimer, the term of this patent is extended or adjusted under 35 U.S.C. 154(b) by 0 days.

(21) Appl. No.: 18/071,551

(22) Filed: Nov. 29, 2022

(65) Prior Publication Data

US 2023/0123127 A1    Apr. 20, 2023

Related U.S. Application Data

(63) Continuation-in-part of application No. PCT/US2021/032819, filed on May 17, 2021, which
(Continued)

(51) Int. Cl.
*G05D 16/04* (2006.01)
*A61M 16/00* (2006.01)
(Continued)

(52) U.S. Cl.
CPC ...... *A61M 16/127* (2014.02); *A61M 16/0072* (2013.01); *A61M 16/14* (2013.01);
(Continued)

(58) Field of Classification Search
CPC .......................... G05D 16/04; G05D 16/0672
See application file for complete search history.

(56) References Cited

U.S. PATENT DOCUMENTS 3,664,372 A * 5/1972 Marshall ............... F16K 5/0492
251/312
4,506,665 A * 3/1985 Andrews ........... A61M 16/0833
128/203.29
(Continued)

*Primary Examiner* — Paul J Gray
(74) *Attorney, Agent, or Firm* — Recipon Consulting, LLC; Shirley A. Recipon

(57) ABSTRACT

There is provided an attachment device for maintaining positive fluid pressure, the attachment device comprising a body having a fluid outlet port and at least two positive pressure fluid inlet ports; wherein each of the at least two positive pressure fluid inlet ports is connectable to a respective fluid source; wherein each of the at least two positive pressure fluid inlet ports is in fluid communication with the fluid outlet port; wherein each of the at least two positive pressure fluid inlet ports comprises an attachment device mechanism for selectively starting and stopping a flow of fluid from the respective fluid source to the fluid outlet port, and wherein the attachment device mechanism comprises a valve moveable between an open valve position and a closed valve position. An attachment device, connector, and method of using an apparatus suitable for a ventilator is also disclosed.

20 Claims, 69 Drawing Sheets

Related U.S. Application Data is a continuation of application No. 16/888,564, filed on May 29, 2020, now Pat. No. 11,007,342.

(60) Provisional application No. 63/378,358, filed on Oct. 4, 2022.

(51) Int. Cl.
*A61M 16/12* (2006.01)
*A61M 16/14* (2006.01)
*A61M 16/20* (2006.01)
*G05D 16/06* (2006.01)

(52) U.S. Cl.
CPC ........... *A61M 16/201* (2014.02); *G05D 16/04* (2013.01); *A61M 2202/0208* (2013.01); *G05D 16/0672* (2013.01)

(56) References Cited

U.S. PATENT DOCUMENTS

| | | | | |
|---|---|---|---|---|
| 5,439,452 | A * | 8/1995 | McCarty | A61M 39/223 137/625.22 |
| 6,305,400 | B1 * | 10/2001 | Simo | A61M 16/104 137/382 |
| 2007/0225647 | A1 * | 9/2007 | Luther | A61M 25/0075 604/167.03 |
| 2009/0065076 | A1 * | 3/2009 | Rossall | F16L 41/03 137/602 |
| 2009/0071548 | A1 * | 3/2009 | Patterson | G05D 16/103 137/497 |
| 2011/0114862 | A1 * | 5/2011 | Zimmermann | F16L 37/44 251/149.6 |
| 2018/0296175 | A1 * | 10/2018 | Carmody | F16K 31/1268 |

* cited by examiner

SELECTIVE ATTACHMENT DEVICE WITH MULTIPLE FLUID SOURCES FOR MAINTAINING POSITIVE FLUID PRESSURE

CROSS REFERENCE TO RELATED APPLICATIONS

This application is a Continuation-In-Part bypass application of PCT application No. PCT/US2021/032819, filed May 17, 2021, which claims the benefit of priority to U.S. Utility application Ser. No. 16/888,564, filed May 29, 2020, entitled "Fluid Mixing Apparatus Such as a Ventilator", and this application also claims the benefit of priority to U.S. Provisional application No. 63/378,358, filed Oct. 4, 2022, entitled "Selective Attachment Device with Multiple Fluid Sources for Maintaining Positive Fluid Pressure", each of which are hereby incorporated by reference in their entirety.

FIELD OF THE INVENTION

The invention generally relates to a fluid mixing apparatus, and more specifically to fluid mixing apparatus such as ventilators usable for human patients suffering from respiratory symptoms of a disease such as COVID-19 or from chronic respiratory ailments, and methods of utilizing such ventilators.

BACKGROUND

As of the earliest filing date of this document, a pandemic of the COVID-19 virus is sweeping Earth. COVID-19 includes a number of symptoms, but is primarily a respiratory disease. The majority of people exposed to the COVID-19 virus have mild symptoms, if any, and return to full health quickly. However, a significant minority of people react extremely badly to exposure to the COVID-19 virus. For those people, their lungs can become infected and inflamed, filling up the alveoli with pus or fluid, becoming clogged, interfering with oxygen transfer to the capillaries. The sickest patients, with the worst response to the COVID-19 virus, may suffer from Acute Respiratory Distress Syndrome (ARDS). Patients with ARDS have lungs that have been badly damaged by the COVID-19 virus, and their alveoli become filled with fluid. Naturally-occurring surfactant in the lungs, which helps the alveoli inflate and deflate, breaks down, making the lungs stiffer. In addition, inflammation from ARDS increases the gap between the alveoli inner surface and the adjacent capillaries, reducing oxygen transfer to the capillaries still further. Patients suffering from such extreme symptoms from COVID-19 infection or other causes must be intubated, and connected to a ventilator, in order to push oxygen into their lungs and improve oxygen transfer to the blood.

As much as intubation and ventilation may be the last line of defense between life and death for patients suffering from severe symptoms of COVID-19 infection, and other patients with ARDS, ventilation is invasive and expensive; another step between no help with breathing at all and full intubated ventilation would be beneficial. Additionally, current ventilators can exhaust droplets exhaled by the patient into the patient's surroundings-typically a hospital room or an intensive care unit. These droplets typically carry the COVID-19 virus from infected patients, placing healthcare workers and other patients at risk.

Further, current ventilators rely on a continuous supply of compressed oxygen in order to function properly; operation of such current ventilators requires the oxygen supply to be continuously flowing. This continuous flow wastes oxygen and increases costs, and makes current ventilators unsuitable for remote locations, locations in less-developed countries, or other locations that lack access or only have minimal access to plentiful and continuous oxygen supplies. Similarly, existing ventilators rely on electronics to control the ventilator, and on electrical power to power the electronics. This need for electricity also makes current ventilators unsuitable for remote locations, locations in less-developed countries, or other locations that lack access or only have minimal access to continuous electricity.

Accordingly, there is a need for an improved ventilator that is less invasive for the patient and presents less risk of infection for people near the ventilated patient.

Additionally, ventilation used during "interhospital, intrahospital, or prehospital emergency transport", which is known as "transport ventilation", is becoming increasingly difficult due to the high density of patients suffering from the effects of COVID-19 and due to the current devices and techniques used during transport ventilation. For example, currently, transport ventilation in the medical field relies on a medical professional/operator to completely detach a patient from one fluid source (for instance oxygen) to transfer to another fluid source (for example oxygen). This may occur, for example, when a patient is being transferred from an ambulance, while being connected to a temporary oxygen supply during transport, to the hospital, where transfer to a more permanent oxygen supply connection is desired. In such a situation, the continuous delivery from the original oxygen source, upon which a patient is reliant during transfer, is critical in maintaining the volume in the patient's lungs to avoid collapse of the lungs. It is well understood in the medical field that it can take a matter of seconds for lungs to deflate or collapse without a continuous air/oxygen supply, which, due to the pathophysiology of the lungs, can be severely detrimental to a patient-so much so that it can take up to 16 to 20 hours for a patient's lungs to return to normal inflation with support of a ventilator. Therefore, the disruption in fluid flow caused during these critical seconds of transfer from one fluid source to another fluid source when employing conventional devices and techniques can severely impact the health of a patient. It will be appreciated that maintaining a constant fluid flow, or close to constant, without experiencing a significant drop in pressure for example, during transfer from one fluid source to another fluid source is important in many fields (for example, non-medical fields) to enable optimum performance.

Thus, there is a need for a new approach to transport ventilation in the medical field to address, at least in part, the deficiencies associated with conventional transport ventilation devices and methods, and there is a need to provide solutions not hitherto contemplated nor possible with known constructions and techniques. In particular, it is desirable to provide a way of transferring to and/or switching from one fluid source to another fluid source without experiencing a significant disruption of fluid flow. This may involve maintaining the fluid flow and/or the fluid pressure during transfer and/or switching, for example, in both medical and non-medical applications.

SUMMARY

According to some embodiments, a ventilator, which may be mechanical, relies on the natural breathing of the patient to control the flow of air into a respirator. The airflow provided is at a slightly higher pressure than ambient air pressure, and can also be oxygen enriched to aid patients with breathing difficulties. According to some embodiments, rather than relying on electronics to control the flow of air, a simple and robust mechanical valve is used to shut off the flow of compressed air and/or oxygen into the venturi intake. The valve is activated by the slight pressure changes created when the patient is naturally breathing. The valve can be based on a simple diaphragm and flap valve system, bistable diaphragm system, or spring loaded shuttle system.

According to an aspect of the present invention, there is provided a ventilator including a venturi nozzle for flow of a pressure-controlled fluid; an ambient fluid aperture in fluid communication with the venturi nozzle; a fluid port; a pressure force multiplier in fluid communication with the fluid port; and a valve moveable relative to the venturi nozzle between a start flow position and a stop flow position; where the pressure force multiplier is configured such that fluid forced into the fluid port actuates the valve relative to the venturi nozzle; and where the pressure force multiplier is configured such that fluid withdrawn from the fluid port actuates the valve relative to the venturi nozzle.

According to an aspect of the present invention, there is provided a ventilator connectable to the airway of a living patient, comprising: a venturi, comprising a throat; a venturi nozzle; a venturi opening in the venturi nozzle through which pressure-controlled oxygen flows outward, wherein said venturi opening opens to said throat, and wherein said venturi opening and said throat are substantially longitudinally aligned; an ambient air aperture in fluid communication with said venturi nozzle and with ambient air; a fluid port in fluid communication with the airway of the patient; a pressure force multiplier in fluid communication with said fluid port, wherein said pressure force multiplier includes at least one opening defined therethrough; said pressure force multiplier comprising at least one flap movable between an open position and a closed position relative to said at least one opening; and a valve moveable along an axis of movement relative to said venturi opening in said venturi nozzle between a start flow position that causes entrainment of the ambient air by the flow of pressure-controlled oxygen within said throat, and a stop flow position that ceases entrainment of the ambient air by the flow of pressure-controlled oxygen within said throat; wherein said pressure force multiplier is configured wherein exhalation of the patient into said fluid port actuates said valve along said axis of movement relative to said venturi nozzle to close said venturi nozzle; wherein said pressure force multiplier is configured wherein inhalation of the patient through said fluid port actuates said valve along said axis of movement relative to said venturi nozzle; and wherein said axis of movement of said valve is substantially longitudinally aligned with a longitudinal direction of said throat.

It may be that the inhalation of the patient through said fluid port actuates said valve relative to said venturi nozzle to open said venturi nozzle.

It may be that the exhalation of the patient into said fluid port causes said at least one flap to move to said closed position relative to said at least one opening in said pressure force multiplier.

It may be that the inhalation of the patient through said fluid port causes said at least one flap to move to said open position relative to said at least one opening in said pressure force multiplier.

According to another aspect, the present invention contemplates an apparatus suitable for a ventilator, including a venturi nozzle for flow of a pressure-controlled fluid; an ambient fluid aperture in fluid communication with the venturi nozzle; a fluid port; a pressure force multiplier in fluid communication with the fluid port; and a valve moveable relative to the venturi nozzle between a start flow position and a stop flow position; where the pressure force multiplier is configured such that fluid forced into the fluid port actuates the valve relative to the venturi nozzle; and where the pressure force multiplier is configured such that fluid withdrawn from the fluid port actuates the valve relative to the venturi nozzle.

According to another aspect, the present invention contemplates an apparatus suitable for use with a respirator (ventilator), comprising: a venturi, comprising: a throat, a venturi nozzle, and; a venturi opening in the venturi nozzle through which pressure-controlled fluid flows outward, wherein said venturi opening opens to said throat, and wherein said venturi opening and said throat are substantially longitudinally aligned; an ambient fluid aperture in fluid communication with said venturi nozzle and with an ambient fluid; a fluid port; a pressure force multiplier in fluid communication with said fluid port; and a valve moveable along an axis of movement relative to said venturi opening in said venturi nozzle between a start flow position that causes entrainment of the ambient fluid by the flow of pressure-controlled fluid within said throat, and a stop flow position that ceases entrainment of the ambient fluid by the flow of pressure-controlled fluid within said throat; wherein said pressure force multiplier is configured such that fluid forced into said fluid port actuates said valve along said axis of movement relative to said venturi nozzle to close said venturi nozzle; wherein said pressure force multiplier is configured such that fluid withdrawn from said fluid port actuates said valve along said axis of movement relative to said venturi nozzle; wherein said axis of movement of said valve is substantially longitudinally aligned with a longitudinal direction of said throat; and wherein said pressure force multiplier is positioned between said venturi nozzle and said fluid port. Thus, the present invention does not rely on the pressure-controlled fluid to be continuously flowing as is commonly the case with known constructions. Therefore, significant savings, both economic and environmental, can be made due to the present invention actuating the valve to regulate the flow of the pressure-controlled fluid which in effect makes the overall process more efficient. The apparatus may be particularly suitable for remote locations, locations in less-developed countries, or other locations that lack access or only have minimal access to plentiful and continuous fluid supplies.

The pressure force multiplier may be configured such that the (any) fluid forced into the fluid port actuates the valve relative to the venturi nozzle to a stop flow position; and the pressure force multiplier may be configured such that the (any) fluid withdrawn from the fluid port actuates the valve relative to the venturi nozzle to a start flow position.

The pressure force multiplier may be configured such that the (any) fluid forced into the fluid port actuates the valve relative to the venturi nozzle to a start flow position; and the pressure force multiplier may be configured such that the (any) fluid withdrawn from the fluid port actuates the valve relative to the venturi nozzle to a stop flow position. This may be considered a reverse configuration, for instance.

The pressure force multiplier may be configured such that the (any) fluid forced into the fluid port actuates the valve relative to the venturi nozzle to an active flow position between the start flow position and stop flow position; and the pressure force multiplier may be configured such that the (any) fluid withdrawn from the fluid port actuates the valve relative to the venturi nozzle to an active flow position between the start flow position and stop flow position. In such a configuration, both actions of a fluid being forced into the fluid port and a fluid being withdrawn from the fluid port can actuate the valve to an active flow position. This may be considered a point anywhere between the stop flow and start flow positions. Hence, the flow may be completely controlled and/or regulated from the stop flow to start flow and all positions therebetween.

The apparatus may be defined such that a pressure-controlled fluid includes oxygen, an ambient fluid includes ambient air, fluid forced into the fluid port includes air exhaled into an air port, and fluid withdrawn from the fluid port includes air inhaled from an air port.

It may be that the pressure force multiplier is positioned between the venturi nozzle and the fluid port. Such a positioning may provide enhanced actuation of the valve.

The venturi nozzle may be positioned between the pressure force multiplier and the fluid port. The inventors consider such a positioning may also provide enhanced actuation of the valve.

It may be that the venturi nozzle is positioned between the ambient fluid aperture and the fluid port. The inventors found such a positioning may also provide enhanced actuation of the valve.

The apparatus may comprise a pressure regulator for regulating the flow of a pressure-controlled fluid. It will be appreciated that at least one of many different pressure regulators suitable for the purpose of regulating the flow of the pressure-controlled fluid may be included.

More particularly, the apparatus may comprise a pressure regulator (for regulating the flow of the pressure-controlled fluid) comprising a housing formed to include a bore therein; a piston moveably disposed within the bore, wherein the piston includes an annular lip adjacent a first end thereof; a spring disposed within the bore, and comprising a first end and a second end; an adjustment cap moveably disposed in the bore, where the adjustment cap is formed to include a plurality of key slots formed therein; wherein: the first end of the spring is in physical contact with the annular lip; and the second end of the spring is in physical contact with the adjustment cap wherein: rotating the adjustment cap in a first direction causes the adjustment cap to compress the first spring; rotating the adjustment cap in a second and opposite direction causes the adjustment cap to decompress the spring; rotating the adjustment cap in the first direction increases the output pressure of the pressure regulator; rotating the adjustment cap in the second direction decreases the output pressure of the pressure regulator; the bore is defined by a cylindrical wall; the cylindrical wall is formed to include a first threading therein; the adjustment cap is formed to include a second threading formed on a periphery thereof; and the second threading is configured to mesh with the first threading. Such a regulator may be particularly effective at regulating the flow of the pressure-controlled fluid. The inventors have found such a pressure regulator to have particularly good synergy with the apparatus defined herein. This synergy makes such a pressure regulator a specific selection generating enhanced performance of the apparatus.

The pressure force multiplier may comprise a diaphragm. The diaphragm may be saucer-shaped to enhance its function.

It may be that the pressure force multiplier is bi-stable. This may be in an inhalation configuration and an exhalation configuration. In this way, the pressure force multiplier expresses two stable states which is particularly beneficial in at least some embodiments of the present invention.

The pressure force multiplier may be biased toward the stop flow position. In some embodiments, it may be preferred that the pressure force multiplier be biased toward the stop flow position, and such an arrangement makes this possible.

The pressure force multiplier may be biased toward the start flow position. Conversely, or additionally, in some embodiments, it may be preferred that the pressure force multiplier be biased toward the start flow position, and such an arrangement makes this possible.

The pressure force multiplier may include at least one flap.

It may be that the apparatus is solely mechanical. According to some embodiments, the apparatus being solely mechanical provides the benefit of simplicity of manufacture and operation.

The apparatus may be configured such that in the start flow position or an active flow position a mixture of pressure-controlled fluid and ambient fluid is allowed to flow to the fluid port. For example, it may be that the ambient fluid, such as ambient air, becomes entrained with the flow of the pressure-controlled fluid, such as oxygen, driving flow and movement towards the fluid port.

The flow of the mixture may be modulated in real-time. The apparatus may, therefore, control, change, and/or regulate the flow of the fluid mixture in an alternative or additional way to the regulation of the flow of the pressure-controlled fluid alone.

It may be that the valve includes a flange that is connected to the pressure force multiplier.

The valve may include a stem with a tapered end, where the tapered end enters a venturi opening in the venturi nozzle in the stop position to substantially close the venturi opening. Such an arrangement may be particularly effective in operation of the valve in relation to the features of the apparatus defined herein, It may be that the stem is connected to the pressure force multiplier. Such a configuration may make the stem and force multiplier more robust during operation.

The valve may comprise a switch. This may be particularly effective when a binary system is desired, or binary states are desired.

It may be that the valve includes a flap valve.

The valve may comprise a spring-loaded shuttle system.

The valve may be slidable.

The valve may be solely mechanical.

It may be that the ambient fluid aperture includes a fluid exhaust. The ambient fluid aperture may, therefore, have the dual function of allowing ingress and egress of fluid. Exhaustion of fluid from the apparatus may reduce contamination by used fluids within the apparatus, and may simplify the apparatus by eliminating the need to store used fluid that is not exhausted.

The valve may be configured to be actuated relative to the venturi nozzle while simultaneously opening the fluid exhaust. Such a dual functionality may improve the operational efficiency of the apparatus.

The apparatus may further comprise at least one filter detachably connected to the ambient fluid aperture. The filter may operate to filter incoming and/or outgoing fluid to/from the apparatus. Filtration of both incoming and outgoing fluid with a single filter may improve the operational efficiency of the apparatus.

The at least one filter may comprise pores of about 3 μm. This pore size is particularly effective in removing contaminants such as viruses and bacteria from fluid such as air, for example.

The apparatus may further comprise a respirator or similar apparatus that provides for fluid communication between the ventilator and the airway of a patient. The inventors have discovered that the respirator used in combination with the apparatus or forming part of the apparatus may be particularly effective in treating respiratory conditions such as COVID-19.

The respirator may be in fluid communication with the fluid port. The fluid port may be connected directly or indirectly to the respirator, for instance.

The fluid described herein above may be a liquid. In various applications, liquid may pass through the apparatus. It will be appreciated that liquid such as medicine may also be administered using the apparatus. For instance, the apparatus may thus function as an improved nebulizer or vaporizer that can be used to administer medication in the form of a liquid mist that can be inhaled into the lungs by a patient suffering from a respiratory disease or condition. It will be appreciated, however, that any suitable liquid may be utilized with the apparatus.

The apparatus may be injection molded. The apparatus may thus be quickly reproduced in a cost-effective manner.

It may be that the apparatus is fabricated by additive manufacturing, such as a 3D printing process. The apparatus may, therefore, be reproduced accurately and in a cost-effective manner, which makes it particularly attractive in less-developed countries. The apparatus may be injection molded in such a way as to include a 3D Printed Part, or parts, into the overall apparatus. The apparatus may thus be quickly reproduced in a cost-effective manner.

The apparatus may be configured to be mobile.

The apparatus may be configured to be re-usable. Since the apparatus may be effectively be cleaned, it may be suitable for re-use. This is particularly beneficial in less-developed countries where availability of new apparatus are not readily available. The apparatus may be placed in a bag with a capsule containing a measured amount of isopropyl alcohol. The bag may then be closed, the capsule squeezed to release the isopropyl alcohol, shaken, then left in the sun. After a certain amount of time, the bag may be opened, the apparatus removed, trayed, and used by another patient.

The apparatus described herein may be for use in controlling the flow of air and/or oxygen into a respirator (ventilator).

The apparatus described herein may be for use in controlling the flow of scrubbed air and/or oxygen into a respirator (ventilator).

The apparatus described herein may be for use in treating a respiratory condition.

The apparatus described herein may be for use in treating COVID-19.

In another aspect, the present invention envisages a method of using an apparatus suitable for a ventilator, the method including providing a source of pressure-controlled fluid; providing an apparatus suitable for a respirator, including: a venturi nozzle for receiving a flow of the pressure-controlled fluid; an ambient fluid aperture in fluid communication with the venturi nozzle; a fluid port; a pressure force multiplier in fluid communication with the fluid port; and a valve moveable relative to the venturi nozzle between a start flow position, in which the pressure-controlled fluid mixes with the ambient fluid, and a stop flow position; actuating the valve relative to the venturi nozzle in response to fluid forced into the fluid port; and actuating the valve relative to the venturi nozzle in response to fluid withdrawn from the fluid port.

In another aspect, the present invention envisages a method of using an apparatus suitable for a ventilator, the method comprising: providing a pressure-controlled oxygen source; providing an apparatus suitable for a ventilator, comprising: a venturi, comprising a throat; a venturi nozzle; a venturi opening in said venturi nozzle through which pressure-controlled oxygen flows outward, wherein said venturi opening opens to said throat, and wherein said venturi opening and said throat are substantially longitudinally aligned; an ambient air aperture in fluid communication with said venturi nozzle and with ambient air; a fluid port; a pressure force multiplier in fluid communication with said fluid port, wherein said pressure force multiplier includes at least one opening defined therethrough; said pressure force multiplier comprising at least one flap movable between an open position and a closed position relative to said at least one opening; and a valve moveable along an axis of movement relative to said venturi opening in said venturi nozzle between a start flow position that causes entrainment of the ambient air by the flow of pressure-controlled oxygen within said throat, and a stop flow position that ceases entrainment of the ambient air by the flow of pressure-controlled oxygen within said throat; placing said fluid port in fluid communication with an airway of the patient; in response to exhalation by the patient through said fluid port, causing said at least one flap to move to said closed position relative to said at least one opening, and actuating said valve along said axis of movement relative to said venturi nozzle to close said venturi nozzle; and in response to inhalation by the patient through said fluid port, causing said at least one flap to move to said open position relative to said at least one opening, and actuating said valve along said axis of movement relative to said venturi nozzle; and wherein said axis of movement of the valve is substantially longitudinally aligned with the longitudinal direction of the throat.

The apparatus in such a method may be solely mechanical.

It may be that at least a portion of said valve is movable, along said axis of movement, within said throat.

The method may further comprise adjusting the pressure of the pressure-controlled fluid.

It may be that the method includes that the pressure-controlled fluid is pressure-controlled oxygen, and where the fluid is air, the method including: connecting the apparatus to a respirator or similar apparatus (ventilator); placing the ventilator in gaseous communication with the patient and with the source of pressure-controlled oxygen; in response to inhalation by the patient, starting oxygen flow into the ventilator, mixing the oxygen with ambient air to generate enriched air, and delivering the enriched air to the patient; in response to exhalation by the patient, stopping oxygen flow into the ventilator, and exhausting exhalation air from the ventilator.

The enriched air may have an FiO2 of at least 26%.

It may be that the method includes that the pressure-controlled fluid is pressure-controlled filtered air, and where the fluid is air, the method including: connecting the apparatus to a respirator or similar apparatus (ventilator); placing the ventilator in gaseous communication with the patient and with the source of pressure-controlled filtered air; in response to inhalation by the patient, starting oxygen flow into the ventilator, mixing the pressure-controlled filtered air with ambient air to generate scrubbed air, and delivering the scrubbed air to the patient; in response to exhalation by the patient, stopping oxygen flow into the ventilator, and exhausting exhalation air from the ventilator.

The scrubbed air may have an FiO2 of at least 26%.

The method may further include walking and/or running while utilizing the apparatus and a respirator or similar apparatus (ventilator). This may involve use of the apparatus while the user is exercising, for instance.

The method may further include initiating use of the apparatus and respirator or similar apparatus (ventilator) to treat allergies.

The method may further include initiating use of the apparatus and respirator or similar apparatus (ventilator) to treat ARDS.

The method may further include initiating use of the apparatus and respirator or similar apparatus (ventilator) to treat sleep apnea.

The method may further include initiating use of the apparatus and respirator or similar apparatus (ventilator) to treat COPD.

The method may further include initiating use of the apparatus and respirator or similar apparatus (ventilator) to treat infection by the COVID-19 virus.

The method may further include filtering the ambient air.

The method may further include filtering exhaled breath from the patient.

In another aspect, the present invention encompasses a pressure force multiplier including a sealed end and an open end, where the sealed end is in fluid communication with a valve to define a fixed volume between the sealed end and the valve, where the pressure force multiplier is configured such that a change in pressure in the open end causes a change in pressure in the sealed end which actuates the valve. Such a force multiplier may be particularly effective for use with the apparatus defined herein. However, this pressure force multiplier is considered inventive in its own right.

The pressure force multiplier may be configured such that a negative pressure in the open end causes a reduction in pressure in the sealed end which actuates the valve.

The pressure force multiplier may be configured such that a positive pressure in the open end causes an increase in pressure in the sealed end which actuates the valve.

It may be that the actuation of the valve activates a humidifier.

The actuation of the valve may generate a change in a visual indicator. The visual indicator may be a change in color, for instance.

The change in visual indicator may represent a change of pressure in the open end.

It may be that the change of pressure in the open end is caused by inhalation and/or exhalation of a patient. The pressure force multiplier is, thus, adaptable for many different applications, which makes it a particularly useful accessory in many different fields of operation.

In an aspect of the present invention, there is provided an attachment device for maintaining positive fluid pressure, the attachment device comprising a body having a fluid outlet port and at least two positive pressure fluid inlet ports; wherein each of the at least two positive pressure fluid inlet ports is connectable to a respective fluid source; wherein each of the at least two positive pressure fluid inlet ports is in fluid communication with the fluid outlet port; wherein each of the at least two positive pressure fluid inlet ports comprises an attachment device mechanism for selectively starting and stopping a flow of fluid from the respective fluid source to the fluid outlet port, and wherein the attachment device mechanism comprises a valve moveable between an open valve position and a closed valve position.

An attachment device formed according to the present invention enables transfer from one fluid source to another fluid source without experiencing a significant disruption of fluid flow. The transfer may thus be a smooth transfer. The transfer may thus be a smooth transition. One fluid source can thus be switched with another fluid source without experiencing a significant disruption of fluid flow or drop in fluid pressure, for example. The attachment device enables transfer and/or switching from one fluid source to another fluid source without experiencing a significant interruption of fluid flow. In this way, the fluid flow and/or fluid pressure can be maintained during such a transfer/switch/transition. The attachment device enables the transfer/switch/transition of one fluid to another fluid to be gradual to minimize any decline in performance. This can avoid any sharp decline in fluid flow, fluid pressure, and/or overall apparatus performance. The inclusion of a valve moveable between an open valve position and a closed valve position in the attachment device mechanism improves precision of the device so that positive fluid pressure can be maintained more accurately. For example, the valve provides a superior mechanism by which the fluid from one fluid source can be transferred/switched to another fluid source. The speed and efficiency by which one fluid source can be transferred/switched to another fluid source is important potentially in saving the life of a patient, for instance. In this way, attachment device provides a simple and robust design for transferring/switching one fluid source to another fluid source without experiencing a drop in fluid pressure and/or fluid flow.

The attachment device has particular utility in the medical field of transport ventilation. For instance, the attachment device provides a way of transferring to and/or switching from one fluid source (such as oxygen/air) to another fluid source (such as oxygen/air) without experiencing a significant disruption of fluid flow. This can involve maintaining the fluid flow and/or the fluid pressure during transfer and/or switching. Thus, rather than a medical professional/operator completely detaching a patient from one fluid source (for instance oxygen) to transfer to another fluid source (for example oxygen) during transport ventilation when the patient could experience a decrease/lack in oxygen during such transfer, the attachment device enables a continuous delivery of oxygen to the patient—during those critical seconds of transfer from one oxygen source (in ambulance for example) to another oxygen source (in hospital for example). The attachment device, thus, facilitates in maintaining the volume of the patient's lungs and, in doing so, avoids collapsing of the lungs which could cause potential further injury and harm to the patient. The attachment device can be used in relation to a patient's Positive end-expiratory pressure (PEEP) and Functional residual capacity (FRC). PEEP is the positive pressure that will remain in the airways at the end of the respiratory cycle (end of exhalation) that is greater than the atmospheric pressure in mechanically ventilated patients. In patients receiving mechanical ventilation, the use of PEEP mainly has been reserved to recruit or stabilize lung units and improve oxygenation in patients who have hypoxemic respiratory failure. This helps the respiratory muscles to decrease the work of breathing and the amount of infiltrated-atelectatic tissues. The beneficial effects of the use of PEEP include: the improvement of oxygenation, recruitment of lung units, and improvement of compliance. Other effects can be adverse, like decreasing cardiac output, increased risk of barotrauma, and the interference with assessment of hemodynamic pressures, for instance. FRC is the volume of air present in the lungs at the end of passive expiration. At FRC, the opposing elastic recoil forces of the lungs and chest wall are in equilibrium and there is no exertion by the diaphragm or other respiratory muscles.

The attachment device addresses the deficiencies of known constructions and methods employed in transport ventilation, for example, by substantially eliminating those critical seconds where a patient could be starved of oxygen. The attachment device involves multiple fluid inlet ports. This is at least two fluid inlet ports, but it will be understood it can be many more fluid inlet ports (for example, three, four, five, and so forth) according to the needs of the application and field. The fluid inlet ports can be in fluid communication with one another as part of the handoff of one fluid source to the next. Avoiding the disruption of air/oxygen flow is a significant improvement over current respiratory therapy approaches because it substantially eliminates the harmful side effects that arise as a result of oxygen flow disruption during traditional transport ventilation methods. For example, the at least two fluid inlet ports of the attachment device allow at least two fluid lines to be concurrently connected to a patient's breathing respirator or ventilator (including a breathing mask) before one of the fluid lines is ultimately disconnected thereby completing the transfer from one fluid line to the other fluid line without a substantial reduction of fluid flow and performance during the transfer/transition/switch. This is also enabled by each fluid inlet port comprising an attachment device mechanism for selectively starting and stopping the flow of fluid from the respective fluid source to the fluid outlet port of the attachment device, such that before stopping the fluid flow from and disconnecting a first fluid line from a first fluid inlet port by way of the attachment device mechanism in that first fluid inlet port, for example, the operator can start fluid flow from a second fluid line into the attachment device by way of the attachment device mechanism in that second other fluid inlet port to avoid an interruption in fluid flow out of the attachment device via the fluid outlet port.

It will be appreciated that maintaining a constant fluid flow, or close to constant, without experiencing a significant drop in pressure for example, during transfer from one fluid source to another fluid source is important in many fields (for example, non-medical fields) to enable optimum performance.

It may be that the at least two positive pressure fluid inlet ports comprise a first positive pressure fluid inlet port having a first attachment device mechanism, and a second positive pressure fluid inlet port having a second attachment device mechanism, wherein the first attachment device mechanism actuates the flow of fluid from a first fluid source to the fluid outlet port, and the second attachment device mechanism actuates the flow of fluid from a second fluid source to the fluid outlet port, and wherein the ratio of the flow of fluid from the first fluid source to the fluid outlet port and the flow of fluid from the second fluid source to the fluid outlet port ranges from 100%:0%; to 0%/100%. For instance, the ratio of the flow of fluid from the first fluid source to the fluid outlet port and the flow of fluid from the second fluid source to the fluid outlet port may be at least one selected from: 90%:10%, 80%:20%, the flow of fluid from the first fluid source can be transferred immediately to the fluid from the second fluid source. For example, first oxygen supply from a mobile cannister being received by a patient wearing a ventilator can be transferred immediately to a static second oxygen supply in a hospital, for instance, without disrupting the flow/pressure of oxygen being received by the patient by use of the attachment device formed according to the present invention. In this way, the supply of fluid would constitute 100%:0% when the attachment device is providing the first oxygen supply to the patient (100% of first oxygen supply and 0% of second oxygen supply), and would constitute 0%/100% when the attachment device is providing the second oxygen supply to the patient (0% of first oxygen supply and 100% of second oxygen supply). It may be that a gradual transfer/switch of fluid is desired and in this way the attachment device may be configured such that the ratio of the flow of fluid from the first fluid source to the fluid outlet port and the flow of fluid from the second fluid source to the fluid outlet port may be at least one selected from: 90%:10%, 80%:20%, 70%:30%, 60%:40%, 50%:50%, 40%:60%, 30%:70%, 20:80%, and 10%:90%. The transition of transferring fluid from a first fluid source to fluid from a second fluid source in this manner involves the attachment providing the first fluid and second fluid concurrently to the patient via the outlet port. For example, the supply of fluid would constitute 90%:10% when the attachment device is providing a first oxygen supply to the patient (90% of first oxygen supply and 10% of second oxygen supply), and would constitute 10%/90% when the attachment device is providing the second oxygen supply to the patient (10% of first oxygen supply and 90% of second oxygen supply). The transition in this manner may offer superior control and accuracy to the operator when using the attachment device to transfer fluid from one fluid source to fluid of another fluid source. This may be particularly important, for instance, when a first fluid is different in composition to that of a second fluid source and thus a gradient transition in this manner may assist in providing a mixture of the first and second fluids before transferring completely to the second fluid, which may assist a patient with accepting the second fluid more easily rather than an immediate transition to the second fluid, for example.

The valve may comprise a fluid access port.

The valve may comprise an obstructor.

The obstructor and the fluid access port may be rotatably engaged.

The valve may be moveable between the open valve position and the closed valve position by rotation of the obstructor relative to the fluid access port.

The valve may be moveable between the open valve position and the closed valve position by a rotation of approximately 90 degrees of the obstructor relative to the fluid access port.

The obstructor may comprise a rotatable ball having a fluid passage therethrough.

The fluid passage may be L-shaped.

The obstructor may comprise a rotatable handle.

The obstructor and the fluid access port may be linearly engaged.

The valve may be moveable between the open valve position and the closed valve position by a linear movement of the obstructor relative to the fluid access port.

The obstructor may comprise a hollow tube having at least one fluid passage therethrough.

The obstructor may comprise a hollow tube having a first fluid passage and second fluid passage separated by a partition.

The first fluid passage may be alignable with the fluid access port towards or at the open valve position by a linear movement of the obstructor relative to the fluid access port.

The second fluid passage may be alignable with the fluid access port towards or at the open valve position by a linear movement of the obstructor relative to the fluid access port.

The attachment device may comprise an obstructor holder connected to the body, and said obstructor holder may comprise the fluid access port.

The obstructor holder may be slidably engaged with the obstructor.

The obstructor holder may comprise at least two anti-rotation internal protrusions.

The obstructor may comprise at least two anti-rotation external recesses.

The attachment device may comprise a bronchoscope port in fluid communication with the fluid outlet port.

The attachment device may comprise a suction catheter port in fluid communication with the fluid outlet port.

The bronchoscope port may be in fluid communication with the suction catheter port.

In this patent specification, the fluid inlet ports may be positive pressure fluid inlet ports.

The fluid outlet port may be connectable to an endotracheal tube. It may be that the endotracheal tube is inserted into the airway of a patient. Thus, the attachment device of the present invention may be connected to the endotracheal tube in-situ, for example. The patient may be an animal or a human, for instance. Hence, a veterinary practitioner may also employ the attachment device.

It may be that at least one of the at least two positive pressure fluid inlet ports is connectable to a ventilator or ventilator tube.

Each fluid inlet port may comprise an arm extending from the body. The arm may be elongate and/or cylindrical in shape. The shape of the fluid inlet port, being in the form of an arm for instance, may lend itself to avoid overcrowding of the body so that multiple fluid inlet ports can be included on the body. This may aid an operator or medical professional, for example, in identifying the fluid inlet ports and matching them with the appropriate fluid source, thereby reducing errors and improving safety of the patient. This is particularly the case during transport ventilation when time is of the essence is saving a patient's life, such that having at least one fluid inlet port in the form of an arm enables the medical professional to easily and quickly connect the oxygen line to the attachment device by gripping the arm, for example. Of course, it will be appreciated that the at least two fluid inlet ports may not be in the form of arms.

The arm may comprise a groove about its periphery. The groove may facilitate a connector (having a fluid line attached thereto) to engage and/or positively lock with the attachment device. It will be understood that groove may be on the at least two fluid inlet ports, regardless of their shape-even when they are not in the form of an arm for instance.

It may be that the attachment device mechanism comprises a medical valve having a valve stem and a valve seat, wherein the valve seat seals a valve orifice in a closed valve position, and the valve seat unseals the valve orifice in an open valve position. valve stem and a valve seat provides a secure and reliable manner in which to seal and unseal a valve orifice to optimize performance of the attachment device.

The medical valve may be moveable by a mechanical force or a magnetic force. The mechanical force may include pushing or pulling by application of an operator on a component of the attachment device which in turn actuates the medical valve, for example. The magnetic force can be provided by a magnet, and this may be a magnetic attraction or magnetic repulsion, dependent on the arrangement of the mechanism.

The attachment device mechanism may comprise a ball proximal the body, wherein the ball may be moveable between a fluid start flow position and fluid stop flow position by mechanically or magnetically moving the ball towards the interior of the body. It may be that the ball in such an arrangement is inside or partially inside the body. The ball may be mechanically moved by another component of the attachment device/mechanism or may be magnetically moved. When the ball moves inwardly towards the interior of the body, this may open the valve thereby allowing passage of the respective fluid to flow from the fluid source to the attachment device via the fluid inlet port and exit via the fluid outlet port.

The attachment device mechanism may comprise a spring for biasing the ball to the stop flow position. A spring is a reliable, robust, efficient and cost-effective way to hold the ball in the stop flow position. This may be when the attachment device is in a resting or idle state, for example. Biasing the ball to the closed valve position may minimize any fluid from inadvertently and undesirably escaping from the attachment device during times when it is not intended for fluid to leave/egress from the attachment device.

The attachment device mechanism may comprise a domed-cylinder proximal the body, wherein the domed-cylinder may be moveable between a fluid start flow and fluid stop flow position by mechanically or magnetically moving the domed-cylinder towards the interior of the body. The dome-cylinder shape is desirable because the walls of the cylinder enable precise linear movement between the fluid start flow and fluid stop flow positions.

The attachment device mechanism may comprise a spring for biasing the domed-cylinder to the stop flow position. A spring is a reliable, robust, efficient and cost-effective way to hold the domed-cylinder in the stop flow position. This may be when the attachment device is in a resting or idle state, for example. Biasing the domed-cylinder to the closed valve position may minimize any fluid from inadvertently and undesirably escaping from the attachment device during times when it is not intended for fluid to leave/egress from the attachment device.

The body may comprise internal threading at the fluid outlet port that is connectable to a pressure regulator having external threading. Threading provides a fast and reliable method of connection, which is particularly important during medical emergencies where time is of the essence, and to avoid confusion or delay during connection could save a patient's life.

The body may comprise external threading at the fluid outlet port that is connectable to a pressure regulator having internal threading. Threading provides a fast and reliable method of connection, which is particularly important during medical emergencies where time is of the essence, and to avoid confusion or delay during connection could save a patient's life.

The body may be connectable to a pressure regulator by a push-fit mechanism. A push-fit mechanism provides a fast and reliable method of connection, which is particularly important during medical emergencies where time is of the essence, and to avoid confusion or delay during connection could save a patient's life.

At least one of the fluid inlet ports may be detachably attached to the body. Any of the fluid ports may thus be replaced with different sizes to match the needs of a specific size/shape of a fluid source when needed, for example, which is particularly desirable. The fluid inlet port being detachably attached to the body allows the attachment device to be modular such that any part can be easily replaced with a corresponding part if damaged, for instance.

It may be that the respective fluid source is a pressure-controlled oxygen source.

It may be that the respective fluid source is a ventilator.

The attachment device may comprise a bleeder valve.

The bleeder valve may comprise a fluid pressure indicator. The bleeder valve and fluid pressure indicator aid an operator in ensuring that the correct/minimum fluid pressure/flow is present before disengaging a fluid source from a fluid inlet port, thereby maintaining the fluid pressure/flow of the fluid entering and exiting the attachment device via the fluid inlet ports and fluid outlet port, respectively.

The attachment device defined herein may be for use in a medical application.

The attachment device defined herein may be for use in at least one of spooling up a turbocharger, changing cam timing in an engine, operating as an injector or a valve, generating downforce in a car chassis, dispersion of carbon dioxide, controlling humidity by atomizing water, and nutrient distribution.

In another aspect, the present invention contemplates a connector for connecting a fluid source and an attachment device, the connector being attachable to a fluid source and an attachment device, and the connector comprising a housing and a connector mechanism for selectively starting and stopping the flow of fluid from the fluid source to the attachment device.

A connector formed according to the present invention enables transfer from one fluid source to another fluid source without experiencing a significant disruption of fluid flow. The transfer may thus be a smooth transfer. The transfer may thus be a smooth transition. One fluid source can thus be switched with another fluid source without experiencing a significant disruption of fluid flow or drop in fluid pressure, for example. The connector enables transfer and/or switching from one fluid source to another fluid source without experiencing a significant interruption of fluid flow. In this way, the fluid flow and/or fluid pressure can be maintained during such a transfer/switch/transition. The connector enables the transfer/switch/transition of one fluid to another fluid to be gradual to minimize any decline in performance. This can avoid any sharp decline in fluid flow, fluid pressure, and/or overall apparatus performance.

The connector has particular utility in the medical field of transport ventilation. For instance, the connector provides a way of transferring to and/or switching from one fluid source (such as oxygen/air) to another fluid source (such as oxygen/air) without experiencing a significant disruption of fluid flow. This can involve maintaining the fluid flow and/or the fluid pressure during transfer and/or switching. Thus, rather than a medical professional/operator completely detaching a patient from one fluid source (for instance oxygen) to transfer to another fluid source (for example oxygen) during transport ventilation when the patient could experience a decrease/lack in oxygen during such transfer, the connector enables a continuous delivery of oxygen to the patient—during those critical seconds of transfer from one oxygen source (in ambulance for example) to another oxygen source (in hospital for example). The connector, thus, facilitates in maintaining the volume of the patient's lungs and, in doing so, avoids collapsing of the lungs which could cause potential further injury and harm to the patient.

The connector addresses the deficiencies of known constructions and methods employed in transport ventilation, for example, by substantially eliminating those critical seconds where a patient could be starved of oxygen. A connector can be used for each of the multiple fluid inlet ports of an attachment device, for example. Avoiding the disruption of air/oxygen flow is a significant improvement over current respiratory therapy approaches because it substantially eliminates the harmful side effects that arise as a result of oxygen flow disruption during traditional transport ventilation methods. For example, at least two connectors can be connected to at least two fluid inlet ports of the attachment device thereby allowing at least two fluid lines to be concurrently connected to a patient's breathing respirator or ventilator (including a breathing mask) before one of the fluid lines is ultimately disconnected thereby completing the transfer from one fluid line to the other fluid line without a substantial reduction of fluid flow and performance during the transfer/transition/switch. This is also enabled by the connector mechanism for selectively starting and stopping the flow of fluid from the fluid source to the attachment device, such that before stopping the fluid flow from and disconnecting a first fluid line by way of a first connector mechanism, for example, the operator can start fluid flow from a second fluid line into the attachment device by way of a second connector mechanism to avoid an interruption in fluid flow out of the attachment device via the fluid outlet port.

It will be appreciated that maintaining a constant fluid flow, or close to constant, without experiencing a significant drop in pressure for example, during transfer from one fluid source to another fluid source is important in many fields (for example, non-medical fields) to enable optimum performance.

The connector allows fluid communication between a fluid source and an attachment device, but also allows the fluid flow to be selectively started and stopped based on the operator's needs and circumstances during use thereof.

The connector mechanism may comprise at least two couplers each having a wedge member. The wedge members are particularly suitable for moving a ball in a valve, for example. This can be the ball in the valve of an attachment device mechanism, for instance. The shape of the wedge makes it particularly suited for this purpose since sliding the wedge beneath a ball or dome will smoothly move the ball and dome in a constant and predictable manner. Thus, the valve in an attachment device mechanism, for example, can be opened and closed in a predictable and measured way.

The at least two couplers may be pincer rods each having the wedge member disposed at one end thereof. The pincer rods may be elongate in form and may be manufactured from a non-flexible material.

The at least two couplers may be hingeably disposed in the housing. Being hingeably disposed allows the at least two couplers to be pivoted about a point to effect movement in a predetermined path. This path is likely a curved path between a start and finish position, which can correlate with an open valve and closed valve position, or a start flow and stop flow position, for example.

The at least two couplers may be hingeably disposed by a pin in the housing. The pin provides an efficient and reliable manner of pivoting the at least two couplers about their respective hinge points.

The connector mechanism may comprise ball bearings to generate a positive lock engagement. The ball bearings provide a tight seal and lock to inhibit any fluid from undesirably escaping from the connector about its periphery during use. That is, it is desirable that the fluid passing through the connector should exit the connector in a controlled manner due to the function of the connector mechanism.

The connector mechanism may comprise a magnet. The magnet may be positioned centrally with respect to the connector. The magnet may be positioned concentrically with respect to the connector. This enhances the performance of the connector mechanism because it is able to apply a magnetic force equally in all directions—that is the magnetic force is uniform thereby providing a reliable and predictable movement of component (such as a ball or dome-cylinder of an attachment device mechanism) to open and close a valve in reliable and predictable manner, for instance.

The connector may comprise a coupling magnet for connecting a fluid source and an attachment device. The coupling magnet may be positioned at one end of the connector, for instance, for optimum performance and to effect a strong coupling between the connector and another device, such as an attachment device, for example.

The connector may comprise a bleeder valve.

The bleeder valve may comprise a fluid pressure indicator. The bleeder valve and fluid pressure indicator aid an operator in ensuring that the correct/minimum fluid pressure/flow is present before disengaging a fluid source from a fluid inlet port of an attachment device, thereby maintaining the fluid pressure/flow of the fluid entering and exiting the connector and thus the attachment device via the fluid inlet ports and fluid outlet port, respectively.

In another aspect, the present invention comprehends assembly comprising an attachment device, and a connector for connecting at least one fluid source to the attachment device; wherein the attachment device comprising a body having a fluid outlet port and at least two positive pressure fluid inlet ports; wherein each of the at least two positive pressure fluid inlet ports is connectable to a respective fluid source; wherein each of the at least two positive pressure fluid inlet ports is in fluid communication with the fluid outlet port; wherein each of the at least two positive pressure fluid inlet ports comprises an attachment device mechanism for selectively starting and stopping a flow of fluid from the respective fluid source to the fluid outlet port; and wherein the attachment device mechanism comprises a valve moveable between an open valve position and a closed valve position; and wherein the connector being attachable to the at least one fluid source and the attachment device, the connecter connector comprising a housing and a connector mechanism for selectively starting and stopping the flow of fluid from the at least one fluid source to the attachment device.

An assembly formed according to the present invention enables transfer from one fluid source to another fluid source without experiencing a significant disruption of fluid flow. The transfer may thus be a smooth transfer. The transfer may thus be a smooth transition. One fluid source can thus be switched with another fluid source without experiencing a significant disruption of fluid flow or drop in fluid pressure, for example. The assembly enables transfer and/or switching from one fluid source to another fluid source without experiencing a significant interruption of fluid flow. In this way, the fluid flow and/or fluid pressure can be maintained during such a transfer/switch/transition. The assembly enables the transfer/switch/transition of one fluid to another fluid to be gradual to minimize any decline in performance. This can avoid any sharp decline in fluid flow, fluid pressure, and/or overall apparatus performance.

The assembly has particular utility in the medical field of transport ventilation. For instance, the assembly provides a way of transferring to and/or switching from one fluid source (such as oxygen/air) to another fluid source (such as oxygen/air) without experiencing a significant disruption of fluid flow. This can involve maintaining the fluid flow and/or the fluid pressure during transfer and/or switching. Thus, rather than a medical professional/operator completely detaching a patient from one fluid source (for instance oxygen) to transfer to another fluid source (for example oxygen) during transport ventilation when the patient could experience a decrease/lack in oxygen during such transfer, the attachment device enables a continuous delivery of oxygen to the patient via the connector, attachment device, and pressure regulator (which are all in fluid communication with one another during the start flow/open valve positions)—during those critical seconds of transfer from one oxygen source (in ambulance for example) to another oxygen source (in hospital for example). The assembly, thus, facilitates in maintaining the volume of the patient's lungs and, in doing so, avoids collapsing of the lungs which could cause potential further injury and harm to the patient.

The assembly addresses the deficiencies of known constructions and methods employed in transport ventilation, for example, by substantially eliminating those critical seconds where a patient could be starved of oxygen. The assembly involves multiple fluid inlet ports. This is at least two fluid inlet ports, but it will be understood it can be many more fluid inlet ports (for example, three, four, five, and so forth) according to the needs of the application and field. Avoiding the disruption of air/oxygen flow is a significant improvement over current respiratory therapy approaches because it substantially eliminates the harmful side effects that arise as a result of oxygen flow disruption during traditional transport ventilation methods. For example, the at least two fluid inlet ports of the attachment device of the assembly allow at least two fluid lines to be concurrently connected to a patient's breathing respirator or ventilator (including a breathing mask) before one of the fluid lines is ultimately disconnected thereby completing the transfer from one fluid line to the other fluid line without a substantial reduction of fluid flow and performance during the transfer/transition/switch. This is also enabled by each fluid inlet port comprising an attachment device mechanism for selectively starting and stopping the flow of fluid from the respective fluid source to the fluid outlet port of the attachment device of the assembly, such that before stopping the fluid flow from and disconnecting a first fluid line from a first fluid inlet port by way of the attachment device mechanism in that first fluid inlet port, for example, the operator can start fluid flow from a second fluid line into the attachment device by way of the attachment device mechanism in that second other fluid inlet port to avoid an interruption in fluid flow out of the attachment device via the fluid outlet port.

It will be appreciated that maintaining a constant fluid flow, or close to constant, without experiencing a significant drop in pressure for example, during transfer from one fluid source to another fluid source is important in many fields (for example, non-medical fields) to enable optimum performance.

The pressure regulator may be connectable to the fluid outlet port. The connection can be provided by any suitable manner that provide a fast, secure and sealed connection.

The pressure regulator may comprise external threading that is connectable to internal threading of the fluid outlet port. Threading provides a fast and reliable method of connection, which is particularly important during medical emergencies where time is of the essence, and to avoid confusion or delay during connection could save a patient's life.

The pressure regulator may comprise internal threading that is connectable to external threading of the fluid outlet port. Threading provides a fast and reliable method of connection, which is particularly important during medical emergencies where time is of the essence, and to avoid confusion or delay during connection could save a patient's life.

The connector may be connected to the attachment device by at least one selected from the group comprising a push-fit mechanism, bayonet fastening mechanism, and a twist-click seal.

The assembly may comprise a pressure regulator that comprises: a housing formed to include a bore therein; a piston moveably disposed within said bore, wherein said piston comprises an annular lip adjacent a first end thereof; a pressure regulator spring disposed within said bore, and comprising a first end and a second end; and an adjustment cap moveably disposed in said bore, wherein said adjustment cap is formed to include a plurality of key slots formed therein; wherein: said first end of said pressure regulator spring is in physical contact with said annular lip; and said second end of said pressure regulator spring is in physical contact with said adjustment cap wherein: rotating said adjustment cap in a first direction causes said adjustment cap to compress said pressure regulator spring; rotating said adjustment cap in a second and opposite direction causes said adjustment cap to decompress said pressure regulator spring; rotating said adjustment cap in said first direction increases the output pressure of the pressure regulator; rotating said adjustment cap in said second direction decreases the output pressure of the pressure regulator; said bore is defined by a cylindrical wall; said cylindrical wall is formed to include a first threading therein; said adjustment cap is formed to include a second threading formed on a periphery thereof; and said second threading is configured to mesh with said first threading. Such a pressure regulator allows the flow speed and pressure of the fluid to be accurately regulated.

The assembly may further comprise a ventilator connectable to the airway of a living patient, the ventilator comprising: a venturi, comprising a throat; a venturi nozzle; a venturi opening in the venturi nozzle through which pressure-controlled oxygen flows outward, wherein said venturi opening opens to said throat, and wherein said venturi opening and said throat are substantially longitudinally aligned; an ambient air aperture in fluid communication with said venturi nozzle and with ambient air; a fluid port in fluid communication with the airway of the patient; a pressure force multiplier in fluid communication with said fluid port, wherein said pressure force multiplier includes at least one opening defined therethrough; said pressure force multiplier comprising at least one flap movable between an open position and a closed position relative to said at least one opening; and a valve moveable along an axis of movement relative to said venturi opening in said venturi nozzle between a start flow position that causes entrainment of the ambient air by the flow of pressure-controlled oxygen within said throat, and a stop flow position that ceases entrainment of the ambient air by the flow of pressure-controlled oxygen within said throat; wherein said pressure force multiplier is configured wherein exhalation of the patient into said fluid port actuates said valve along said axis of movement relative to said venturi nozzle to close said venturi nozzle; wherein said pressure force multiplier is configured wherein inhalation of the patient through said fluid port actuates said valve along said axis of movement relative to said venturi nozzle; and wherein said axis of movement of said valve is substantially longitudinally aligned with a longitudinal direction of said throat.

Thus, the assembly does not rely on the pressure-controlled fluid to be continuously flowing as is commonly the case with known constructions. Therefore, significant savings, both economic and environmental, can be made due to the present invention actuating the valve to regulate the flow of the pressure-controlled fluid which in effect makes the overall process more efficient. The assembly may be particularly suitable for remote locations, locations in less-developed countries, or other locations that lack access or only have minimal access to plentiful and continuous fluid supplies.

The assembly may comprise any pressure regulator defined herein. This may be in association with the ventilator described above, for instance.

The pressure regulator may be connectable to the ventilator.

The assembly may further comprising an apparatus suitable for use with a respirator, comprising: a venturi, comprising: a throat, a venturi nozzle, and; a venturi opening in the venturi nozzle through which pressure-controlled fluid flows outward, wherein said venturi opening opens to said throat, and wherein said venturi opening and said throat are substantially longitudinally aligned; an ambient fluid aperture in fluid communication with said venturi nozzle and with an ambient fluid; a fluid port; a pressure force multiplier in fluid communication with said fluid port; and a valve moveable along an axis of movement relative to said venturi opening in said venturi nozzle between a start flow position that causes entrainment of the ambient fluid by the flow of pressure-controlled fluid within said throat, and a stop flow position that ceases entrainment of the ambient fluid by the flow of pressure-controlled fluid within said throat; wherein said pressure force multiplier is configured such that fluid forced into said fluid port actuates said valve along said axis of movement relative to said venturi nozzle to close said venturi nozzle; wherein said pressure force multiplier is configured such that fluid withdrawn from said fluid port actuates said valve along said axis of movement relative to said venturi nozzle; wherein said axis of movement of said valve is substantially longitudinally aligned with a longitudinal direction of said throat; and wherein said pressure force multiplier is positioned between said venturi nozzle and said fluid port.

Thus, the assembly does not rely on the pressure-controlled fluid to be continuously flowing as is commonly the case with known constructions. Therefore, significant savings, both economic and environmental, can be made due to the present invention actuating the valve to regulate the flow of the pressure-controlled fluid which in effect makes the overall process more efficient. The assembly may be particularly suitable for remote locations, locations in less-developed countries, or other locations that lack access or only have minimal access to plentiful and continuous fluid supplies.

The assembly may comprise any pressure regulator defined herein. This may be in association with the apparatus described above, for instance.

The pressure regulator may be connectable to the apparatus.

The assembly may further comprise an oxygen-filled reservoir. The oxygen-filled reservoir is particularly beneficial during transport ventilation, for instance, during which time a patient in an ambulance may need a higher dose of oxygen or a constant supply of 100% oxygen. The oxygen-filled reservoir facilitates this need. The oxygen-filled reservoir may also be continually replenished by an oxygen source to ensure a constant supply can reach the patient from the oxygen-filled reservoir. Hence, the oxygen-filled reservoir may be connected to an oxygen source. The oxygen-filled reservoir may be a tank, a tidal volume bag, an entrainment bag, for instance. The ventilator of the assembly can entrain the oxygen from the oxygen-filler reservoir so that the patient is breathing 100% oxygen.

The assembly may comprise a high flow nasal canula for optimum performance and delivery of oxygen to a patient, for example. Such a high flow nasal canula may enable an order of magnitude less of oxygen use, The oxygen-filled reservoir may be connected to the ventilator.

The ventilator may comprise a one-way exhaust valve and a one-way reservoir valve, and wherein the one-way reservoir valve may fluidly connect the oxygen-filled reservoir to the ventilator. This prevents any exhalation air from a patient, for example, from reaching the oxygen-filled reservoir.

The one-way exhaust valve and the one-way reservoir valve may be positioned at the ambient air aperture of the ventilator. This prevents any exhalation air from a patient, for example, from reaching the oxygen-filled reservoir.

The attachment device mechanism and the connector mechanism may be interconnected for selectively starting and stopping the flow of fluid from the fluid source to the attachment device. In this way, the attachment device mechanism and the connector mechanism can work in combination for selectively starting and stopping the flow of fluid from the fluid source to the attachment device within the assembly. This arrangement can provide enhanced performance.

The assembly may further comprise an endotracheal tube that is connected to the fluid outlet port.

The assembly may further comprise a ventilator or ventilator connection tube that is connected to at least one of the at least two positive pressure fluid inlet ports.

In another aspect, the present invention envisages a method of switching one fluid source with another fluid source and maintaining continuous positive pressure fluid flow to a respirator or ventilator, comprising the steps of: providing the respirator or the ventilator; providing the one fluid source; attaching said one fluid source to one connector, said one connector comprising one housing and one connector mechanism for selectively starting and stopping a flow of fluid; providing an attachment device comprising a body having a fluid outlet port and at least two positive pressure fluid inlet ports; wherein each of the at least two positive pressure fluid inlet ports is connectable to a respective fluid source; wherein each of the at least two positive pressure fluid inlet ports is in fluid communication with the fluid outlet port;
wherein each of the at least two positive pressure fluid inlet ports comprises an attachment device mechanism for selectively starting and stopping the flow of fluid; and wherein the attachment device mechanism comprises a valve moveable between an open valve position and a closed valve position; providing a pressure regulator for regulating fluid pressure and fluid flow speed; connecting the fluid outlet port of the attachment device to the pressure regulator;
connecting the pressure regulator to the respirator or the ventilator; connecting said one connector to one fluid inlet port of the attachment device; selectively starting the flow of fluid from said one fluid source to the respirator or the ventilator using said one connector mechanism and said one attachment device mechanism; providing another fluid source;
attaching said another fluid source to another connector, said another connector comprising another housing and another connector mechanism for selectively starting and stopping the flow of fluid; connecting said another connector to another fluid inlet port of the attachment device; selectively starting the flow of fluid from said another fluid source to the respirator or the ventilator using said another connector mechanism and another attachment device mechanism; selectively stopping the flow of fluid from said one fluid source to the respirator or the ventilator using said one connector mechanism and said one attachment device mechanism; and disconnecting said one connector from said one fluid inlet port of the attachment device.

It may be that at least one of said attachment device, said one connector and said another connector comprises a bleeder valve having a fluid pressure indicator, and the method may further comprise the step of checking the fluid pressure indicator before the steps of selectively stopping flow of fluid from said one fluid source and disconnecting said one connector from said one fluid inlet port of the attachment device.

The step of providing a pressure regulator for regulating fluid pressure and fluid flow speed may comprise providing a pressure regulator that comprises: a housing formed to include a bore therein; a piston moveably disposed within said bore, wherein said piston comprises an annular lip adjacent a first end thereof; a pressure regulator spring disposed within said bore, and comprising a first end and a second end; and an adjustment cap moveably disposed in said bore, wherein said adjustment cap is formed to include a plurality of key slots formed therein; wherein: said first end of said pressure regulator spring is in physical contact with said annular lip; and said second end of said pressure regulator spring is in physical contact with said adjustment cap wherein: rotating said adjustment cap in a first direction causes said adjustment cap to compress said pressure regulator spring; rotating said adjustment cap in a second and opposite direction causes said adjustment cap to decompress said pressure regulator spring; rotating said adjustment cap in said first direction increases the output pressure of the pressure regulator; rotating said adjustment cap in said second direction decreases the output pressure of the pressure regulator; said bore is defined by a cylindrical wall; said cylindrical wall is formed to include a first threading therein; said adjustment cap is formed to include a second threading formed on a periphery thereof; and said second threading is configured to mesh with said first threading.

The step of providing a ventilator may comprise providing a ventilator that is connectable to the airway of a living patient, the ventilator comprising: a venturi, comprising a throat; a venturi nozzle; a venturi opening in the venturi nozzle through which pressure-controlled oxygen flows outward, wherein said venturi opening opens to said throat, and wherein said venturi opening and said throat are substantially longitudinally aligned; an ambient air aperture in fluid communication with said venturi nozzle and with ambient air; a fluid port in fluid communication with the airway of the patient; a pressure force multiplier in fluid communication with said fluid port, wherein said pressure force multiplier includes at least one opening defined therethrough; said pressure force multiplier comprising at least one flap movable between an open position and a closed position relative to said at least one opening; and a valve moveable along an axis of movement relative to said venturi opening in said venturi nozzle between a start flow position that causes entrainment of the ambient air by the flow of pressure-controlled oxygen within said throat, and a stop flow position that ceases entrainment of the ambient air by the flow of pressure-controlled oxygen within said throat; wherein said pressure force multiplier is configured wherein exhalation of the patient into said fluid port actuates said valve along said axis of movement relative to said venturi nozzle to close said venturi nozzle; wherein said pressure force multiplier is configured wherein inhalation of the patient through said fluid port actuates said valve along said axis of movement relative to said venturi nozzle; and wherein said axis of movement of said valve is substantially longitudinally aligned with a longitudinal direction of said throat.

The method may be for use in transport ventilation.

The characteristics and utilities of the present invention described in this summary and the detailed description below are not all inclusive. Many additional features and advantages will be apparent to one of ordinary skill in the art given the following description. There has thus been outlined, rather broadly, the more important features of the invention in order that the detailed description thereof that follows may be better understood, and in order that the present contribution to the art may be better appreciated.

BRIEF DESCRIPTION OF THE DRAWINGS

The use of the same reference symbols in different figures indicates similar or identical items.

DETAILED DESCRIPTION

Figure 1:
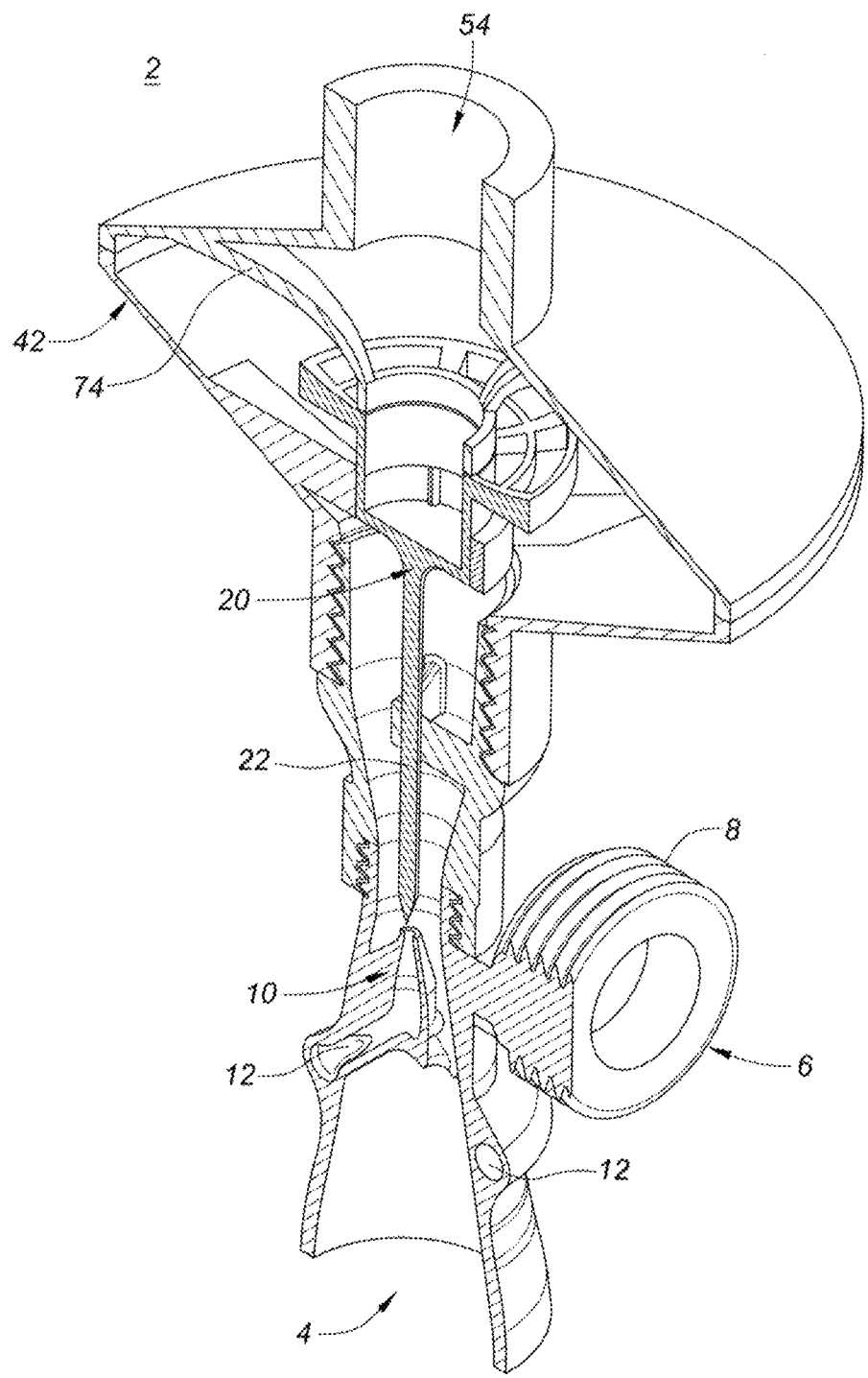
FIG. 1 is a perspective cutaway view of a ventilator in an inhalation configuration.
Figure 2:
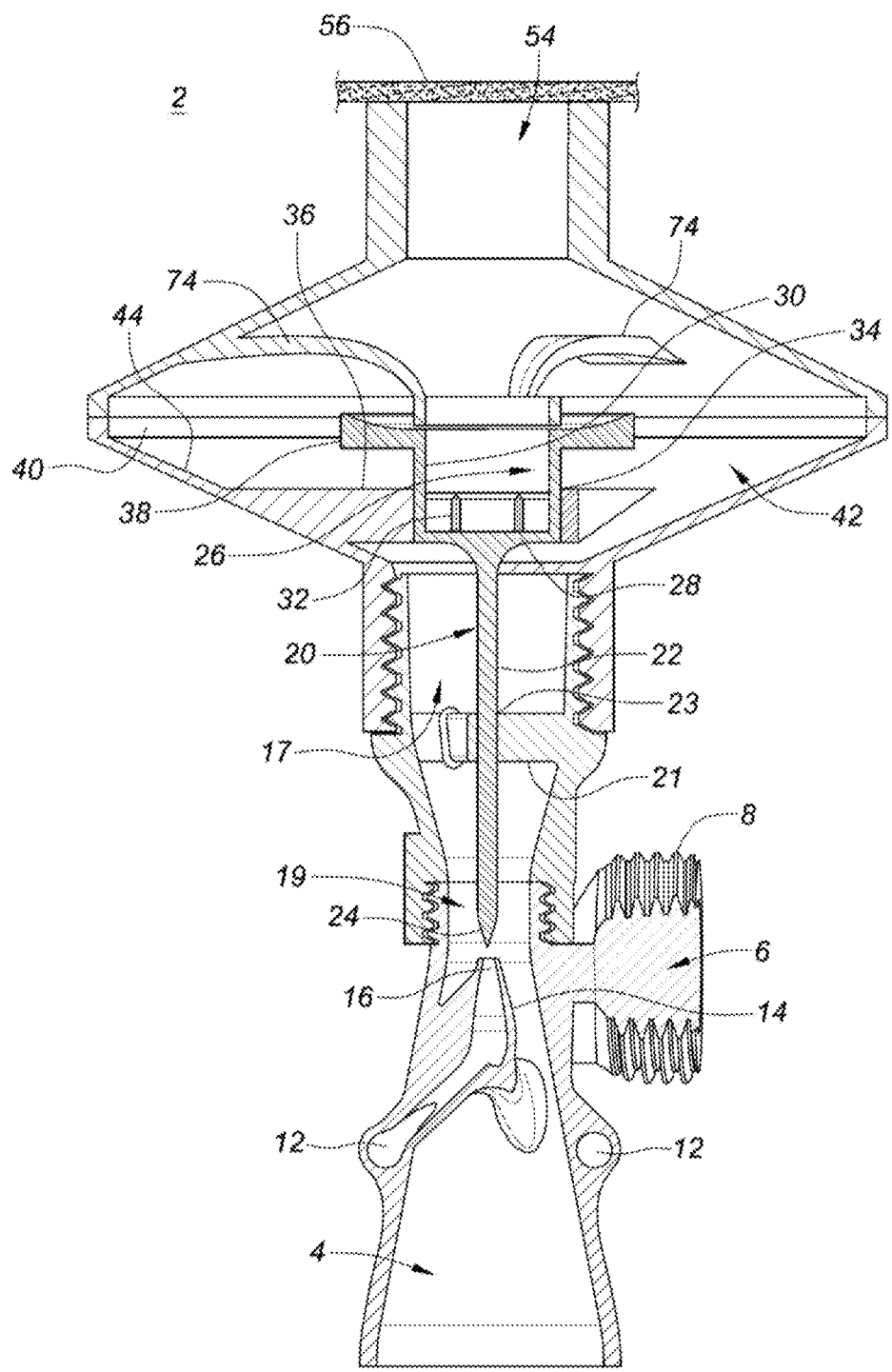
FIG. 2 is a side cutaway view of the ventilator of FIG. 1 in the inhalation configuration.

Referring to FIGS. 1-2, one embodiment of a fluid mixer 2 is shown. The fluid mixer 2 also may be referred to as a fluid mixing apparatus 2 or apparatus 2. The fluid mixer 2 may be used in a variety of applications. For example, the fluid mixer 2 may find use in medical applications, automotive applications, racing applications, and other applications. As seen in FIGS. 1-2, the fluid mixer 2 is a ventilator 2. The term "ventilator," as used in this document, encompasses any and all medical applications in which the ventilator 2 may be used, such as but not limited to continuous positive airway pressure (CPAP) machines, and bilevel positive airway pressure (BiPAP) machines.

Returning to FIGS. 1-2, an exemplary ventilator 2 is shown in an inhalation configuration, in which a patient is inhaling gas through the ventilator 2. Advantageously, the ventilator 2 is solely mechanical. As used in this document, the term "solely mechanical" is defined to mean a mechanism operable based on gas pressure changes controlled by a patient's breath, without electricity or electronics. According to other embodiments, the ventilator 2 may be controlled, powered, or otherwise operated in whole or in part using electricity and/or electronics. The ventilator 2 includes an ambient fluid aperture 4, which may be generally bell-shaped, or which may have any other suitable shape. The opening of the ambient fluid aperture 4 may have any suitable shape, such as but not limited to circular, oval, rectilinear, or polygonal, and may be bilaterally and/or radially symmetrical, or asymmetrical. The ambient fluid aperture 4 may be located at one end of the ventilator 2. The ventilator 2 also includes a fluid inlet 6, located in proximity to the ambient fluid aperture 4. The fluid inlet 6 may be connected to a source of pressure-controlled fluid, such as oxygen. As seen in FIG. 1, the ambient fluid aperture 4 and the fluid inlet 6 may be arranged generally perpendicular to one another; however, the ambient fluid aperture 4 and the fluid inlet 6 may be arranged relative to one another in any other suitable manner. The fluid inlet 6 may include threads 8 defined on an outer diameter thereof, to facilitate the connection of oxygen or other pressure-controlled fluid to the ventilator 2. Advantageously, the pressure entering the fluid inlet 6 is slightly above ambient. The pressure at the fluid inlet 6 may be adjusted as described in greater detail below. As utilized in the treatment of patients, the fluid inlet 6 may be an oxygen inlet, through which oxygen enters the ventilator 2.

Air from the ambient fluid aperture 4 and oxygen from the fluid inlet 6 are mixed in a venturi 10. According to some embodiments, passages 12 are defined in the ventilator 2 radially outside the ambient fluid aperture 4, and oxygen from the fluid inlet 6 travels from the fluid inlet 6 through the passages 12 to a venturi nozzle 14 and out the venturi opening 16 in the venturi nozzle 14. The specific path, cross-section and other details of the passages 12 are not critical to the invention; rather, as long as a sufficient amount of oxygen is delivered to the venturi opening 16, the passages 12 may be configured in any manner. An air passage 18 allows air to flow from the ambient fluid aperture 4 to the venturi nozzle 14. As oxygen exits the venturi opening 16 of the venturi nozzle 14, that oxygen flow entrains air from the throat 19 of the venturi 10 and mixes with that entrained air, which is oxygen-enriched compared to ambient air. Above the venturi nozzle 14, a central passage 17 extends upwards, allowing oxygen-enriched air to travel to the patient during inhalation, and allowing exhalation air to travel outward from the patient during exhalation. As is well understood in the art, a venturi is typically a short tubular section with a tapering constriction (throat 19) in the middle that causes an increase in the velocity of flow of a fluid passing therethrough. As can be seen from FIGS. 1-2, the venturi opening 16 in the venturi nozzle 14, through which pressure-controlled oxygen (or other pressure-controlled fluid for example) flows outward, opens to said throat 19, and wherein said venturi opening 16 and said throat 19 are substantially longitudinally aligned.

A valve 20 is positioned above the venturi nozzle 14. As used in this document, words of orientation such as "top," "bottom," "above," "below" and the like refer to the orientation of and relative location of parts shown in the Figures relative to the page for ease of description; the ventilator 2 can be used in any orientation, and such words of orientation do not limit use of the ventilator 2. The valve 20 includes a stem 22, which may include a tapered end 24 according to some embodiments. The tapered end 24 may be tapered such that a portion of the tapered end 24 has a diameter less than the diameter of the venturi opening 16 and can enter the venturi nozzle 14 through the venturi opening 16. In the open, inhalation position shown in FIG. 1 the tapered end 24 is spaced apart from the venturi opening 16 such that oxygen can flow out of the venturi opening 16 and entrain ambient air from the air passage 18 in the throat 19 of the venturi 10. According to other embodiments, the stem 22 need not include a tapered end 24, and may instead include an end that grows wider in diameter closer to the venturi nozzle 14, such that the wider end is capable of blocking the venturi opening 16 in a closed position without substantially entering the venturi opening 16. A stem seat 21 may extend laterally toward the stem 22, and may include a stem aperture 23 configured to receive and guide the stem 22 in its longitudinal motion, while substantially restraining the stem 22 against lateral motion. The stem aperture 23 may have a shape similar to and slightly larger than the stem 22. For example, where the stem 22 is generally cylindrical, the outer diameter of the stem 22 may be slightly smaller than the diameter of the stem aperture 23, such that the stem aperture 23 allows the stem 22 to slide relative to the stem aperture 23 while the stem aperture 23 also limits the lateral motion of the stem 22. The valve 20 may be free-floating, as seen in FIGS. 1-2. Optionally, the valve 20 may be biased toward the inhalation configuration shown in FIGS. 1-2, such as by a spring (not shown) or other structure or mechanism. Alternately, the valve 20 may be biased toward the exhalation configuration, such as by a spring (not shown) or other structure or mechanism.

The stem 22 extends from the tapered end 24 to a vent ring 26. The vent ring 26 may be generally cylindrical in shape, including a generally circular bottom 28 and a curved body 30. One or more windows 32 may be defined through the curved body 30. The vent ring 26 may be received by an aperture 34 in a vent ring seat 36. The aperture 34 may have a shape similar to and slightly larger than the vent ring 26. For example, where the vent ring 26 is generally cylindrical, the outer diameter of the vent ring 26 may be slightly smaller than the diameter of the aperture 34, such that the aperture 34 of the vent ring seat 36 allows the vent ring 26 to slide relative to the aperture 34 while the aperture 34 also limits the lateral motion of the vent ring 26. At least one flange 38 may extend radially outward from the vent ring 26. The flange 38 may extend outward from an upper edge of the vent ring 26, or from any other suitable portion of the vent ring 26.

The flange 38 may be connected to a pressure force multiplier 40 within a chamber 42; advantageously, the flange 38 is fixed to the pressure force multiplier 40. According to some embodiments, the pressure force multiplier 40 is a diaphragm 40. The diaphragm 40 extends radially between the vent ring 26 and the inner surface 44 of the chamber 42. The diaphragm 40 is flexible and durable, and may be fabricated from any suitable material such as rubber, latex, plastic or other material or materials. Because the flange 38 is connected to the diaphragm 40, downward motion of the diaphragm 40 causes the flange 38, and thus the valve 20 as a whole, to move downward; upward motion of the diaphragm 40 causes the flange 38, and thus the valve 20 as a whole, to move upward. According to some embodiments, the diaphragm 40 may be biased toward its position in the inhalation configuration. According to other embodiments, the diaphragm 40 may be bistable, such that it is stable both in its position in the inhalation configuration and its position in the exhalation configuration. In this embodiment, the valve 20 is moveable along an axis of movement relative to said venturi opening 16 in said venturi nozzle 14 between a start flow position that causes entrainment of the ambient fluid by the flow of pressure-controlled fluid (for example, pressure-controlled oxygen) within said throat 19, and a stop flow position that ceases entrainment of the ambient fluid by the flow of pressure-controlled fluid within said throat 19. For instance, in an embodiment of the present invention, said pressure force multiplier 40 is configured such that fluid forced into said fluid port 54 actuates said valve 20 along said axis of movement relative to said venturi nozzle 14 to close said venturi nozzle 14; additionally, in an embodiment of the present invention, said pressure force multiplier 40 is configured such that fluid withdrawn from said fluid port 54 actuates said valve 20 along said axis of movement relative to said venturi nozzle 14. The axis of movement of said valve 20, in this embodiment, is substantially longitudinally aligned with a longitudinal direction of said throat 19. In this embodiment, at least a portion of said valve 20 is movable, along said axis of movement, within said throat 19.

Figure 2A:
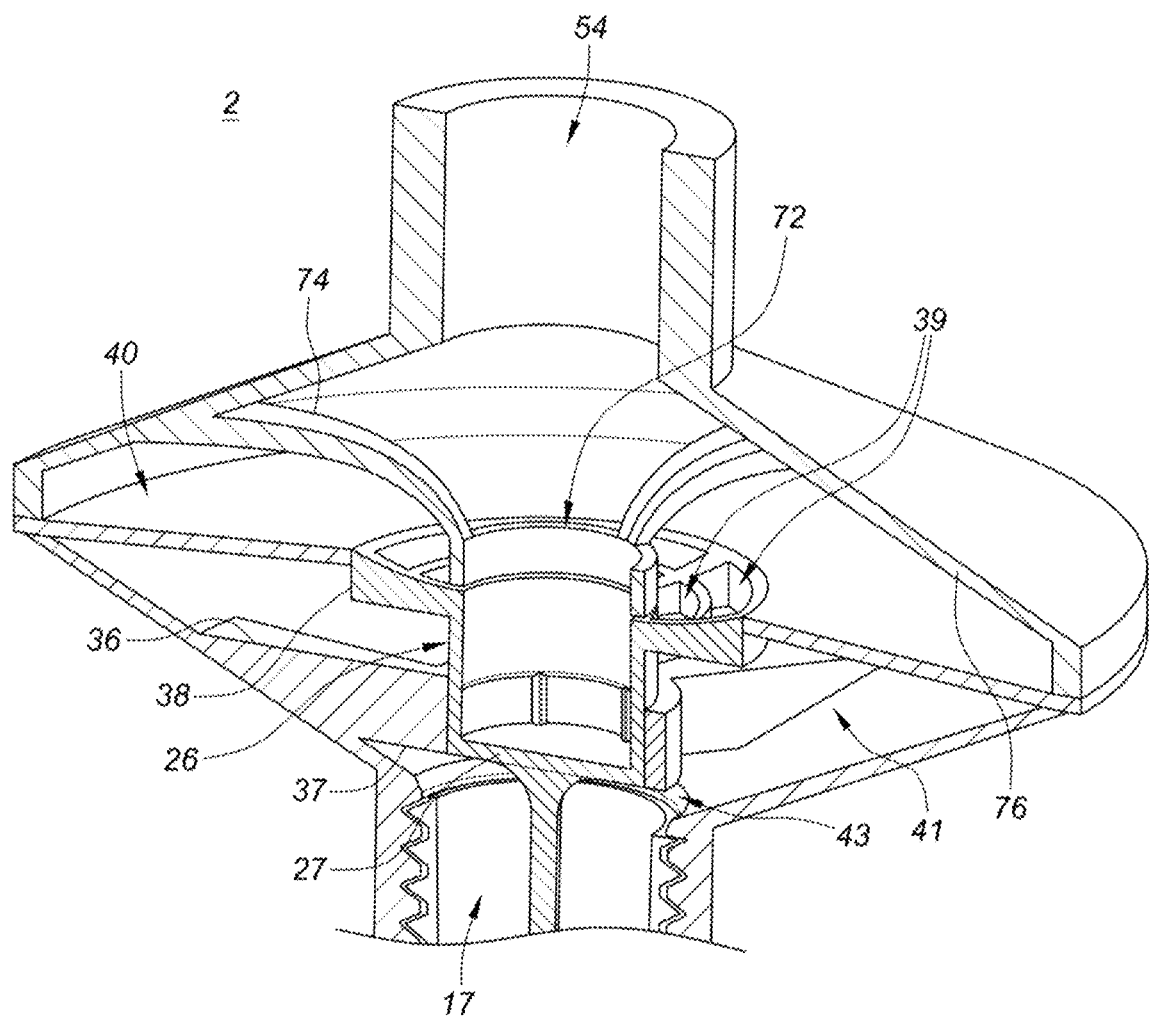
FIG. 2A is a detail perspective cutaway of the ventilator of FIG. 1 in the inhalation configuration, showing a diaphragm in the inhalation configuration.

Referring also to FIG. 2A, in the inhalation configuration, an inlet passage 41 is in fluid communication with the central passage 17. The vent ring 26 is in an upward position relative to the venturi nozzle 14. As a result, the bottom 27 of the vent ring 26 may be substantially even with the lower surface 37 of the vent ring seat 36, and the inlet aperture 43 is thus open, placing the central passage 17 in fluid communication with the inlet passage 41. The flange 38 may be configured as a grid or grate, such as the concentric grid shown in FIG. 2A, such that a plurality of flange openings 39 allow fluid to flow therethrough. In the inhalation configuration, both sides of the diaphragm 40 are thus in fluid communication with one other via the flange openings 39; those flange openings 39 place the inlet passage 41 and the fluid port 54 in fluid communication in the inhalation configuration. Thus, in the inhalation configuration, the central passage 17, the inlet passage 41, and the fluid port 54 are in fluid communication with one another, such that enriched air flows freely from the venturi nozzle 14 to the fluid port 54, and then to the patient.

Where the diaphragm 40 is bistable, the diaphragm 40 may be in one of its two bistable configurations in the inhalation configuration, as seen in FIG. 2A. Utilizing a bistable diaphragm 40 with a stable configuration in the inhalation configuration means the patient need not utilize any breathing force to maintain the inhalation configuration after that inhalation configuration has been reached; as a result, the ventilator 2 may be useful for treating patients with degraded breathing capability. Where the diaphragm 40 is stable in a single configuration, that configuration may be the inhalation configuration as shown in FIG. 2A.

The pressure force multiplier 40 is in fluid communication with said fluid port 54, wherein said pressure force multiplier 40 includes at least one opening 39 defined therethrough; said pressure force multiplier 40 comprising at least one flap 70 movable between an open position and a closed position relative to said at least one opening 39. One or more flaps 70 may be associated with the flange 38, referring also to FIG. 3B. The flaps 70 are described in greater detail below with regard to FIG. 3B. In the inhalation configuration, fluid flow toward the fluid port 54 causes the flaps 70 to be blown upward away from the flange 38 and its (flange) openings 39, allowing for the free flow of enriched air to the patient through the (flange) openings 39. In this embodiment, said pressure force multiplier 40 is positioned between said venturi nozzle 14 and said fluid port 54.

A limiter 72 optionally may be positioned in the chamber 42 above the flange 38. According to some embodiments, the limiter 72 may be a ring having substantially the same diameter as the vent ring 26, where the limiter 72 is substantially coaxial with the vent ring 26. The limiter 72 may be connected to, fixed to, or integral with one or more ribs 74 that extend therefrom. The one or more ribs 74 may extend upward from the limiter 72; alternately, one or more ribs 74 may extend laterally from or downward from the limiter 72. The ribs 74 may be substantially rigid, such that they do not substantially undergo bending or flexure during normal usage of the ventilator 2. According to other embodiments, one or more ribs 74 may be flexible. Each rib 74 is connected at one end to the limiter 72, and at the other end to a portion of the chamber 40. For example, one or more ribs 74 are connected to the upper wall 76 of the chamber 40. The ribs 74 may be fixed to or integral with the upper wall 76 of the chamber 40. For example, the upper wall 76 of the chamber 40, the ribs 74, and the limiter 72 may be injection molded, fabricated by additive manufacturing, or fabricated in any other manner as a single integral piece. The limiter 72 prevents the vent ring 26, and thus the valve 20, from moving upward out of the vent ring seat 36 and/or the stem seat 21.

According to some embodiments, the limiter 72 has another shape than a ring. For example, the limiter 72 may be a bar, a rod, an X-shape, a square, a rectangle, an oval, or any other suitable shape. The limiter 72 may have any shape, and be placed relative to the vent ring 26 in any location, that both engages the vent ring 26 in the inhalation configuration to limit its travel upward to prevent the valve 20 and/or the vent ring 26 from becoming unseated, and allows for substantially unrestricted fluid flow out of the flange openings 39.

At the upper end of the chamber 42, a fluid port 54 allows inhalation air to flow out of the ventilator 2 and exhalation air to flow into the ventilator 2. At least one filter 56 may be positioned adjacent to the fluid port 54, in order to filter both inhalation and exhalation air. The filter 56 advantageously is a 3 micron filter or other filter suitable for removing viruses, pollen and other airborne contaminants from the air. In this way, the filter 56 protects the patient from ambient contaminants, and also protects others near the ventilator 2 from infection from air exhaled from the patient. The filter 56 is detachably connected to the ventilator 2, so that the filter 56 may be periodically replaced. The filter 56 may be a single-use filter, or may be cleanable and sterilizable such that it can be reused after cleaning and sterilization. Alternately, the filter 56 may be placed adjacent to the ambient fluid aperture 4, or at another location on the ventilator 2. For example, according to some embodiments, the filter 56 is positioned adjacent to the ambient fluid aperture 4, in order to filter both inhalation and exhalation air. In this way, the filter 56 protects the patient from ambient contaminants, and also protects others near the ventilator 2 from infection from air exhaled from the patient. Alternately, more than one filter 56 may be utilized.

The chamber 42 may be connected via the fluid port 54 to a respirator (not shown) that is worn by the patient. As typically used in the industry, the term "respirator" refers to a device that provides respirable air to a patient or other user, such as by providing a supply of breathable gas. However, as used in this document, the term "respirator" is specifically defined to exclude any requirement that the respirator itself filter anything from the air provided to the patient, or exhaled by the patient. According to some embodiments, the respirator is substantially impermeable to fluid, whether gas or liquid. According to some embodiments, the respirator may be a mask provided with compliant sealing surfaces or other seal or seals such that a substantially airtight seal is created against the patients face. According to some embodiments, the respirator may be a helmet or other structure that engages a different part of the patient than the face; for example, the respirator may be a helmet that substantially seals against the patient's neck and does not touch the face. According to some embodiments, all of the respirator or a portion of the respirator may be positioned within the patient's nose and/or mouth, and the respirator is substantially sealed relative to the nose and/or mouth. According to some embodiments, such as those described above, the respirator is substantially sealed relative to the patient's airway. By substantially sealing the respirator relative to the patient's airway, slight pressure changes when the patient breathes cause the valve 20 to move, as described in greater detail below. In this way, the respirator and thus the patient are in fluid communication with the ventilator 2. Because the respirator is substantially impermeable to gas, substantially all of the patient's exhalation breath reaches the fluid port 54 of the ventilator 2, such that only a small exhalation effort causes the valve 20 to move. Alternately, the respirator and the patient may be in fluid communication with the ventilator 2 in any other suitable manner.

Figure 3:
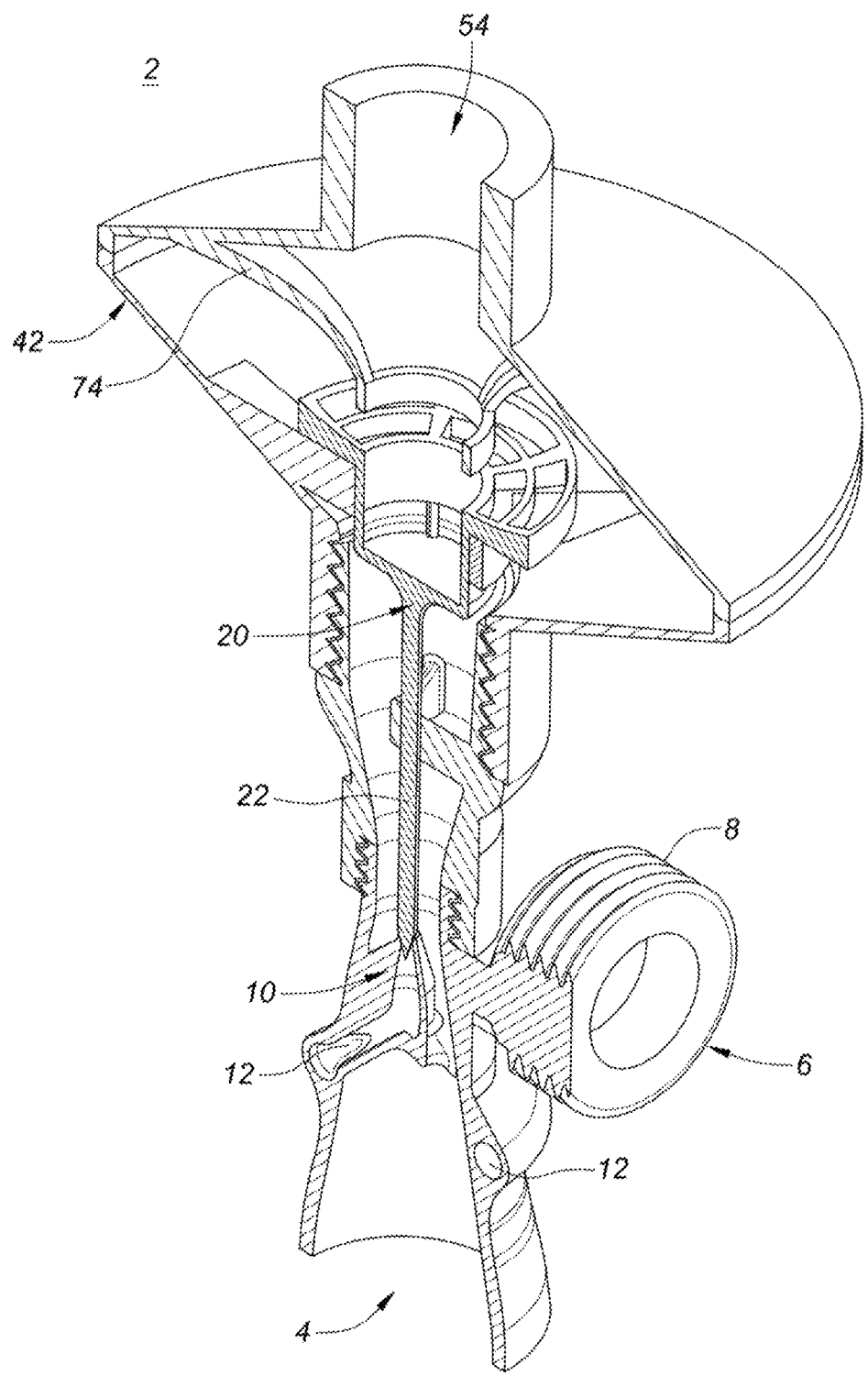
FIG. 3 is a perspective cutaway view of the ventilator in an exhalation configuration.
Figure 4:
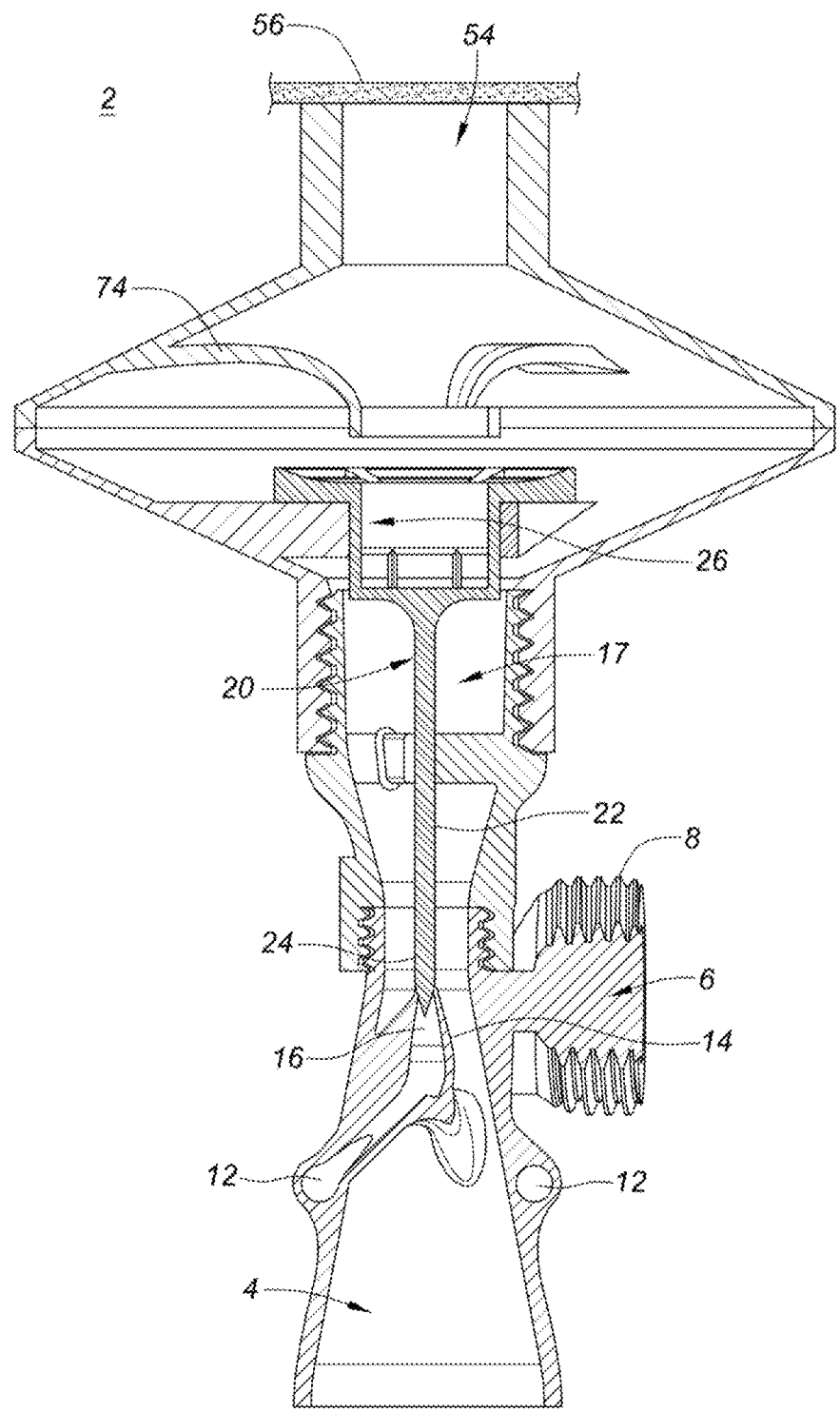
FIG. 4 is a side cutaway view of the ventilator of FIG. 3 in the exhalation configuration.
Figure 5:
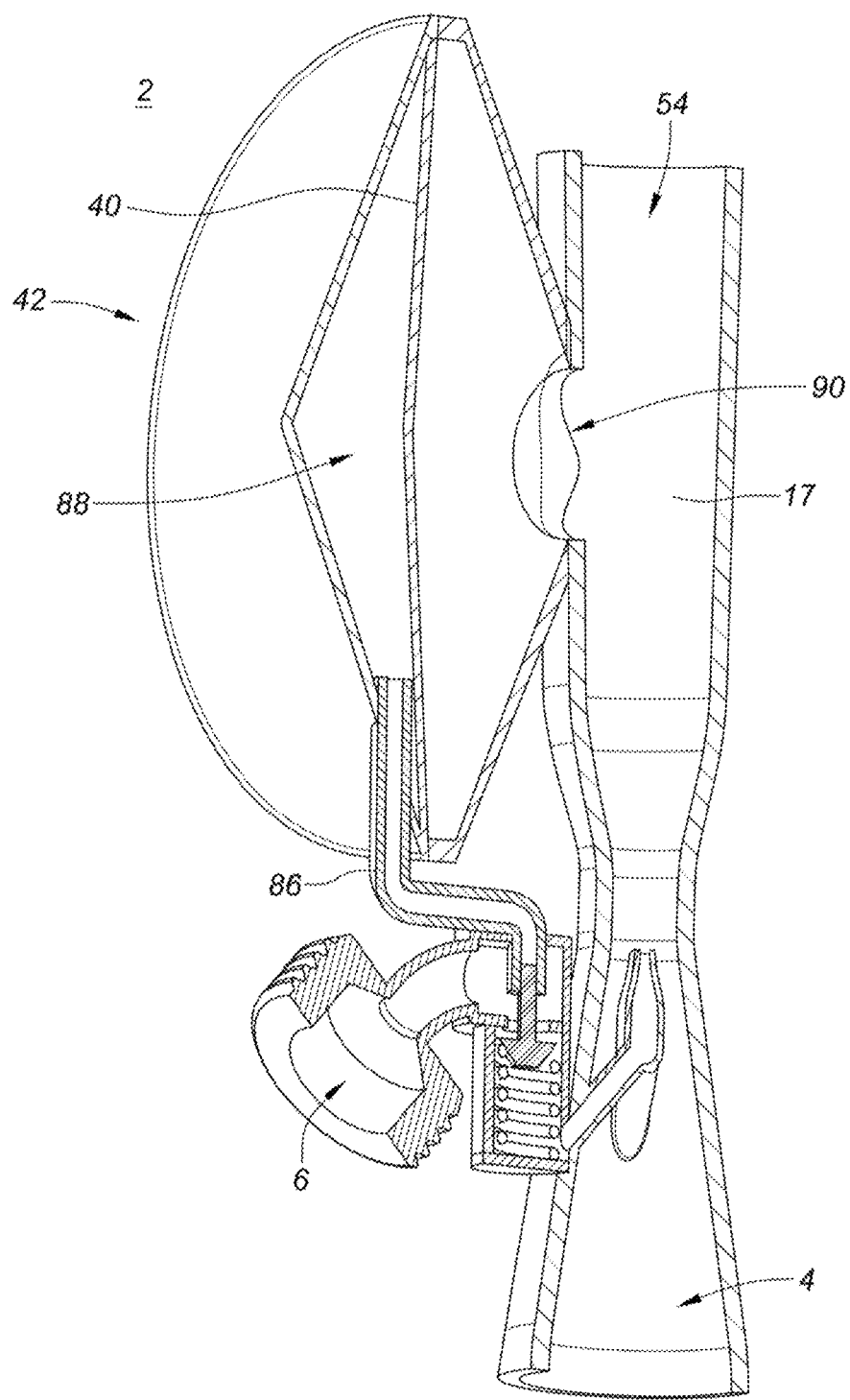
FIG. 5 is a perspective cutaway view of another embodiment of the ventilator.
Figure 6:
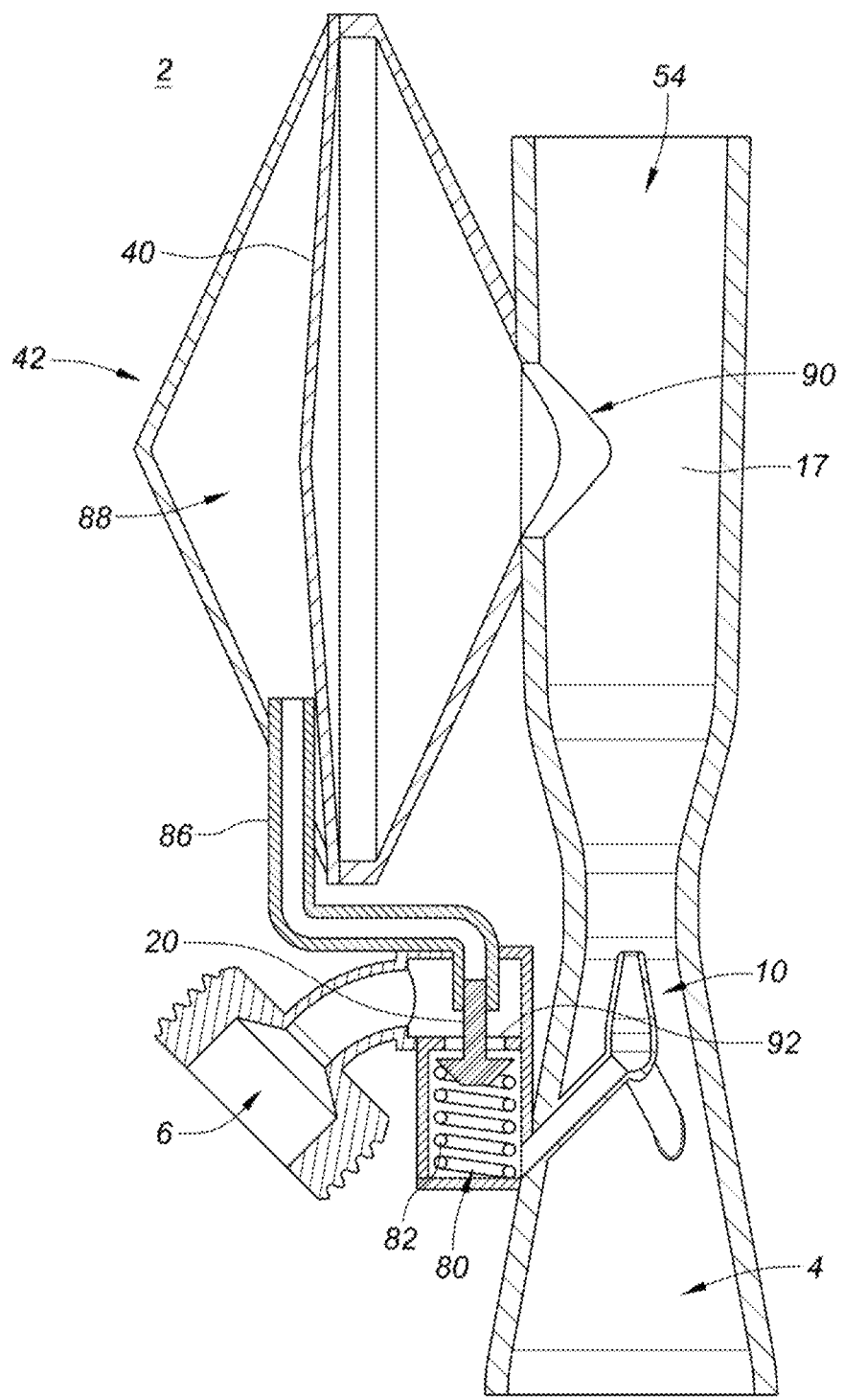
FIG. 6 is a side cutaway view of the ventilator of FIG. 5.
Figure 7:
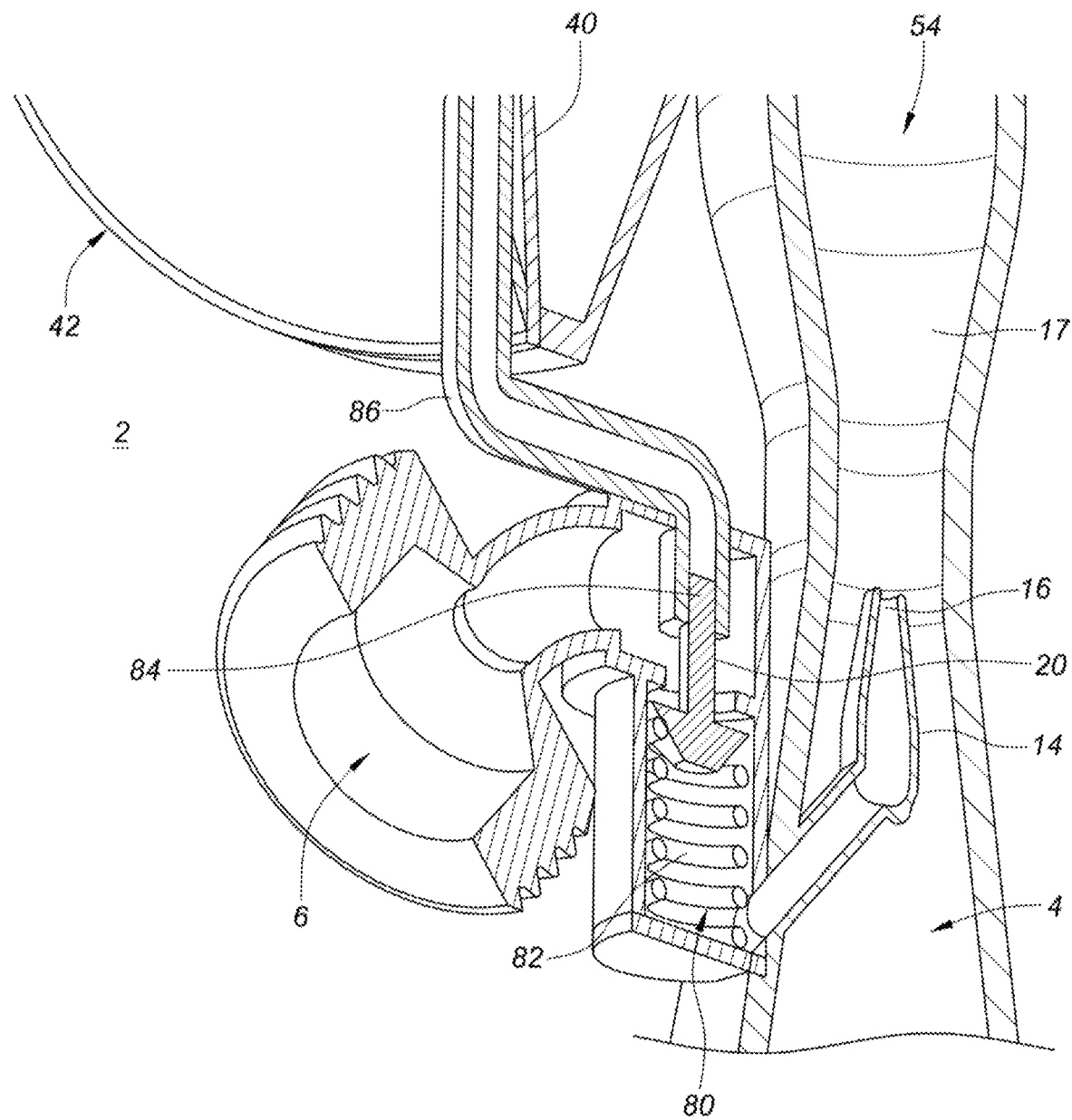
FIG. 7 is a detail perspective cutaway view of a valve of the ventilator of FIG. 5.
Figure 8:
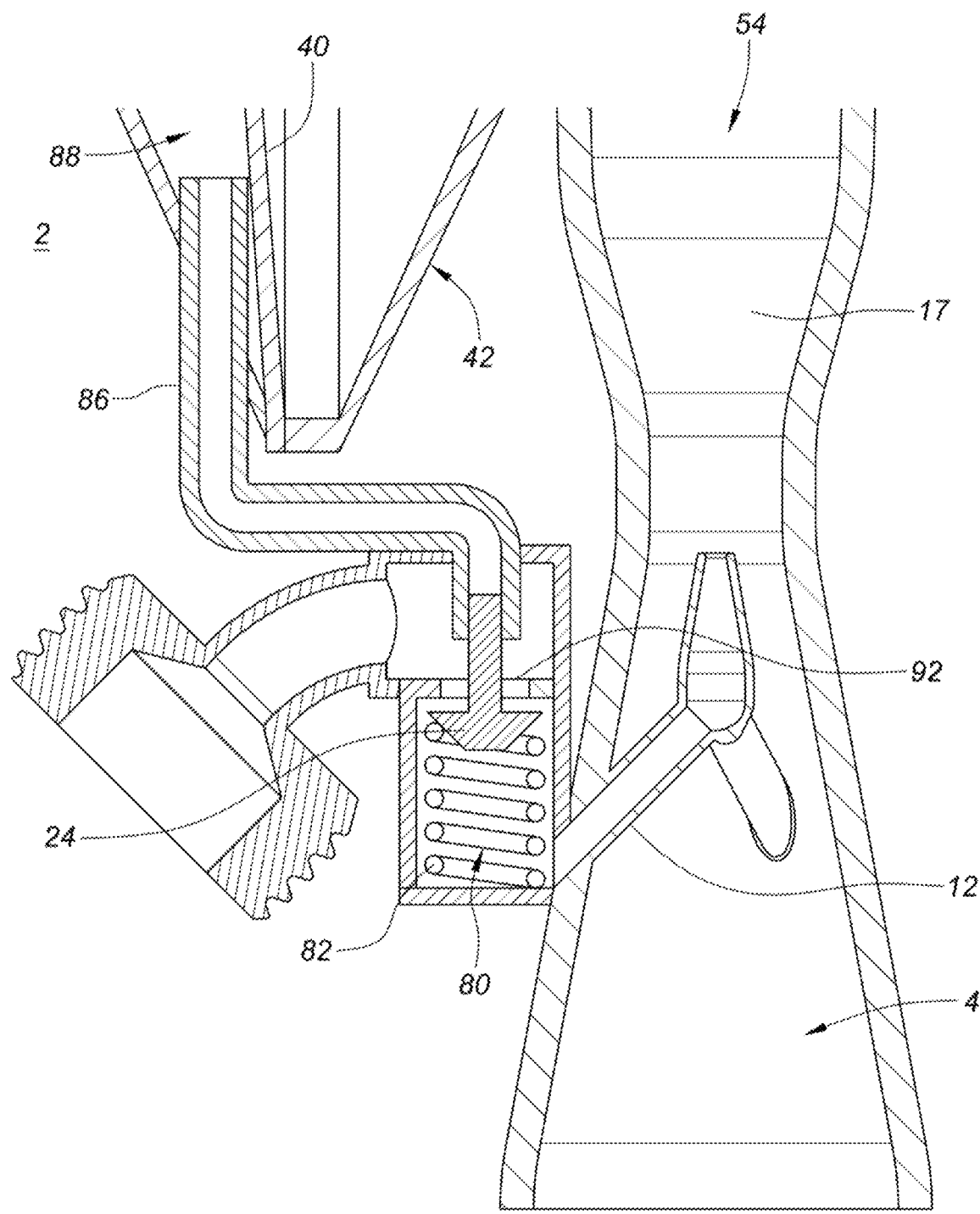
FIG. 8 is detail side cutaway view of a valve of the ventilator of FIG. 5.
Figure 9:
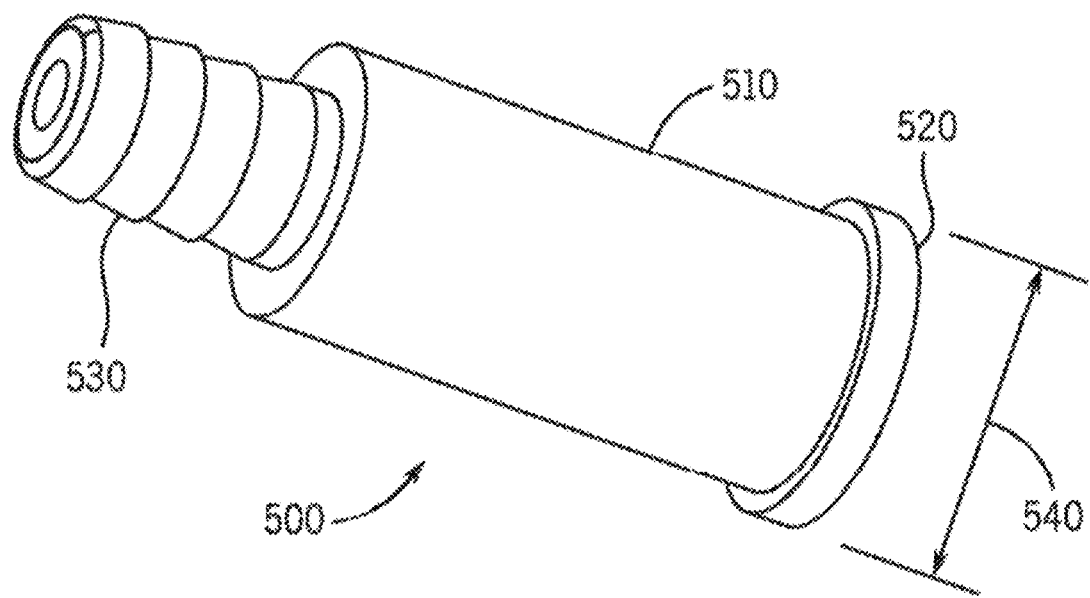
FIG. 9 is a perspective view of one embodiment of a secondary regulator 500.
Figure 10:
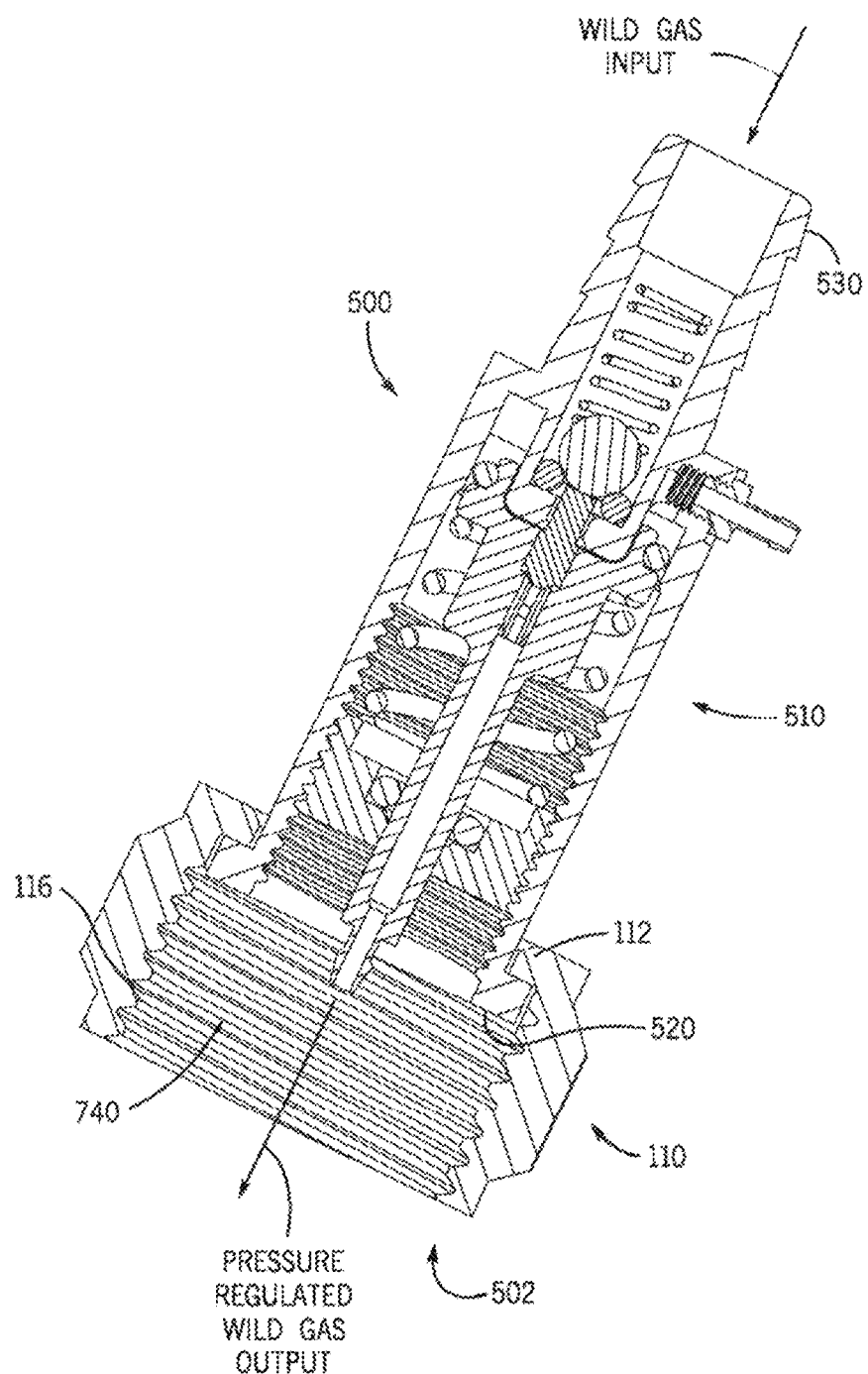
FIG. 10 is a cross-sectional view of the secondary regulator 500.

Referring to FIGS. 3-4, a ventilator 2 is shown in an exhalation configuration, in which a patient is exhaling gas through the ventilator 2. As described in greater detail below, exhalation pressure from the patient flexes the center of the diaphragm 40 downward. As a result, the flange 38, which is connected to the diaphragm 40, moves downward. Downward motion of the flange 38 may be limited by the vent ring seat 36, the upper surface of which may engage a lower surface of the flange 38, thereby preventing further downward motion of the flange 38. In the exhalation configuration, the valve 20 has moved downward relative to the venturi nozzle 14, and the tapered end 24 of the stem 22 substantially blocks the venturi opening 16. In this way, oxygen flow from the fluid inlet 6 outward through the venturi opening 16 is substantially stopped. Advantageously, the length of the stem 22 is fabricated such that the tapered end 24 or other lower end of the stem 22 substantially blocks the venturi opening 16 when the flange 38 engages the vent ring seat 36.

Figure 3A:
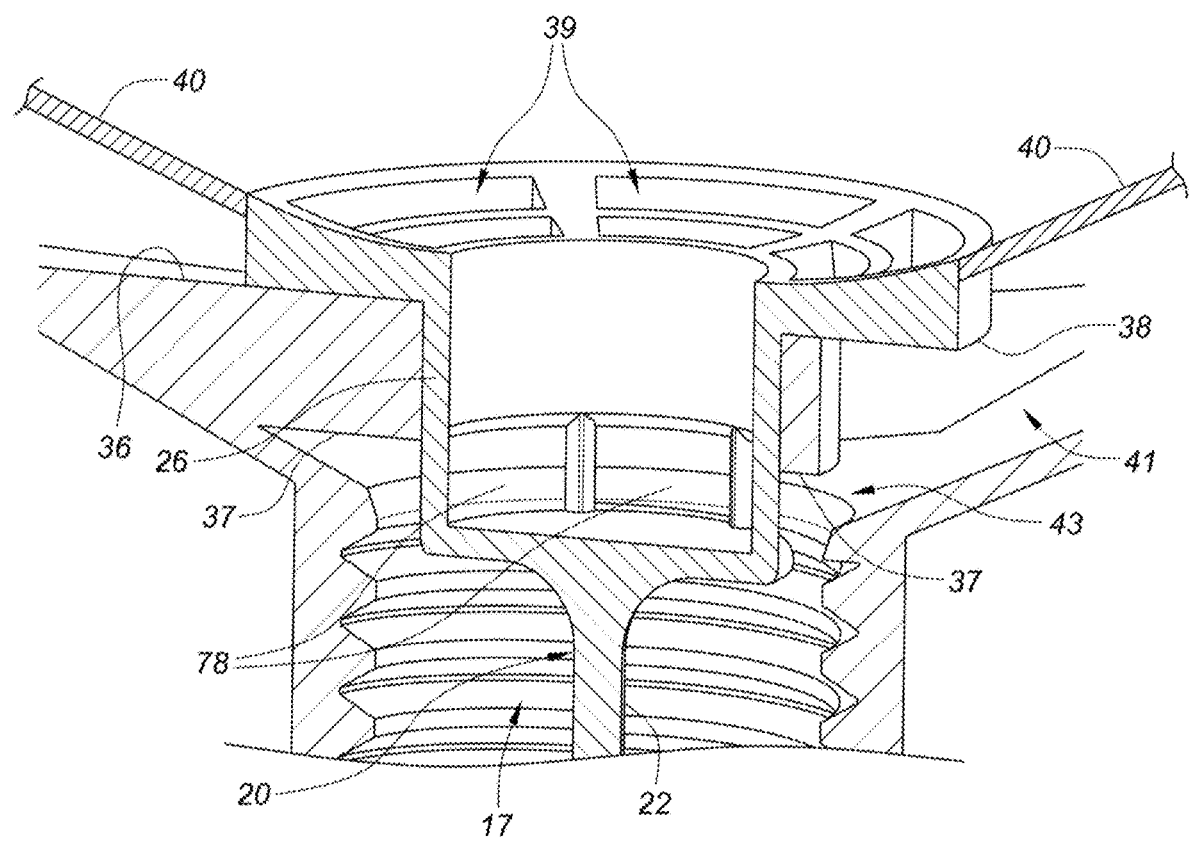
FIG. 3A is a detail perspective cutaway of the ventilator of FIG. 3 in the exhalation configuration, showing exhalation windows.

Referring also to FIG. 3A, in the exhalation configuration, the inlet passage 41 is no longer substantially in fluid communication with the central passage 17. The vent ring 26 is in an downward position relative to the venturi nozzle 14. As a result, the bottom 27 of the vent ring 26 is positioned below the lower surface 37 of the vent ring seat 36, and the inlet aperture 43 is thus closed, substantially closing the central passage 17 in fluid communication with the inlet passage 41. An O-ring or other seal (not shown) may extend radially outward from the vent ring seat 36 to facilitate closure of the inlet aperture 43 in the exhalation configuration. Alternately, the inlet aperture 43 need not be closed, in whole or in part, in the exhalation configuration, because exhalation air will still travel outward through the central passage 17 as described below.

Figure 3B:
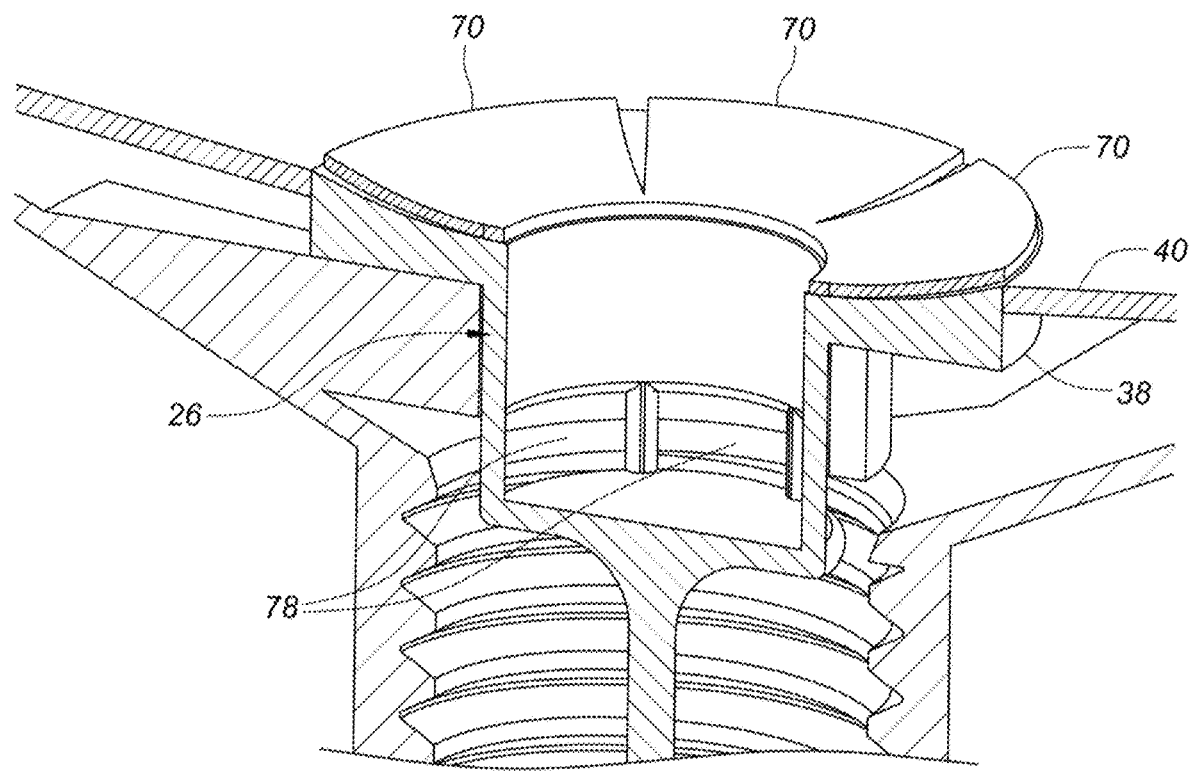
FIG. 3B is a detail perspective cutaway of the ventilator of FIG. 3 in the exhalation configuration, showing flaps.

In the exhalation configuration, the flange 38 has moved downward relative to its position in the inhalation configuration, and may be in contact with the vent ring seat 36. In this way, the vent ring seat 36 may act to limit downward motion of the vent ring 26. Alternately, contact between the tapered end 24 of the stem 22 and the venturi nozzle 14 limits downward motion of the vent ring 26. Where the flange 38 is in the exhalation configuration and the flange 38 contacts the vent ring seat 36, that contact may block at least one of the flange openings 39. Referring also to FIG. 3B, in the exhalation configuration, fluid flow from the fluid port 54 causes the flaps 70 to be pushed down onto the flange 38 and the flange openings 39, substantially stopping the free flow of fluid from the patient through the flange openings 39. In this way, because the flange openings 39 are substantially blocked by the flaps 70, the inlet aperture 43 may remain partly or even entirely open, and exhalation air still cannot substantially flow outward through the flange openings 39 and then outward through the inlet aperture 43. In the exhalation configuration, both sides of the diaphragm 40 may be blocked from fluid communication with one other via the flange openings 39. Thus, in the inhalation configuration, the inlet passage 41 and the fluid port 54 are not substantially in fluid communication with one another. The flaps 70 may be thin and lightweight, and generally impermeable to fluid. For example, the flaps 70 may be composed of latex, rubber, silicone or any other suitable substance.

Because the flange openings 39 are closed, exhalation by the patient into the fluid port 54 causes a pressure rise in the chamber 42 above the diaphragm 40. This rise in pressure pushes the flange 38 downward into contact with or into proximity to the vent ring seat 36, to the exhalation position of the flange 38. Where the diaphragm 40 is bistable, the diaphragm 40 may be in one of its two bistable configurations in the exhalation configuration, as seen in FIG. 3A. Utilizing a bistable diaphragm 40 with a stable configuration in the exhalation configuration means the patient need not utilize any breathing force to maintain the exhalation configuration after that exhalation configuration has been reached; as a result, the ventilator 2 may be useful for treating patients with degraded breathing capability. Where the diaphragm 40 is stable in a single configuration, that configuration may be the exhalation configuration as shown in FIG. 3A.

The vent ring 36 includes one or more exhalation windows 78 defined through the side of the vent ring 36. One or more exhalation windows 78 may be located at or near the bottom 27 of the vent ring 36. As the vent ring 36 moves downward, the exhalation windows 78 move downward, below the lower surface 37 of the vent ring seat 36. The central passage 17 is located below the vent ring seat 36, such that when the exhalation windows 78 move below the lower surface 37 of the vent ring seat 36, exhaled air can flow out of the chamber 42 above the diaphragm 40, through the exhalation windows 78 in the vent ring 26, into the central passage 17, and then out of the ventilator 2 through the ambient fluid aperture 4. Thus, in the exhalation configuration, the fluid port 54 and the central passage are in fluid communication with one another.

Operation

The operation of the ventilator 2 now will be described. The fluid port 54 of the ventilator 2 is placed in fluid communication with a respirator, which is attached to a patient. The respirator is provided with compliant sealing surfaces such that a substantially airtight seal is created against the patients face. The patient inhales from and exhales into the respirator. In turn, the respirator is in fluid communication with the airway of the patient. In this way, the fluid port 54 of the ventilator 2 is placed in fluid communication with the patient's airway. According to other embodiments, the fluid port 54 may be any apparatus other than a respirator that places the fluid port 54 in fluid communication with the patient's airway; the use of the respirator to do so is not critical to the invention.

Upon inhalation by the patient, pressure above the diaphragm 40 is reduced compared to ambient air pressure. As a result, the diaphragm 40 flexes upward at and in proximity to its center. Alternately, the diaphragm 40 may be biased upward, at least in part, independently from the patient's inhalation. The upward motion of the diaphragm 40 moves the flange 38 upward, because the flange 38 is connected to the diaphragm 40. Because the flange 38 is part of or connected to the valve 20, that upward motion of the diaphragm 40 causes the valve 20 to move upward. That upward motion of the valve 20 moves the stem 22 upward, thus moving the tapered end 24 of the step out of the venturi opening 16 and away from the venturi nozzle 14. Because the tapered end 24 of the stem 22 has moved out of the venturi opening 16, oxygen is again free to escape from the venturi opening 16. Thus, in this embodiment, oxygen flow out of the venturi opening 16 restarts purely mechanically, powered by inhalation by the patient via the fluid port 54. Oxygen flows out of the venturi opening 16 as long as the tapered end 24 of the stem 22 is spaced apart from the venturi opening 16. This position of the valve 20, in which the stem 22 is spaced apart from the venturi opening 16 and fluid can flow out of the venturi opening 16, is the start flow position of the valve 20.

Oxygen may be supplied to the fluid inlet 6 from any suitable source. According to some embodiments, high pressure oxygen is connected to a pressure regulator, which drops the pressure of that oxygen and outputs lower pressure oxygen to the fluid inlet 6. In one embodiment, the pressure regulator is the GovReg® adjustable flow regulator of Legacy US, Inc, as described in U.S. patent application Ser. No. 15/488,319, filed Apr. 14, 2017 (the "GovReg® document), which is hereby incorporated by reference in its entirety. That U.S. patent application Ser. No. 15/488,319 is a continuation-in-part of U.S. patent application Ser. No. 14/990,673. The U.S. patent application Ser. No. 15/488,319 application also expressly incorporates by reference therein the U.S. patent application Ser. No. 14/990,673 application in paragraph of the U.S. patent application Ser. No. 15/488,319 application as originally filed. Thus, the contents of the U.S. patent application Ser. No. 14/990,673 application are incorporated by reference in the present application and specifically FIGS. 5A, 5B, 7A, 7B, 7C, and 7D and the associated text of U.S. patent application Ser. No. 14/990,673. The use of the GovReg® pressure regulator allows a healthcare worker to set the pressure for a patient and fix that pressure, such that it cannot be changed without the use of an adjustment key that only healthcare workers can change it. This provides additional safety for the patient. Further, multiple ventilators 2 can be connected to the same high pressure oxygen source, and each ventilator 2 can receive a different pressure of oxygen depending on the setting of the GovReg® pressure regulator associated with that ventilator. As described in the "GovReg® document, the pressure regulator may include a housing formed to include a bore within, and a piston movable within that bore, where the piston may include an annular lip adjacent to an end of the piston. A spring may be disposed within the bore, where the spring has two ends, and an adjustment cap may be moveably disposed in the bore, where the adjustment cap may include key slots formed therein. A first end of the spring may be in physical contact with the annular lip, and a second end of the spring may be in physical contact with the adjustment cap. The bore may be defined by a cylindrical wall, and the cylindrical wall may be threaded. The adjustment cap may be threaded as well, such that its threading meshes with the threading of the cylindrical wall. Rotating the adjustment cap in one direction may cause the adjustment cap to compress the spring and increase the output pressure of the pressure regulator, and rotating the adjustment cap in the opposite direction may cause the adjustment cap to decompress the spring and decrease the output pressure of the pressure regulator. The adjustment key may be, or may be detachably connected to, the adjustment cap; the adjustment key may be detachable from the pressure regulator. Thus, in some embodiments, rotation of the adjustment cap allows a healthcare worker to set and fix the pressure for a patient.

Referring now to FIGS. 9-14, a pressure regulator 700 comprises housing 510, piston 760 moveably disposed within housing 510 wherein piston 760 is formed to include an annular lip 762, compression spring 720, and adjustment cap 750. Spring 720 is disposed between annular lip 520 and adjustment cap 750.

Figure 11:
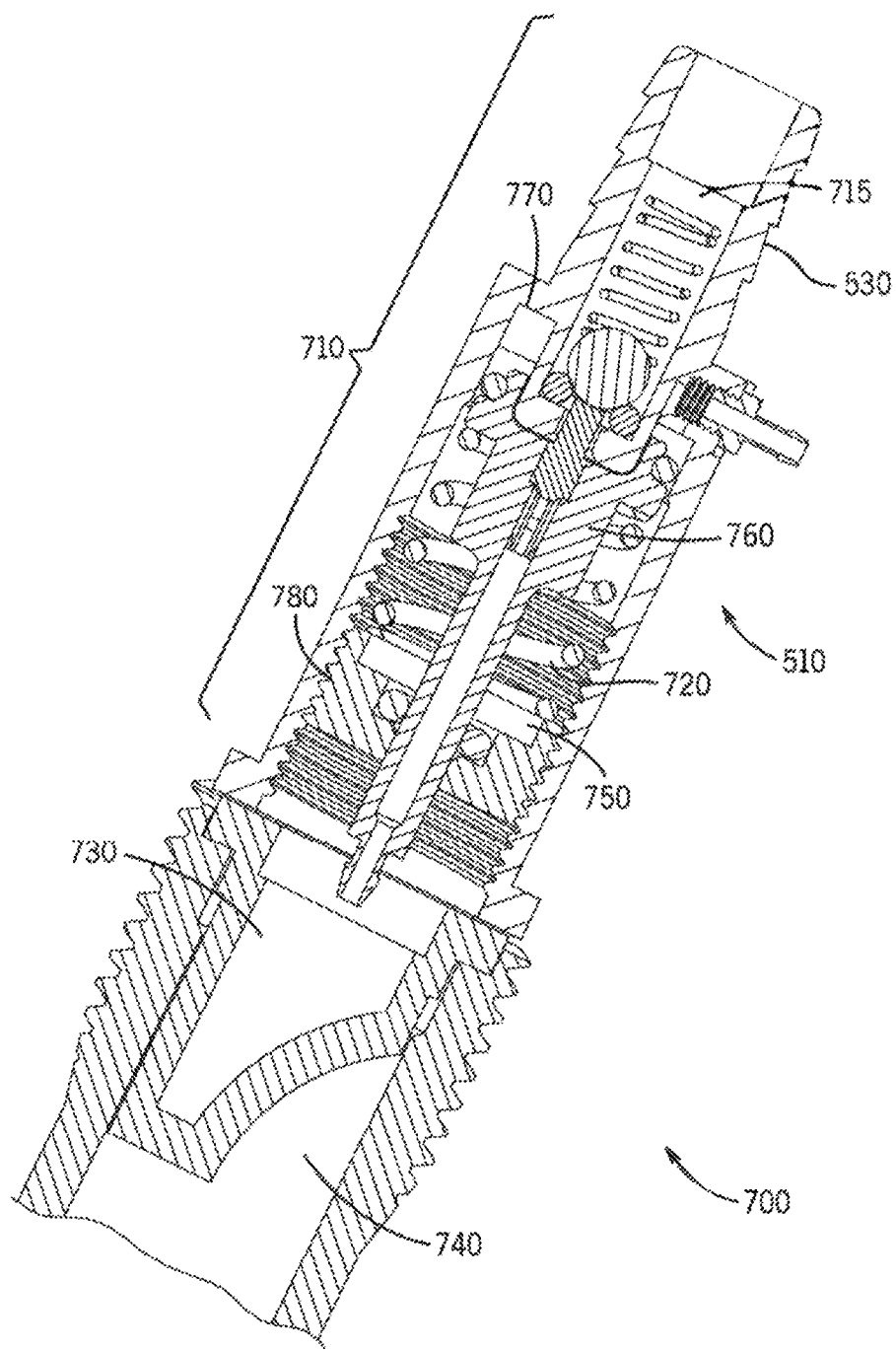
FIG. 11 is a cross-section view of another embodiment of a secondary regulator 700.
Figure 12:
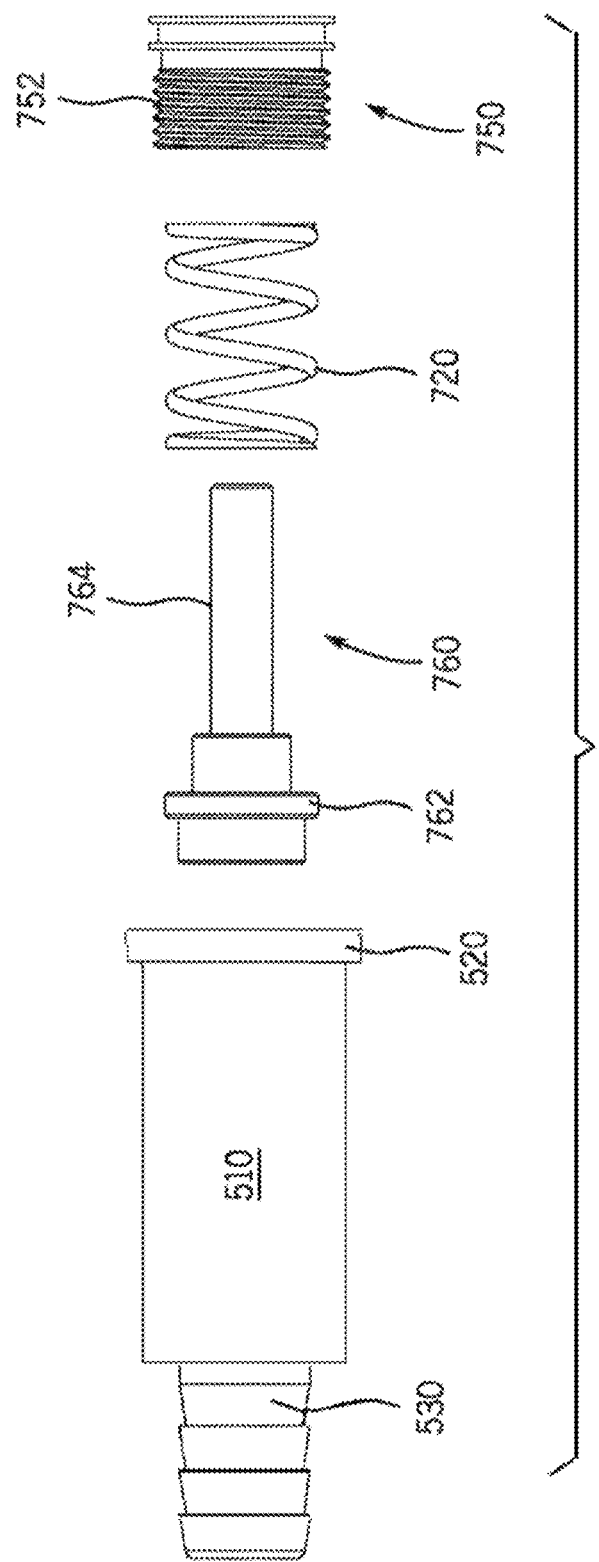
FIG. 12 is an exploded view of the secondary regulator 700.
Figure 13:
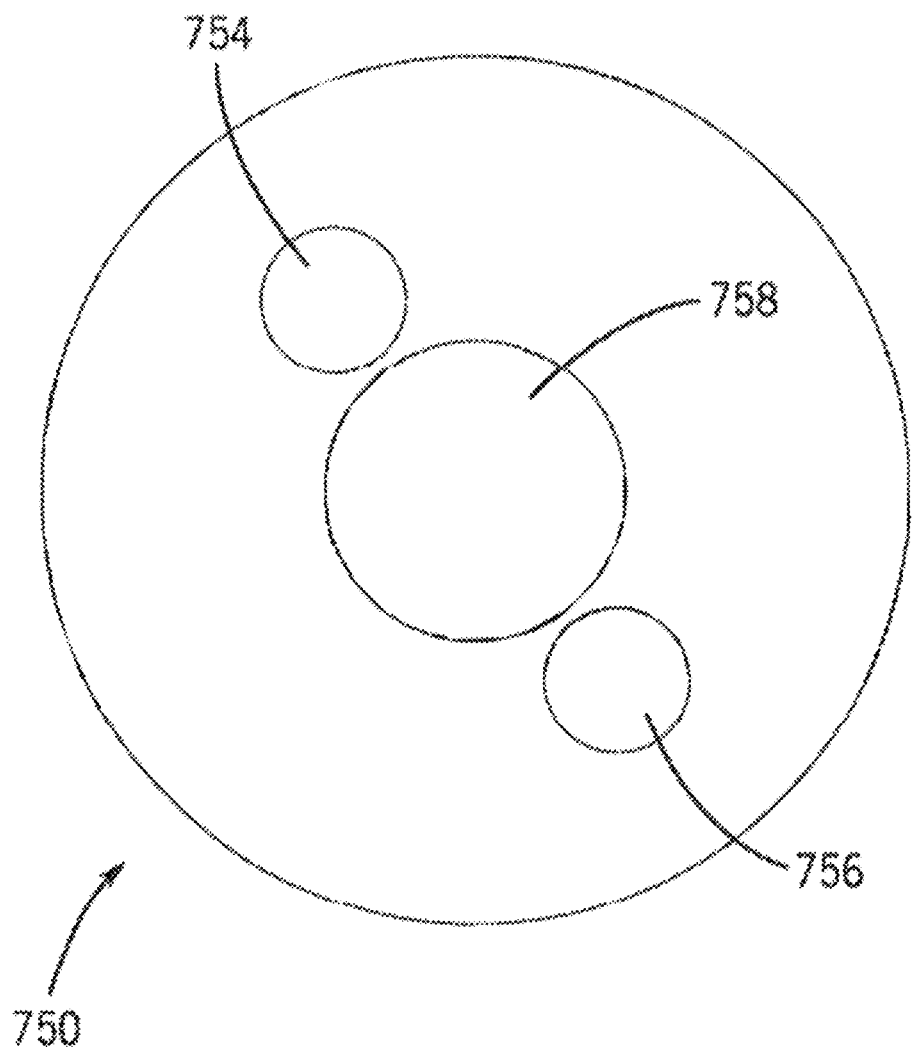
FIG. 13 is a top view of an adjustment cap 750 disposed within the secondary regulator 700.
Figure 14:
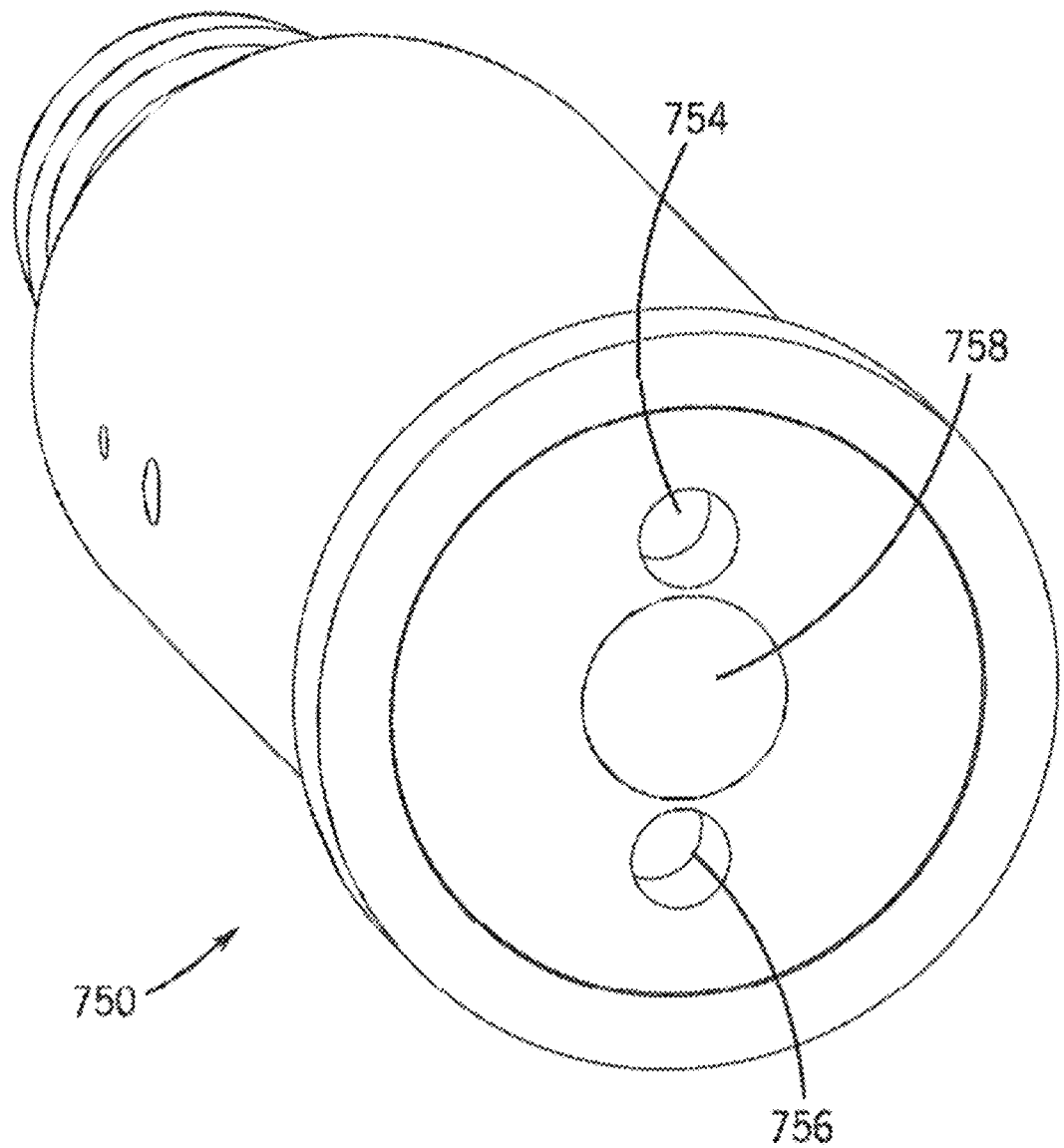
FIG. 14 is a perspective view of the adjustment cap 750.

Referring now to FIGS. 12-14, adjustment cap 750 is formed to include threading adjacent a first end thereof. Threading 752 is configured to mesh with internal threading 780 (FIG. 11).

Compression spring 720 determines the regulated output pressure in portion 740. Rotating adjustment cap in a first direction compresses spring 720, and increases the output pressure in region 740 (FIG. 11) of regulator 700. Rotating adjustment cap in a second and opposite direction decompresses spring 720, and decreases the output pressure in region 740 (FIG. 11) of regulator 700.

Adjustment cap 750 is further formed to include key slots 754 and 756 which extend inwardly in a second end thereof. Adjustment cap 750 is further formed to include an aperture 758 extending therethrough. Shaft 764 of piston 760 passes through aperture 758.

Oxygen travels through the fluid inlet 6 and then the passages 12, then through the venturi nozzle 14 and out of the venturi opening 16. The flow of oxygen outward through the venturi opening 16 entrains ambient air entering the ventilator 2 through the ambient fluid aperture 4, and draws ambient air into the throat 19 of the venturi 10, where oxygen and ambient air are mixed. The venturi nozzle 14 may be sized and configured to create a mixture of ambient air and oxygen that delivers a 26% fraction of inspired oxygen (FiO2) to the patient. This percentage of FiO2 is a recommended oxygen concentration, but other fractions may be used as needed. Accuracy of the fraction of oxygen is not critical, and that fraction may be adjusted by a clinician or other healthcare worker as required. For example, the FiO2 may be adjusted to 40% from 26% as needed by the patient; after the FiO2 has been adjusted to 40%, if the patient needs additional oxygen, the patient may then be removed from the ventilator 2, intubated, and then placed on a currently-known ventilator.

The enriched air travels upward through the central passage 17 to the inlet aperture 43. In the inhalation configuration, the inlet passage 41 is in fluid communication with the central passage 17. As described above, in the inhalation configuration, the vent ring 26 is in an upward position relative to the venturi nozzle 14. In the inhalation configuration, the lowered pressure in the chamber 42 above the diaphragm 40, caused by inhalation by the patient through the fluid port 54, causes the diaphragm 40 to move upward. Inhalation withdraws gas from the chamber 42 above the diaphragm 40, decreasing the pressure and actuating the valve 20 relative to the venturi nozzle 14. The flange 38 may contact the limiter 72, such that the flange 38 does not move higher than the limiter 72 allows. Upward motion of the diaphragm 40 causes the flange 38, which is attached to the flange 38, to move upward. Upward motion of the flange 38 causes the valve 20, of which the flange 38 is a part, to move upward as well. Such upward motion of the valve 20 moves the stem 22 away from the venturi nozzle 14, thereby unblocking the venturi opening 16 and allowing gas to flow outward therefrom. The diaphragm 40 is an example of a pressure force multiplier 40, because the surface area of the diaphragm 40 in combination with the flange openings 39 allow for a small differential change in pressure at the fluid port 54 to actuate the valve 20 between closed and open states.

As described above, in the inhalation configuration, the inlet aperture 43 is open, placing the central passage 17 in fluid communication with the inlet passage 41, and both sides of the diaphragm 40 are thus in fluid communication with one other via the flange openings 39; as a result, those flange openings 39 place the inlet passage 41 and the fluid port 54 in fluid communication in the inhalation configuration. Thus, in the inhalation configuration, the central passage 17, the inlet passage 41, and the fluid port 54 are in fluid communication with one another, such that enriched air flows freely from the venturi nozzle 14 to the fluid port 54, and then to the patient.

The patient inhales normally, or as normally as possible. The ventilator 2 is a simple, single-mode ventilator that does not deliver a specific, limited or preselected volume or flow rate of air to the patient; instead, it delivers air at a volume and flow rate that are controlled solely by the patient's own inhalation. Further, the ventilator 2 only delivers enriched air to the patient during the patient's inhalation, and momentarily afterward. As opposed to continuous positive airway pressure (CPAP) or positive end-expiratory pressure (PEEP) ventilation, enriched air is only supplied to the patient during inhalation. In this way, the ventilator 2 does not apply pressure to the patient's nose or mouth while the patient is trying to exhale, and oxygen is not wasted by applying it to the patient's nose or mouth while the patient is actively exhaling.

After inhalation, the patient then exhales. Upon exhalation by the patient, pressure above the diaphragm 40 is increased compared to ambient air pressure. Referring also to FIG. 3B, in the exhalation configuration, fluid flow into the chamber 42 from the fluid port 54 causes the flaps 70 to be pushed down onto the flange 38 and the flange openings 39, substantially stopping the free flow of fluid from the patient through the flange openings 39. In this way, because the flange openings 39 are substantially blocked by the flaps 70, the inlet aperture 43 may remain partly or even entirely open, and exhalation air still cannot substantially flow outward through the flange openings 39 and then outward through the inlet aperture 43. In the exhalation configuration, both sides of the diaphragm 40 may be blocked from fluid communication with one other via the flange openings 39. Thus, in the exhalation configuration, the inlet passage 41 and the fluid port 54 are not substantially in fluid communication with one another.

Because the flange openings 39 are closed, exhalation by the patient into the fluid port 54 causes a pressure rise in the chamber 42 above the diaphragm 40. That is, exhalation forces gas into the chamber 42 above the diaphragm 40, increasing the pressure and actuating the valve 20 relative to the venturi nozzle 14. This rise in pressure pushes the flange 38 downward into contact with or into proximity to the vent ring seat 36, to the exhalation position of the flange 38. Because the flange 38 is part of or connected to the valve 20, that downward motion of the diaphragm 40 causes the valve 20 to move downward. That downward motion of the valve 20 moves the stem 22 downward, thus moving the tapered end 24 of the step toward from the venturi nozzle 14 and into the venturi opening 16. Because the tapered end 24 of the stem 22 has moved into the venturi opening 16, oxygen is substantially restricted from escaping from the venturi opening 16. Thus, oxygen flow out of the venturi opening 16 stops purely mechanically, powered by exhalation by the patient through the fluid port 54. Oxygen is substantially restricted from escaping out of the venturi opening 16 as long as the tapered end 24 of the stem 22 plugs the venturi opening 16. This position of the valve 20, in which the stem 22 plugs the venturi opening 16 and fluid is substantially restricted from flowing out of the venturi opening 16, is the stop flow position of the valve 20.

As the flange 38 and the vent ring 36 moves downward, the exhalation windows 78 move downward, below the lower surface 37 of the vent ring seat 36. The central passage 17 is located below the vent ring seat 36, such that when the exhalation windows 78 move below the lower surface 37 of the vent ring seat 36, exhaled air can flow out of the chamber 42 above the diaphragm 40, through the exhalation windows 78 in the vent ring 26, into the central passage 17, and then out of the ventilator 2 through the ambient fluid aperture 4. Thus, in the exhalation configuration, the fluid port 54 and the central passage are in fluid communication with one another. The exhaled breath then travels through the central passage 17 and out of the ventilator 2 through the ambient fluid aperture 4. When the patient then inhales again, the cycle of operation described above repeats again.

Because the ventilator 2 does not require electrical power to operate according to some embodiments, its form factor may be comparatively small, such that the ventilator 2 may be portable. The ventilator 2 may be carried on the user's back by a strap or straps like a backpack; may be carried by a strap over the shoulder like a purse, may be wheeled and able to be pulled behind a user like luggage, or may be otherwise portable. The portability of the ventilator 2 also allows the user to take the ventilator 2 home. Home use of the ventilator 2 may be advantageous for patients who have been diagnosed with COVID-19 or other respiratory disease, but whose symptoms have not advanced to the level of seriousness of ARDS such that they require intubated ventilation. In this way, during a pandemic such as the 2020 COVID-19 pandemic, patients who are infected with a virus that causes respiratory problems can be treated safely at home, without consuming hospital beds and other hospital resources needed for patients who are significantly sicker and closer to death.

Because the ventilator 2 is small and portable and non-invasive, and simply provides enriched air with a higher oxygen concentration to a user, the ventilator 2 may find use in other applications. As one example, the ventilator 2 may be useful in the treatment of asthma and/or seasonal allergies. The user wears a respirator as described above, and the ventilator 2 works substantially as described above; a user utilizes it as a portable device. The increased oxygen concentration delivered by the ventilator 2 may be beneficial for asthma sufferers, and the filter(s) 56 may be useful for removing pollen and other allergens from the air before they can be inhaled by the user, thereby improving symptoms experienced by those who suffer from seasonal allergies. As another example, in extremely polluted cities, the air may be unhealthy to breathe. By utilizing the ventilator 2 as a portable device, clean oxygen is delivered to the user at a higher than ambient concentration, and the filter(s) 56 may be useful for removing particulates and/or other pollutants from the ambient air prior to inhalation by the user.

The ventilator 2 described above with regard to FIGS. 1-4 may find particular use in the treatment of patients infected with the COVID-19 virus, especially prior to their development of ARDS. It is believed that treatment of such patients utilizing the ventilator 2 may prevent a portion of such patients from developing ARDS. It is expected that the ventilator 2 would be classified as a Class II medical device by the FDA and would thus require approval by the FDA for use in treating patients. While the regulatory path for approval by the FDA of the ventilator 2 is unknown as of the filing date of this document, it is expected that for use as a medical device, the ventilator 2 would require at least one of an Investigational Device Exemption (IDE), an Emergency Use Authorization (EUA), and a Premarket Approval (PMA). The independent claims as filed are believed to cover embodiments of the ventilator 2 that would be subject to an applicable FDA approval.

However, the ventilator 2 is not limited to use the treatment of patients infected with the COVID-19 virus; the ventilator 2 may be used to treat patients suffering from other ailments. Further, the ventilator 2 may find use in fields other than healthcare in which control of fluid flow is desired, and need not be used in conjunction with a human being in such fields. Further, the ventilator 2 is described above as having components in fluid communication with one another and with one or more external attachments, such as a respirator. Where the ventilator 2 is utilized to treat a patient, the fluid of that fluid communication is a gas. However, where the ventilator 2 is utilized in other applications, the fluid may be a liquid, or a mixture of liquid and gas.

While the embodiment of the invention described above arose in an endeavor to facilitate treatment of respiratory conditions associated with COVID-19, it will be understood that the fluid mixer 2 has various other uses and applications in other fields, which include but are not limited to the following. As one example, in Formula 1 racing and other racing applications, the fluid mixer 2 may be used to pre-spin turbochargers by detecting pressure changes, to actuate cam timing changes based on pressure, to actuate opening of fuel/air and exhaust ports based on pressure, to actuate aerodynamic downforce adjustment based on pressure conditions at a sample site, to actuate fuel system pressure adjustment, and to regulate temperature in fluid. As another example, in standard automotive usage, the fluid mixer 2 may be used to actuate turbocharger pre-spin, to actuate cam timing changes, to actuate opening of fuel/air and exhaust ports based on pressure, to actuate fuel system pressure adjustment, and to regulate temperature in fluid As another example, in indoor agriculture applications, the fluid mixer 2 may be used to actuate gas mixing based on pressure, and/or to actuate a pressure communication system. In such applications, the fluid that flows through the fluid mixer 2 may be a liquid, a gas, or both.

Referring also to FIGS. 5-8, another embodiment of the fluid mixer 2 is shown. Such an embodiment may be described as a "reverse configuration." Such an embodiment may be useful for automotive or racing applications, although the fluid mixer 2 of FIGS. 5-8 is not limited to use in such applications. Any embodiment may be used with liquid, gas or both as the fluid. As seen in FIGS. 5-8, the valve 20 is in a start flow position, in which fluid can enter the fluid mixer 2 through the fluid inlet 6. The valve 20 may include a tapered end 24 or other suitably-shaped end, which is received in a bore 80. A spring 82 may be received in the bore 80 as well. One end of the spring 82 may engage an end of the bore 80, and the other end of the spring 82 may engage an end of the valve 20. The other end 84 of the valve 20 may be substantially cylindrical, or have any other suitable shape. The end 84 of the valve 20 is received in a pipe 86 through which fluid can flow. The bore 80 is substantially hollow, such that fluid flows from the fluid inlet 6 through the bore 80 when the valve 20 is in the start flow position, and then into one or more passages 12. As described in the with regard to the previous embodiment, fluid flows out of the one or more passages 12 through the venturi opening 16 in the venturi nozzle 14.

In this embodiment, the pressure force multiplier 40 is substantially sealed to the chamber 42 to form a sealed plenum 88. Unlike the previous embodiment, fluid does not substantially cross the pressure force multiplier 40. When fluid flows into the fluid mixer 2 through the fluid port 54, that fluid flows toward the ambient fluid aperture 4 through the central passage 17. The chamber 42 is open to the central passage 17 through a chamber opening 90. The chamber opening 90 may have any suitable shape and size. The chamber opening 90 allows for fluid communication between the chamber 42 and the central passage 17. When fluid is forced into the central passage 17 through the fluid port 54, pressure in the central passage 17 increases. Pressure in the chamber 42 on the side of the pressure force multiplier 40 opposite the plenum 88 increases as well due to fluid communication through the chamber opening 90. Because the pressure force multiplier 40 is substantially sealed to the chamber 42 and fluid substantially cannot cross the pressure force multiplier 40, pressure on the pressure force multiplier 40 increases, causing the pressure force multiplier 40 to move and thus decrease the volume of the plenum 88, increasing the pressure in the plenum 88 as well. That increased pressure in the plenum 88 is transmitted through the pipe 86 to the end 84 of the valve 20. That pressure drives the end 84 of the valve 20 toward the spring 82 in the bore 80, opening the valve 20 to the start flow position. In the start flow position, the tapered end 24 of the valve 20, or otherwise-shaped end of the valve 20, moves apart from the aperture 92, allowing fluid to flow through the aperture 92 into the bore 80. It may be that the volume of the plenum 88, along with the volume of the pipe 86, remains substantially constant during this process. This is because the end 84 of the valve 20 in the bore 80 is movable, such that any momentary increase in pressure in and decrease in volume of the plenum 88 may be substantially matched by movement of the end 84 of the valve 20. In this way, a substantially fixed volume may be defined on one side of the pressure force multiplier 40.

When fluid flows into the fluid mixer 2 through the ambient fluid aperture 4, that fluid flows toward the fluid port 54 through the central passage 17. When fluid is withdrawn through the fluid port 54, pressure in the central passage 17 decreases. Pressure in the chamber 42 on the side of the pressure force multiplier 40 opposite the plenum 88 decreases as well due to fluid communication through the chamber opening 90. Because the pressure force multiplier 40 is substantially sealed to the chamber 42 and fluid substantially cannot cross the pressure force multiplier 40, pressure on the pressure force multiplier 40 decreases, causing the pressure force multiplier 40 to move and thus increase the volume of the plenum 88, decreasing the pressure in the plenum 88 as well. That decreased pressure in the plenum 88 is transmitted through the pipe 86 to the end 84 of the valve 20. The pressure applied to the end 84 of the valve 20 in the bore 80 decreases, allowing the spring 82 to push the end 84 of the valve 20 further into the pipe 86. The spring 82 may be a compression spring that biases the valve 20 toward the stop flow positions; motion of the valve 20 toward the pipe 86 closes the valve 20 to the stop flow position. In the stop flow position, the tapered end 24 of the valve 20, or otherwise-shaped end of the valve 20, moves toward and substantially blocks the aperture 92, substantially stopping fluid flow through the aperture 92 into the bore 80. According to some embodiments, the start flow position of the valve 20 is also the active flow position, allowing fluid to flow while the valve is in the start flow position. Alternately, the valve 20 may be positioned in a different active flow position, between the start flow and stop flow positions; such an active flow position may be determined by the level or duration of force with which fluid is forced into the fluid port 54 or withdrawn from the fluid port 54.

Referring now to FIGS. 15A-15G, there is shown various views of an attachment device generally indicated 1501. The attachment device 1501 comprising a body 1503 having a fluid outlet port 1505 and, in this embodiment, two fluid inlet ports 1507. It will be understood that in other embodiments, the attachment device may have more than two fluid inlet ports. Each fluid inlet port 1507 is connectable to a respective fluid source (not shown). Each fluid inlet port 1507 is in fluid communication with the fluid outlet port 1505. A fluid may thus travel into the attachment device 1501 via one of the fluid inlet ports 1507 and out via the fluid outlet port 1505, when allowed by the attachment device mechanism(s) 1509. Each fluid inlet port 1507 comprises an attachment device mechanism 1509 for selectively starting and stopping the flow of fluid from the respective fluid source (not shown) to the fluid outlet port 1505.

In this embodiment, the body 1503 is in the form of a short hollow cylinder 1511 with a hollow triangular prism 1513 sat on top thereof (shaped much like the roof of a typical house). Of course, it will be appreciated that the body can take any suitable shape. In this embodiment, each fluid inlet port 1507 comprises an arm 1515 extending from the body 1513. More specifically, each arm 1515 extends generally diagonally upwardly which is extending orthogonally from an angled face 1517 of the hollow triangular prism 1513 such that they define an angle of approximately 120 degrees between one another, and approximately 120 degrees with respect to the longitudinal axis of the short hollow cylinder 1511. Each arm 1515 is shaped as an elongate hollow cylinder 1519 having an access hole 1521 at one end 1523 for receiving fluid from a respective fluid source (not shown). Towards the other end 1525 of the elongate hollow cylinder 1519 there are provided a pair of apertures 1527, which in this embodiment are in the shape of rectangular holes that are cut out of the wall of each of the elongate hollow cylinders 1519. It will be appreciated that in other embodiments, the fluid inlet ports 1507 may each comprise more than two apertures.

Figure 15A:
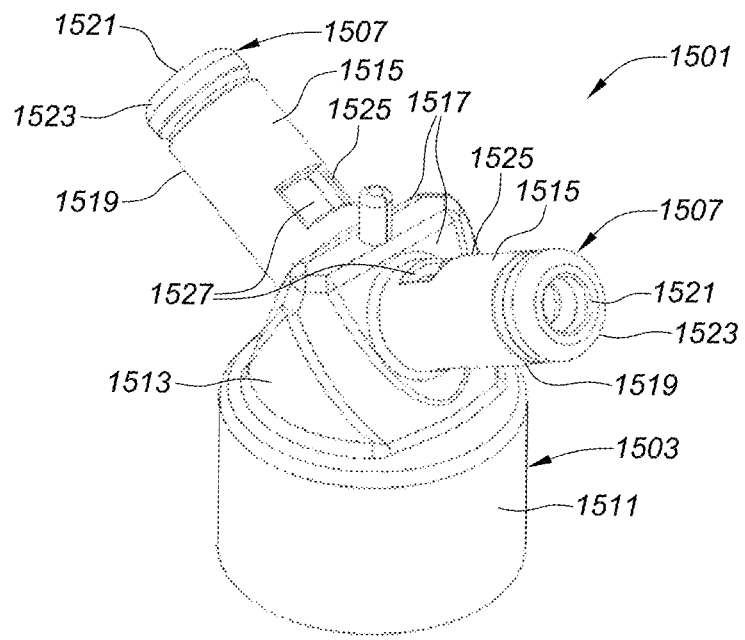
FIG. 15A is an upper perspective view of an attachment device formed according to an embodiment of the invention in which there are two fluid inlet ports.
Figure 15B:
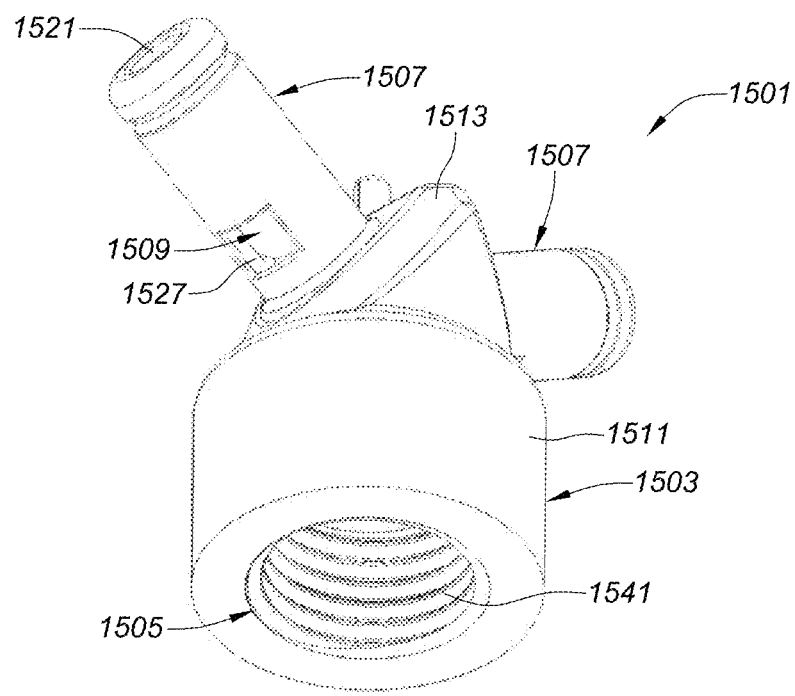
FIG. 15B is a lower perspective view of the attachment device of FIG. 15A.
Figure 15C:
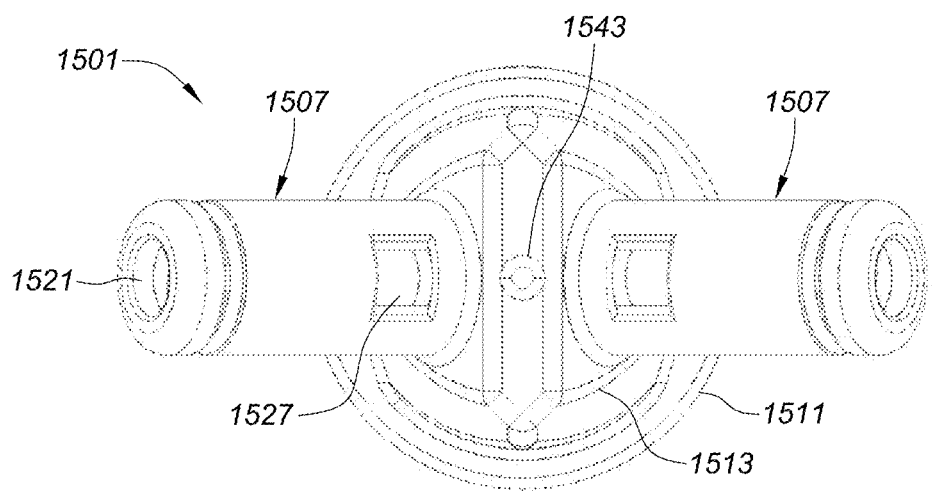
FIG. 15C is a plan view of the attachment device of FIG. 15A.
Figure 15D:
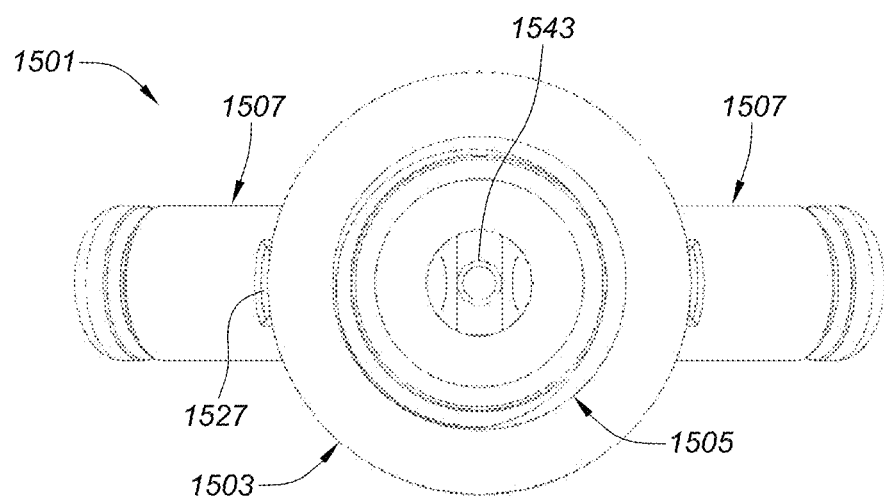
FIG. 15D is a bottom view of the attachment device of FIG. 15A.
Figure 15E:
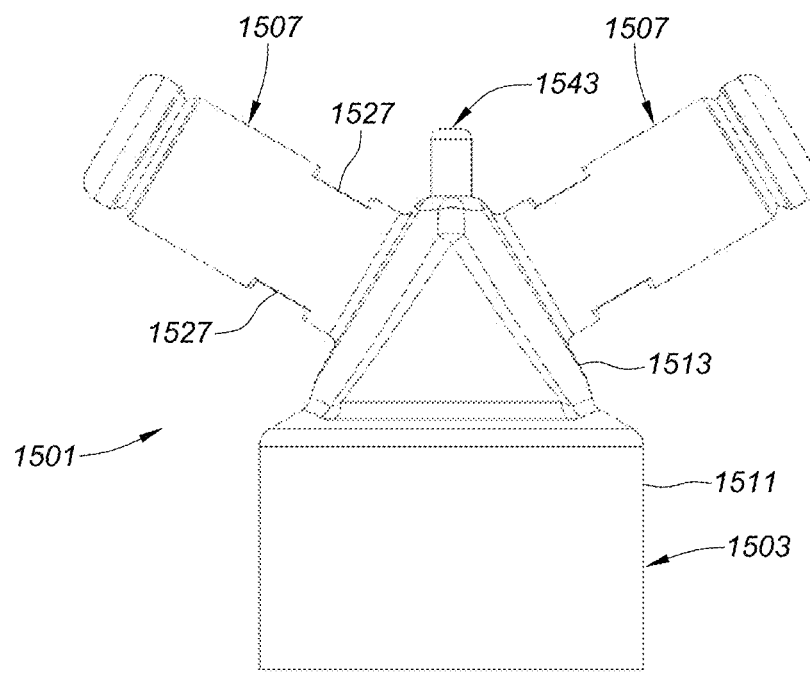
FIG. 15E is a side view of the attachment device of FIG. 15A.
Figure 15F:
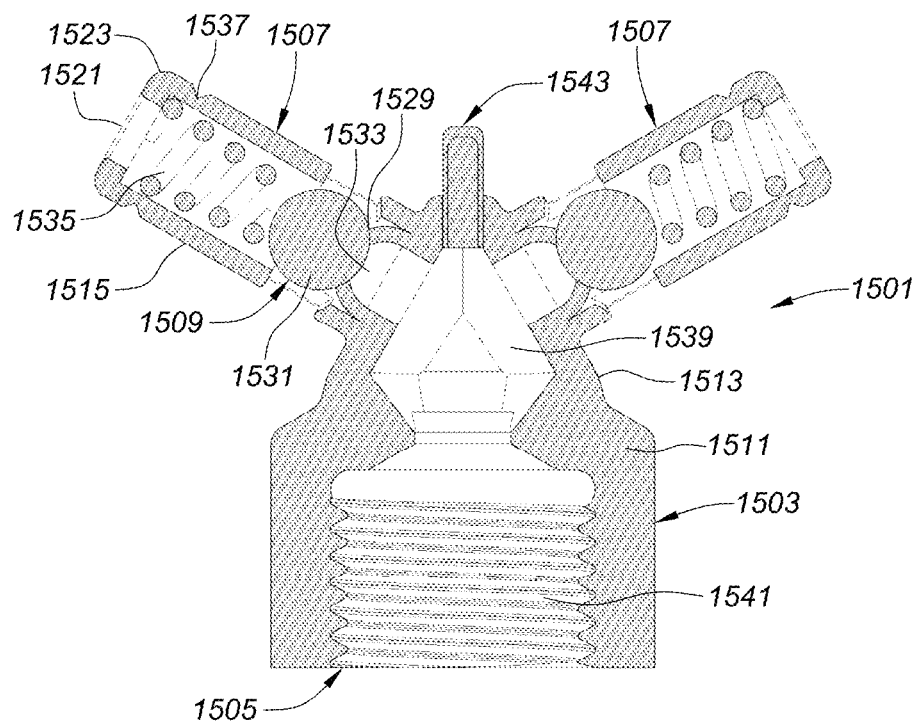
FIG. 15F is a side cutaway view of the attachment device of FIG. 15A.
Figure 15G:
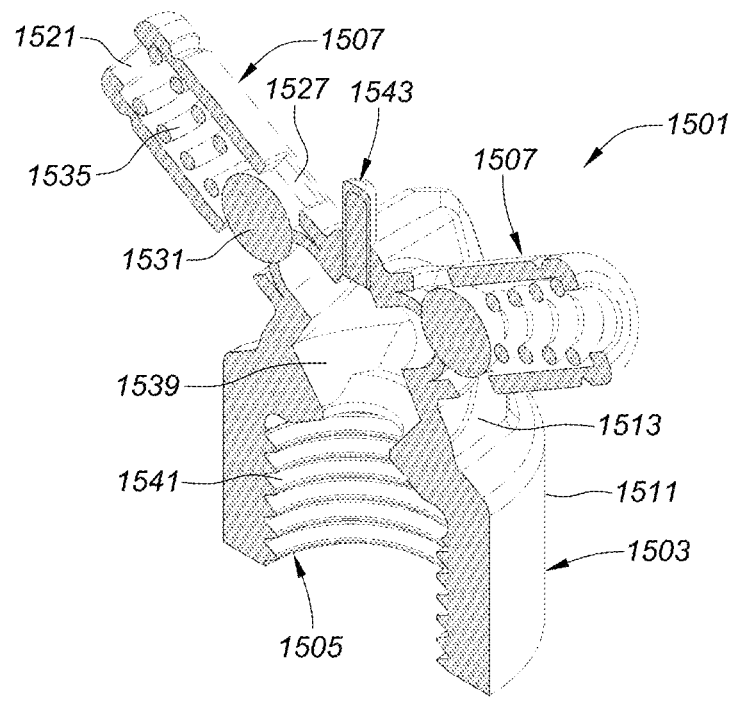
FIG. 15G is an upper perspective cutaway view of the attachment device of FIG. 15A.

As best seen in FIG. 15F, there is shown that each fluid inlet port 1507 comprises an attachment device mechanism 1509 for selectively starting and stopping the flow of fluid from the respective fluid source (not shown) to the fluid outlet port 1505. The attachment device mechanism 1509 comprises a valve 1529 having a ball 1531 moveable between an open valve position (shown in later embodiments) and closed valve position (as shown in FIG. 15F). In the closed valve position, each valve orifice 1533 is sealed shut by each ball 1529 housed within each fluid inlet port 1507. The attachment device mechanism 1509 also comprises a spring 1535 housed within each fluid inlet port 1507. More particularly, the valve 1529 comprises the spring 1535 for biasing the ball 1531 to the closed valve position (as shown in FIG. 15F).

Each arm 1515 comprises a groove 1537 about its periphery. In this embodiment, the groove 1537 is positioned towards the end 1523 closest to the access hole 1521. As can also be seen in FIG. 15F, the body 1503 comprises a hollow chamber 1539 that allows fluid communication between the hollow triangular prism 1513 and the short hollow cylinder 1511. During operation, when the valve 1529 is open, for example, fluid from a fluid source (not shown) may enter the access hole 1521, through/around the spring 1535, around the ball 1531, through the valve orifice 1533, into the hollow chamber 1539, and exit via the fluid outlet port 1505. In this embodiment, the body 1503 comprises internal threading 1541 at the fluid outlet port 1505 that is connectable to another device, such as a pressure regulator (not shown in FIG. 15F) having external threading (not shown in FIG. 15F).

As can also be seen in FIG. 15F, the attachment device 1501 comprises a bleeder valve 1543 that comprises a fluid pressure indicator which aids an operator in ensuring that the correct/minimum fluid pressure/flow is present before disengaging a fluid source (not shown) from a fluid inlet port 1507, thereby maintaining the fluid pressure/flow of fluid entering and exiting the attachment device 1501 via the fluid inlet ports 1507 and fluid outlet port 1505, respectively.

Referring now to FIGS. 16A-16G, there is shown various views of an attachment device generally indicated 1601 formed according to another embodiment of the invention. The embodiment of FIGS. 16A-16G is the same as FIGS. 15A-15G (like numbers denote like features), except the attachment device of FIGS. 16A-16G comprises three fluid inlet ports 1607 instead of two fluid inlet ports 1507 (as shown in FIGS. 15A-15G). The hollow triangular prism 1513 of FIGS. 15A-15G is also replaced with a hollow pyramid 1613 having three angled faces 1617 to accommodate for the additional fluid inlet port 1607. The three fluid inlet ports 1607 are angled and arranged in the shape of a tripod.

The attachment device 1601 comprising a body 1603 having a fluid outlet port 1605. Each fluid inlet port 1607 is connectable to a respective fluid source (not shown). Each fluid inlet port 1607 is in fluid communication with the fluid outlet port 1605. A fluid may thus travel into the attachment device 1601 via one of the fluid inlet ports 1607 and out via the fluid outlet port 1605, when allowed by the attachment device mechanism(s) 1609. Each fluid inlet port 1607 comprises an attachment device mechanism 1609 for selectively starting and stopping the flow of fluid from the respective fluid source (not shown) to the fluid outlet port 1605.

In this embodiment, each fluid inlet port 1607 comprises an access hole 1621 for receiving fluid from a respective fluid source (not shown), and there are also provided a pair of apertures 1627.

Figure 16A:
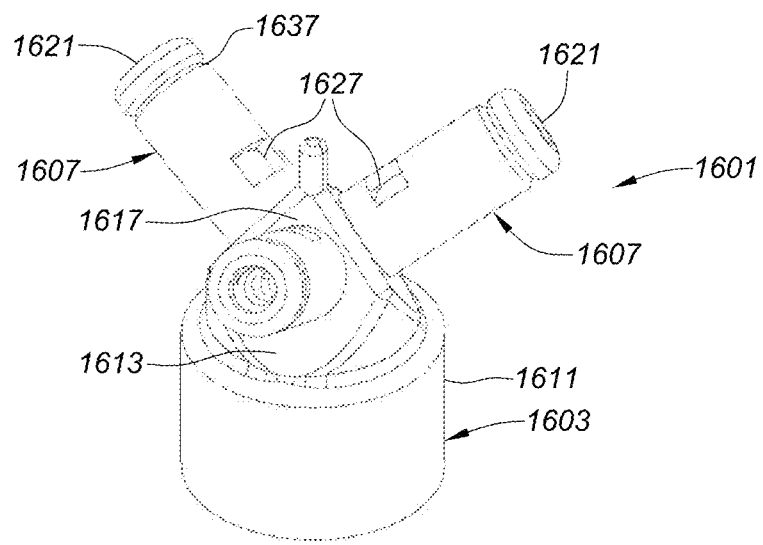
FIG. 16A is an upper perspective view of an attachment device formed according to another embodiment of the invention in which there are three fluid inlet ports.
Figure 16B:
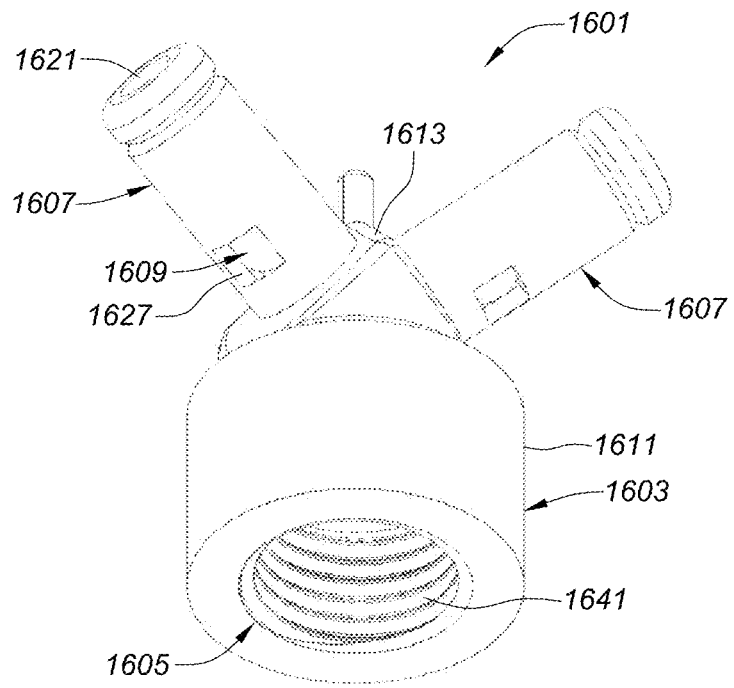
FIG. 16B is a lower perspective view of the attachment device of FIG. 16A.
Figure 16C:
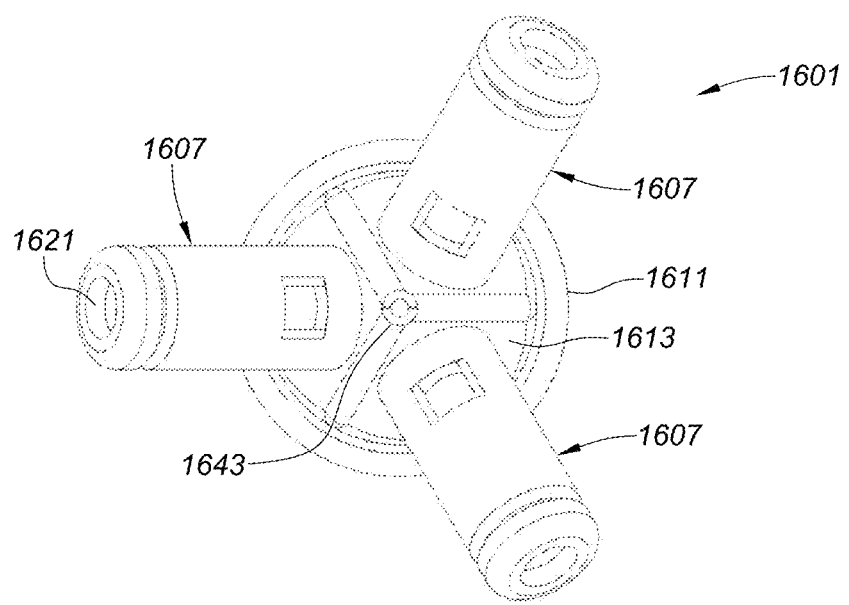
FIG. 16C is a plan view of the attachment device of FIG. 16A.
Figure 16D:
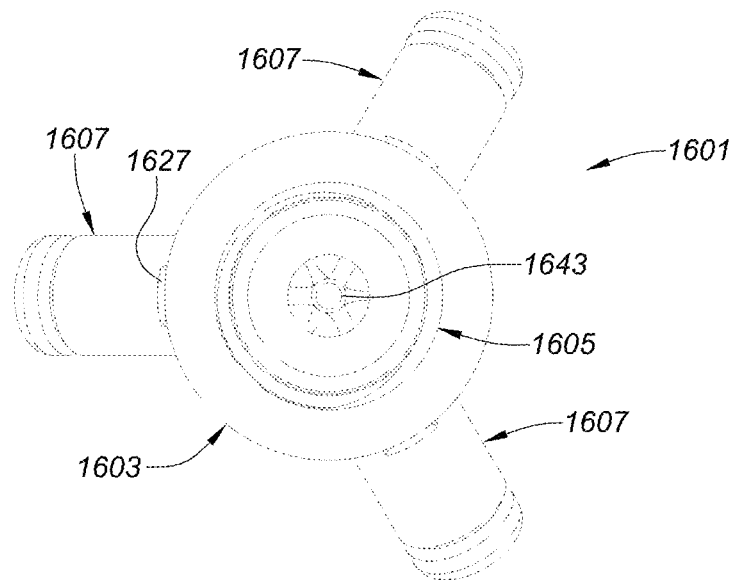
FIG. 16D is a bottom view of the attachment device of FIG. 16A.
Figure 16E:
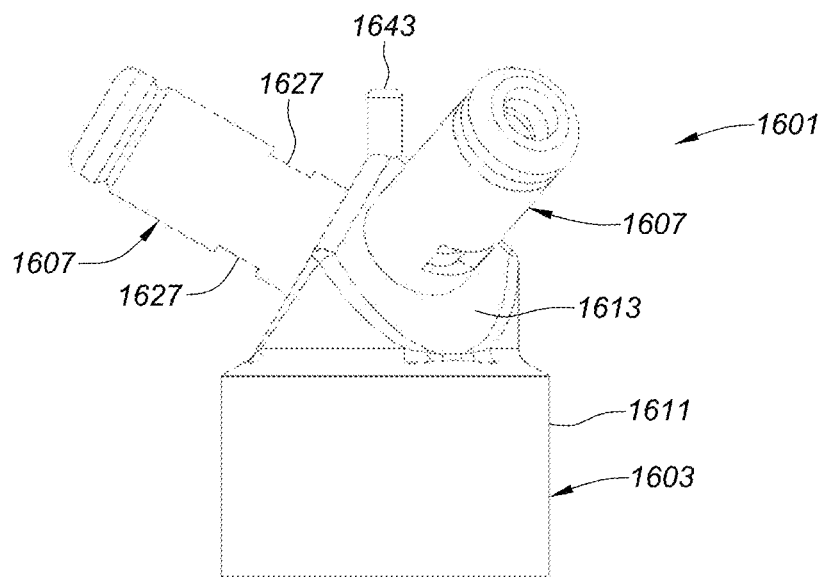
FIG. 16E is a side view of the attachment device of FIG. 16A.
Figure 16F:
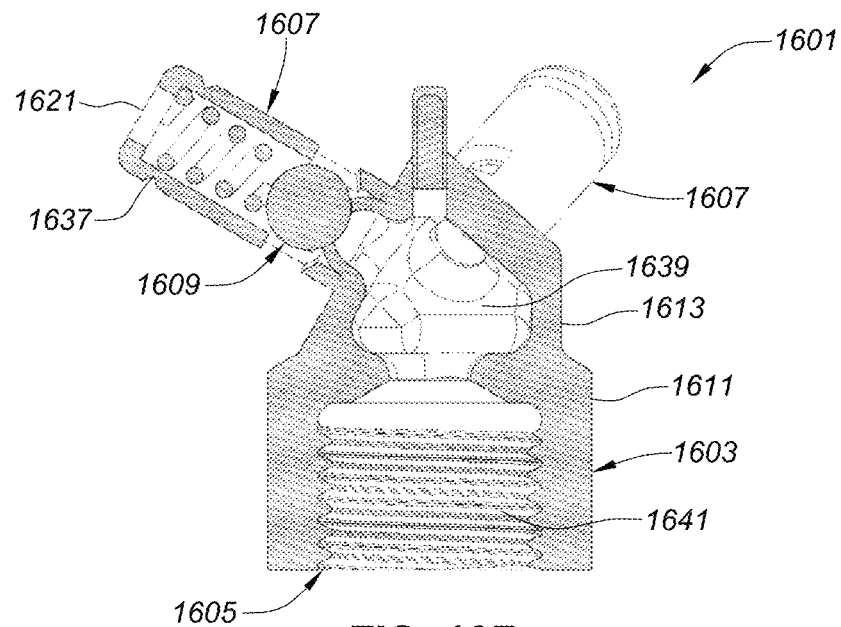
FIG. 16F is a side cutaway view of the attachment device of FIG. 16A.
Figure 16G:
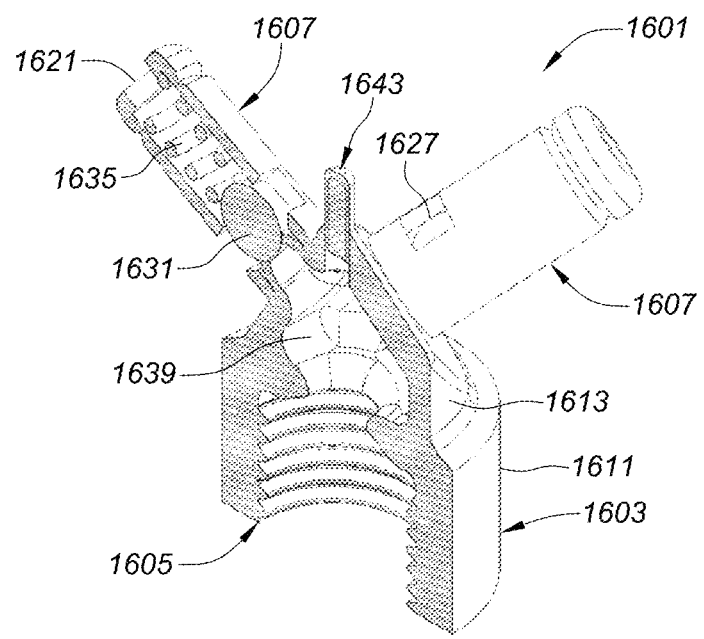
FIG. 16G is an upper perspective cutaway view of the attachment device of FIG. 16A.

As best seen in FIG. 16F, there is shown that each fluid inlet port 1607 comprises an attachment device mechanism 1609 for selectively starting and stopping the flow of fluid from the respective fluid source (not shown) to the fluid outlet port 1605. The attachment device mechanism 1609 comprises a valve having a ball 1631 moveable between an open valve position (shown in later embodiments) and closed valve position (as shown in FIG. 16F). The attachment device mechanism 1609 also comprises a spring 1635 housed within each fluid inlet port 1607. More particularly, the valve comprises the spring 1635 for biasing the ball 1631 to the closed valve position (as shown in FIG. 16F).

Each arm of each fluid inlet port 1607 comprises a groove 1637 about its periphery. As can also be seen in FIG. 16F, the body 1603 comprises a hollow chamber 1639 that allows fluid communication between the hollow pyramid 1613 and the short hollow cylinder 1611. During operation, when the valve is open, for example, fluid from a fluid source (not shown) may enter the access hole 1621, through/around the spring 1635, around the ball 1631, through the valve orifice, into the hollow chamber 1639, and exit via the fluid outlet port 1605. In this embodiment, the body 1603 comprises internal threading 1641 at the fluid outlet port 1605 that is connectable to another device, such as a pressure regulator (not shown in FIG. 16F) having external threading (not shown in FIG. 16F).

As can also be seen in FIG. 16F, the attachment device 1601 comprises a bleeder valve 1643 that comprises a fluid pressure indicator which aids an operator in ensuring that the correct/minimum fluid pressure/flow is present before disengaging a fluid source (not shown) from a fluid inlet port 1607, thereby maintaining the fluid pressure/flow of fluid entering and exiting the attachment device 1601 via the fluid inlet ports 1607 and fluid outlet port 1605, respectively.

Referring now to FIGS. 17A-17G, there is shown various views of an attachment device generally indicated 1701 formed according to another embodiment of the invention. The embodiment of FIGS. 17A-17G is the same as FIGS. 15A-15G (like numbers denote like features), except the attachment device of FIGS. 17A-17G comprises four fluid inlet ports 1707 instead of two fluid inlet ports 1507 (as shown in FIGS. 15A-15G). The hollow triangular prism 1513 of FIGS. 15A-15G is also replaced with a hollow cube 1713 having four faces 1717 to accommodate for the additional two fluid inlet ports 1707. The four fluid inlet ports 1707 lie in the same plane and are arranged in the shape of a cross.

The attachment device 1701 comprising a body 1703 having a fluid outlet port 1705. Each fluid inlet port 1707 is connectable to a respective fluid source (not shown). Each fluid inlet port 1707 is in fluid communication with the fluid outlet port 1705. A fluid may thus travel into the attachment device 1701 via one of the fluid inlet ports 1707 and out via the fluid outlet port 1705, when allowed by the attachment device mechanism(s) 1709. Each fluid inlet port 1707 comprises an attachment device mechanism 1709 for selectively starting and stopping the flow of fluid from the respective fluid source (not shown) to the fluid outlet port 1705.

In this embodiment, each fluid inlet port 1707 comprises an access hole 1721 for receiving fluid from a respective fluid source (not shown), and there are also provided a pair of apertures 1727.

Figure 17A:
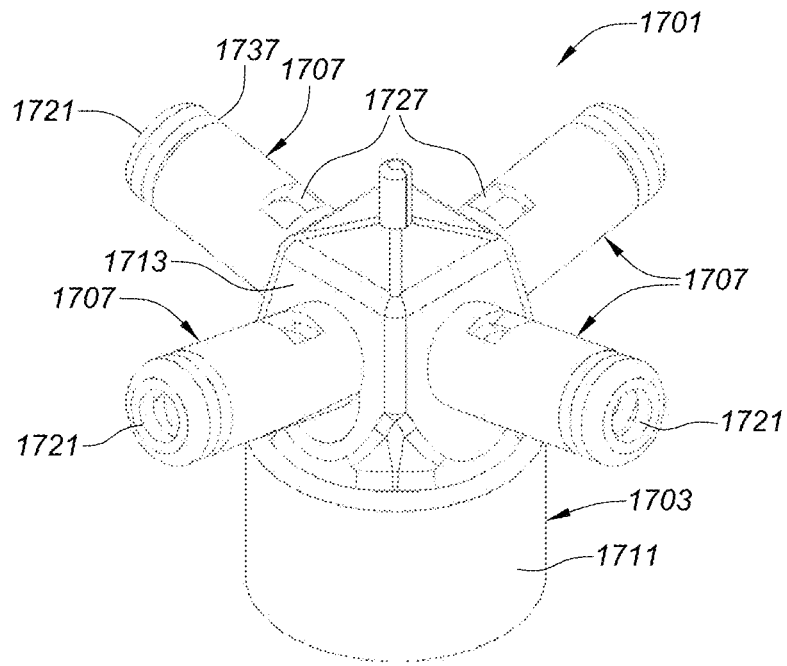
FIG. 17A is an upper perspective view of an attachment device formed according to another embodiment of the invention in which there are four fluid inlet ports.
Figure 17B:
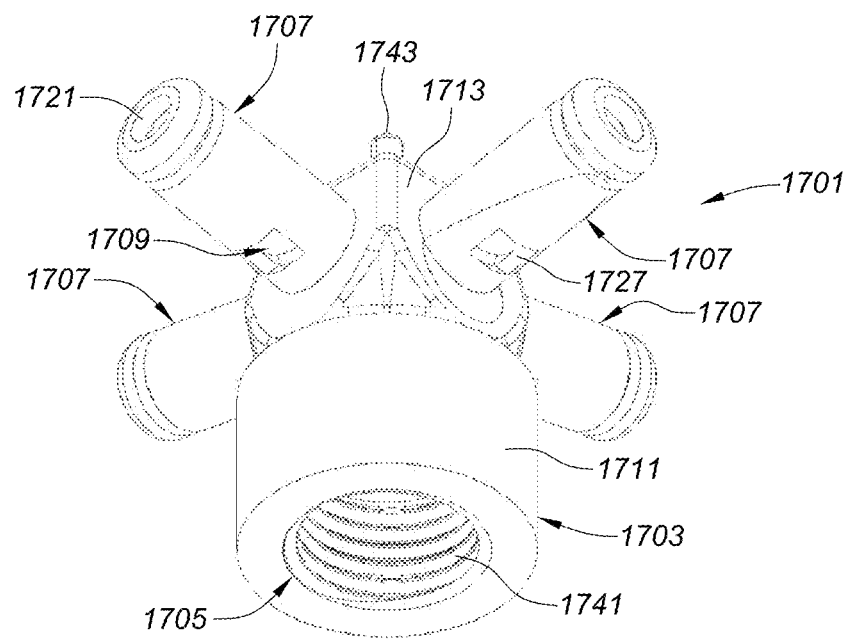
FIG. 17B is a lower perspective view of the attachment device of FIG. 17A.
Figure 17C:
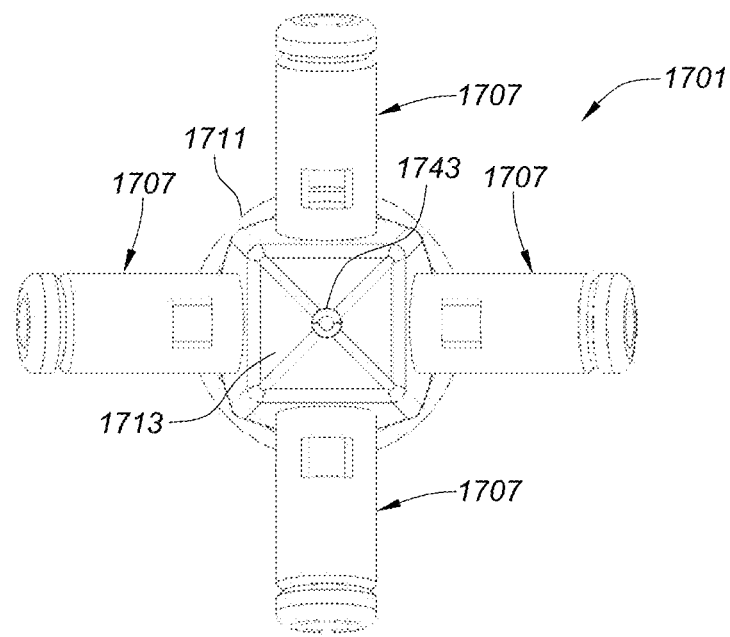
FIG. 17C is a plan view of the attachment device of FIG. 17A.
Figure 17D:
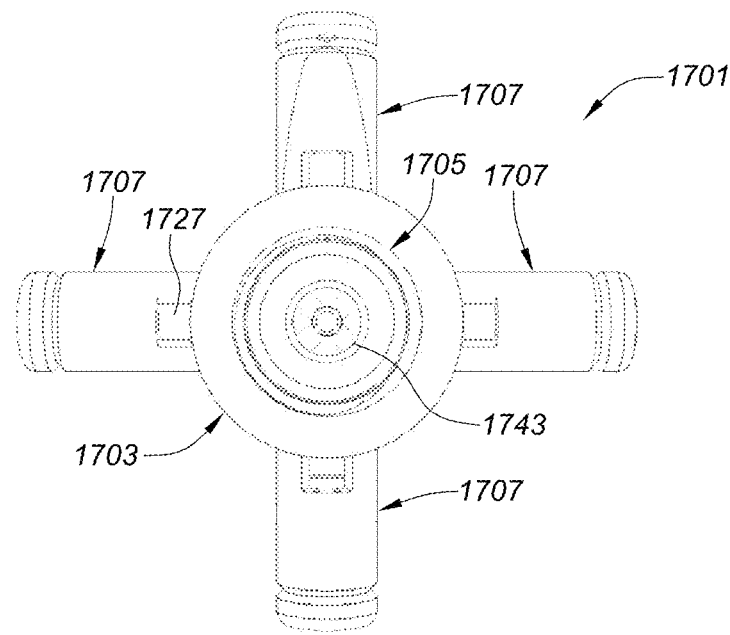
FIG. 17D is a bottom view of the attachment device of FIG. 17A.
Figure 17E:
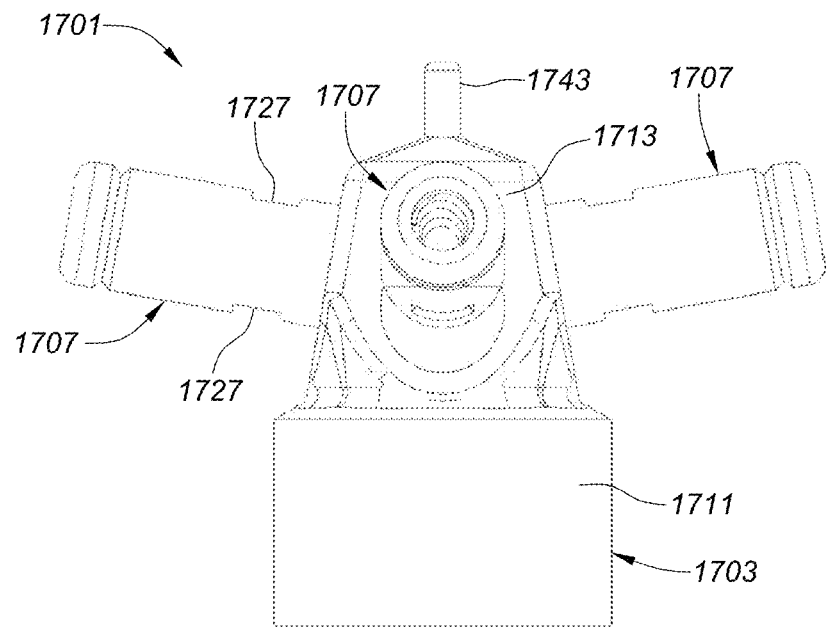
FIG. 17E is a side view of the attachment device of FIG. 17A.
Figure 17F:
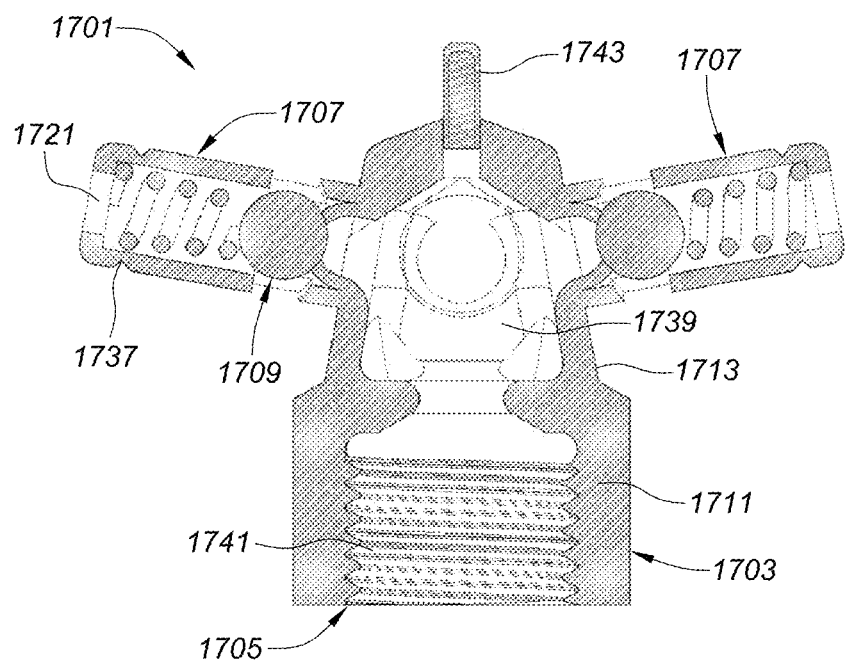
FIG. 17F is a side cutaway view of the attachment device of FIG. 17A.
Figure 17G:
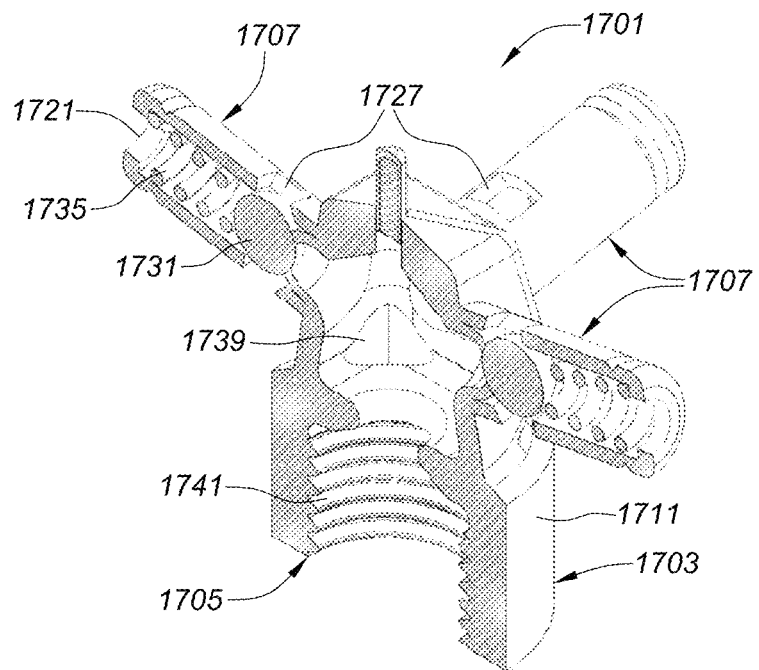
FIG. 17G is an upper perspective cutaway view of the attachment device of FIG. 17A.

As best seen in FIG. 17F, there is shown that each fluid inlet port 1707 comprises an attachment device mechanism 1709 for selectively starting and stopping the flow of fluid from the respective fluid source (not shown) to the fluid outlet port 1705. The attachment device mechanism 1709 comprises a valve having a ball 1731 moveable between an open valve position (shown in later embodiments) and closed valve position (as shown in FIG. 17F). The attachment device mechanism 1709 also comprises a spring 1735 housed within each fluid inlet port 1707. More particularly, the valve comprises the spring 1735 for biasing the ball 1731 to the closed valve position (as shown in FIG. 17F).

Each arm of each fluid inlet port 1707 comprises a groove 1737 about its periphery. As can also be seen in FIG. 17F, the body 1703 comprises a hollow chamber 1739 that allows fluid communication between the hollow cube 1713 and the short hollow cylinder 1711. During operation, when the valve is open, for example, fluid from a fluid source (not shown) may enter the access hole 1721, through/around the spring 1735, around the ball 1731, through the valve orifice, into the hollow chamber 1739, and exit via the fluid outlet port 1705. In this embodiment, the body 1703 comprises internal threading 1741 at the fluid outlet port 1705 that is connectable to another device, such as a pressure regulator (not shown in FIG. 17F) having external threading (not shown in FIG. 17F).

As can also be seen in FIG. 17F, the attachment device 1701 comprises a bleeder valve 1743 that comprises a fluid pressure indicator which aids an operator in ensuring that the correct/minimum fluid pressure/flow is present before disengaging a fluid source (not shown) from a fluid inlet port 1707, thereby maintaining the fluid pressure/flow of fluid entering and exiting the attachment device 1701 via the fluid inlet ports 1707 and fluid outlet port 1705, respectively.

Figure 18A:
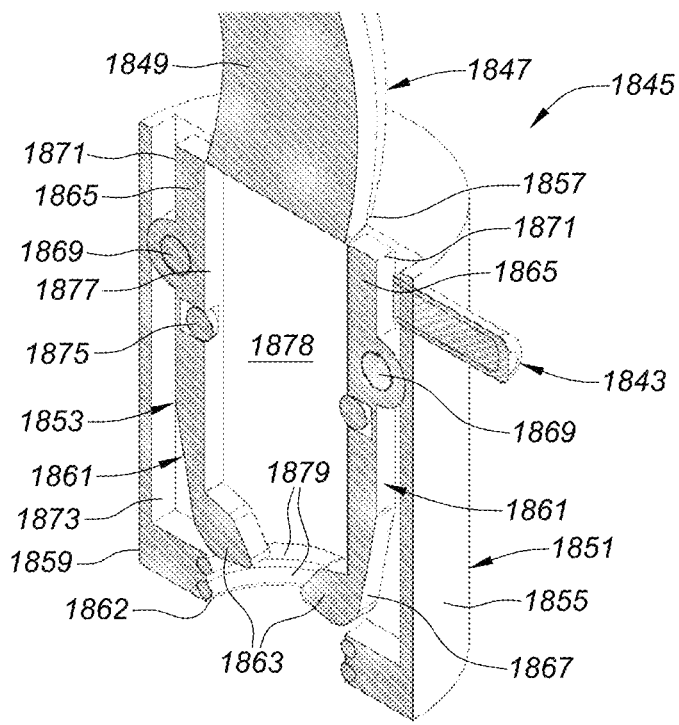
FIG. 18A is an upper perspective view of a connector formed according to an embodiment of the invention in which there are pincer rods.
Figure 18B:
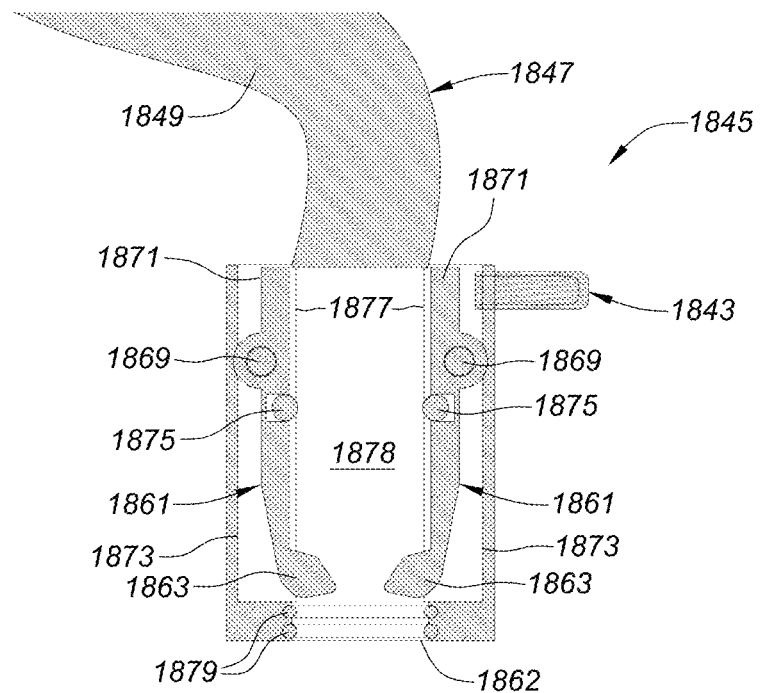
FIG. 18B is a side cutaway view of the connector of FIG. 18A.

Referring now to FIGS. 18A-18B, there is shown a perspective cutaway view and a side cutaway view of a connector generally indicated 1845 that is formed according to an embodiment of the invention. The connector 1845 is for connecting a fluid source 1847 and an attachment device (not shown in FIG. 18A/18B), the connector being attachable to the fluid source 1847 and an attachment device (not shown in FIG. 18A/18B). In this embodiment, the fluid source 1847 is a tubular fluid pipe 1849 and is attached to the connector 1845 by a hose barb (not shown). The connector 1845 comprising a housing 1851 and a connector mechanism 1853 for selectively starting and stopping the flow of fluid from the fluid source 1847 (tubular fluid pipe 1849) to the attachment device (not shown in FIG. 18A/18B).

In this embodiment, the housing 1851 is an elongate hollow cylinder 1855 with the tubular fluid pipe 1849 attached at one end 1857 acting as a fluid access end, wherein the opposite end 1859 comprises a connector exit hole 1862 through which fluid can exit the connector towards and into an attachment device (not shown in FIG. 18A/18B), for example. The housing 1851 has a hollow interior 1878.

The connector mechanism 1853 comprises, in this embodiment, two couplers 1861 each having a wedge member 1863. Of course, it will be understood, in other embodiments, the connector mechanism may comprise more than two couplers. More specifically, in this embodiment, the two couplers 1861 are pincer rods 1865 each having the wedge member 1863 disposed at one end 1867 thereof. The two couplers 1861/pincer rods 1865 are hingeably disposed in the housing 1851 by a pair of pins 1869. The pins are positioned towards the opposite end 1871 of the pincer rods 1865. When actuated, the pincer rods 1865 can pivot about the pins 1869 so that the wedge members 1863 are moved radially outwardly towards the interior wall 1873 of the elongate hollow cylinder 1855 of the housing 1851. This aspect of the connector mechanism 1853 is described in greater detail hereinafter. The connector mechanism 1853 also comprises ball bearings 1875 to generate a positive lock engagement for fitting to another device such as an attachment device (not shown in FIG. 18A/18B), for example. In this embodiment, the ball bearings 1875 are located adjacent the pins 1869 and protrude from the inner face 1877 of the pincer rods 1865.

The connector 1845 also comprises a pair of o-rings 1879 that provide a substantially hermetic seal following connection with another device such as an attachment device (not shown in FIG. 18A/18B), for example. The connector 1845 also comprises a bleeder valve 1843 that comprises a fluid pressure indicator which aids an operator in ensuring that the correct/minimum fluid pressure/flow is present before disengaging a fluid source 1847/connector 1845 from an attachment device (not shown in FIG. 18A/18B), thereby maintaining the fluid pressure/flow of fluid entering and exiting the connector and thus the attachment device (not shown in FIG. 18A/18B).

Figure 19A:
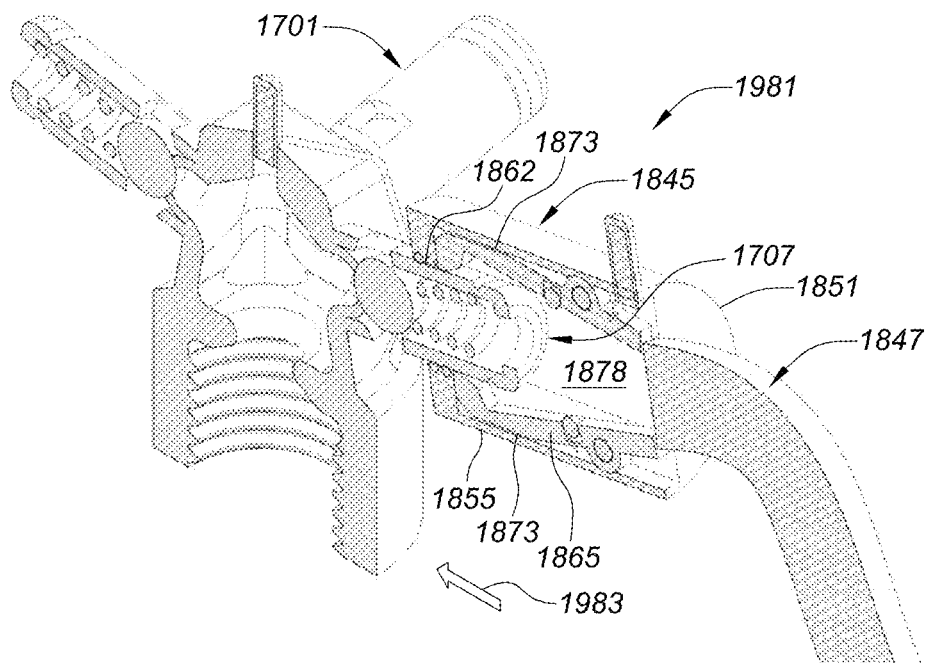
FIG. 19A is a perspective cutaway view of an assembly formed according to an embodiment of the invention in an intermediate position.

Referring now to FIG. 19A, there is shown a perspective cutaway view of an assembly generally indicated 1981 formed according to an embodiment of the invention. The assembly 1981 comprising the attachment device 1701 of FIGS. 17A-17G, and the connector 1845 of FIGS. 18A-18B for connecting a fluid source 1847 to the attachment device 1701. The attachment device 1701 comprising fluid inlet ports 1707.

Figure 19B:
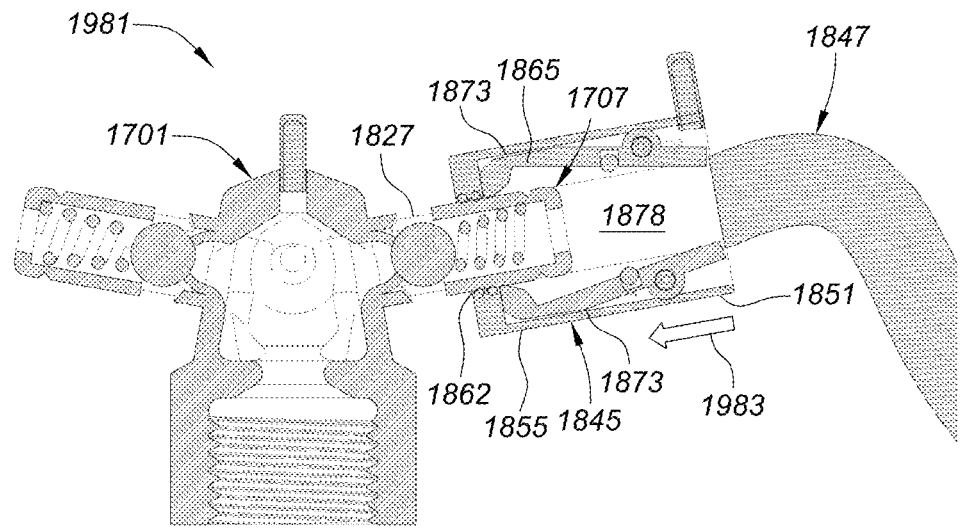
FIG. 19B is a side cutaway view of the assembly of FIG. 19A in the intermediate position.

FIGS. 19A-19B show the assembly formed according to an embodiment of the invention in an intermediate position in a perspective cutaway view and a side cutaway view, respectively. During operation, the female connector 1845 (already attached to the fluid source 1847) is pushed on to the male attachment device 1701 in the direction indicated by arrow 1983, such that the fluid inlet port 1707 of the attachment device 1701 enters the hollow interior 1878 of the connector 1845 via the connector exit hole 1862. In this intermediate position, the pincer rods 1865 of the connector mechanism 1853 are pushed radially outwardly by the wedge members 1863 towards the interior wall 1873 of the elongate hollow cylinder 1855 of the housing 1851 due to making contact with the outer surface of the fluid inlet port 1707, whereby the pincer rods 1865 hinge about the pair of pins 1869 pins of the connector housing 1851.

Figure 19C:
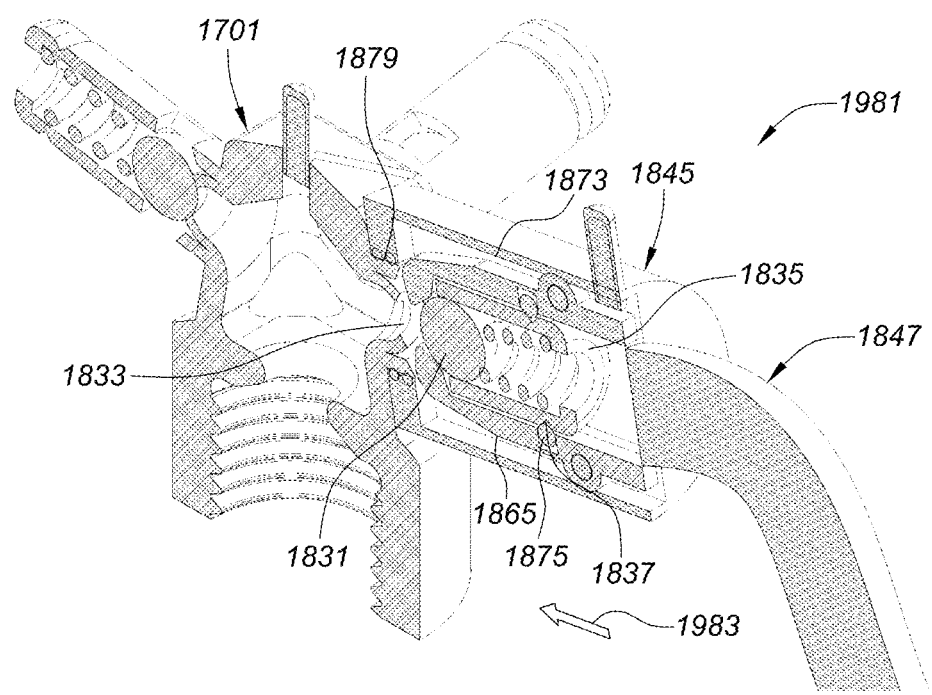
FIG. 19C is a perspective cutaway view of the assembly of FIG. 19A in an engaged position.
Figure 19D:
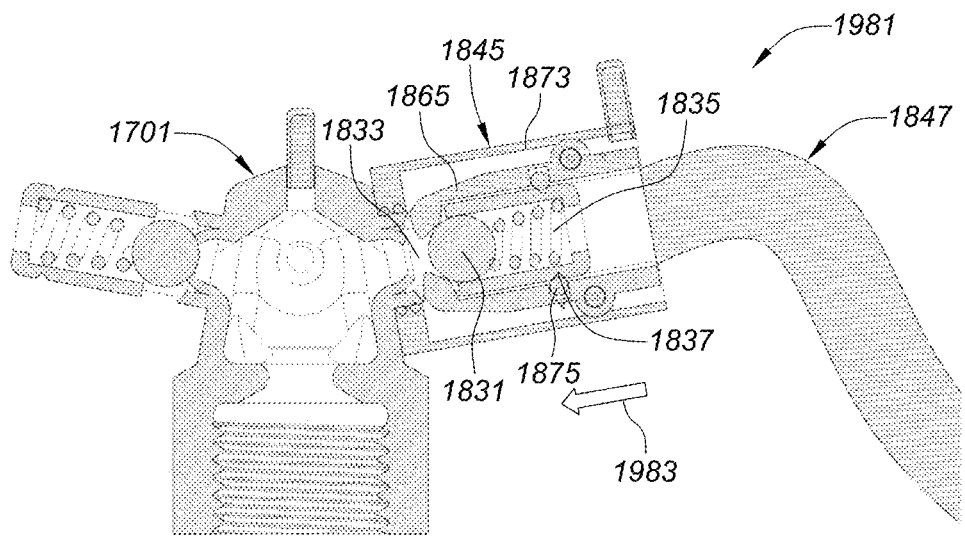
FIG. 19D is a side cutaway view of the assembly of FIG. 19A in an engaged position.

As the connector 1845 is continued to be pushed by an operator in the direction indicated by arrow 1983, it eventually reaches an engaged position as shown in FIGS. 19C-19D. Here, the pincer rods 1865 hinge back radially inwardly to their original position away from the interior wall 1873 of the elongate hollow cylinder 1855 of the housing 1851. The wedge members 1863 are thus aligned with the pair of apertures 1827 so that they can protrude therethrough and access the ball 1831. The effect of the wedge members 1863 contacting the ball 1831 is to move the ball 1831 so that it compresses the spring 1835 and moves away from the valve orifice 1833 so as to unseal the valve and effect an open valve position thus allowing passage of fluid therethrough.

At the same time, the connector 1845 engages the attachment device 1701 by way of the connector mechanism 1853 comprising ball bearings 1875 to generate a positive lock engagement with the groove 1837. The connector 1845 and attachment device 1701 will be held in this engagement until a substantial force in the direction opposite to that of arrow 1983 is applied to overcome the resistance effected by the ball bearings 1875 locking with the groove 1837. In the engaged position, the connector 1845 also forms a substantially hermetic seal with the attachment device 1701 due to the pair of o-rings 1879 of the connector 1845 tightly abutting the exterior of the male attachment device 1701.

Figure 20A:
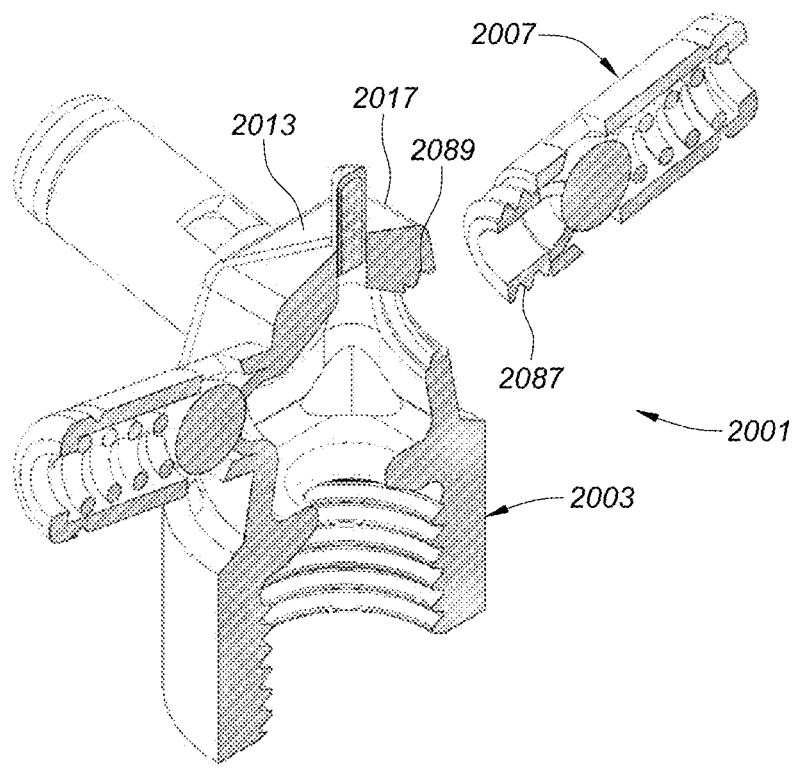
FIG. 20A is a perspective cutaway view of an attachment device formed according to alternative embodiment of the invention.
Figure 20B:
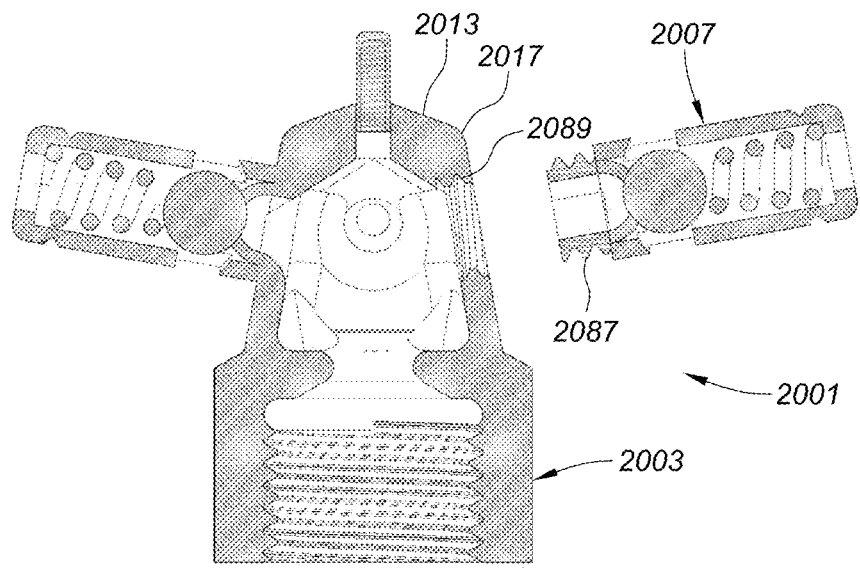
FIG. 20B is a side cutaway view of the attachment device of FIG. 20A.

Referring now to FIGS. 20A-20B there is shown a perspective cutaway view and side cutaway view of an attachment device 2001 formed according to an alternative embodiment of the invention, respectively. In this embodiment, the attachment device 2001 comprises a fluid inlet port 2007 that is detachably attached to the body 2003. The fluid inlet port 2007 comprises an external screw thread 2087 at one end that is engageable with an internal screw thread 2089 positioned on a face 2017 of the hollow cube 2013.

Figure 21A:
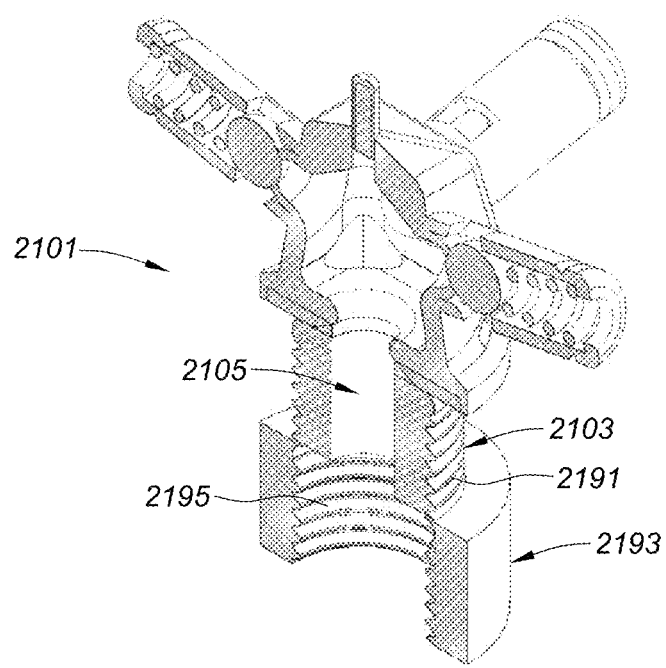
FIG. 21A is a perspective cutaway view of an attachment device formed according to a further alternative embodiment of the invention.
Figure 21B:
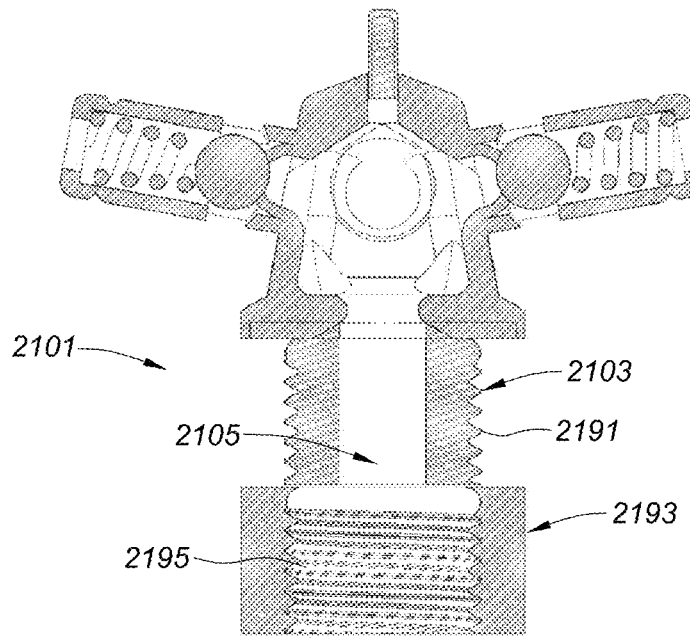
FIG. 21B is a side cutaway view of the attachment device of FIG. 21A.

Referring now to FIGS. 21A-21B there is shown a perspective cutaway view and side cutaway view of an attachment device 2101 formed according to a further alternative embodiment of the invention, respectively. In this embodiment, the attachment device 2101 comprising a body 2103 having a fluid outlet port 2105; the body 2103 comprising external threading 2191 at the fluid outlet port 2105 that is connectable to a pressure regulator 2193 (partially shown) having internal threading 2195.

Figure 22A:
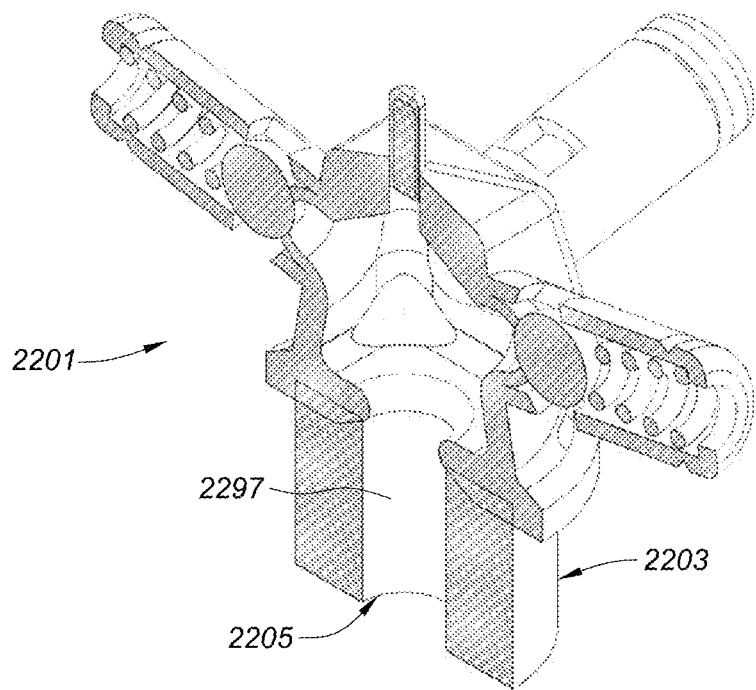
FIG. 22A is a perspective cutaway view of an attachment device formed according to a further alternative embodiment of the invention.
Figure 22B:
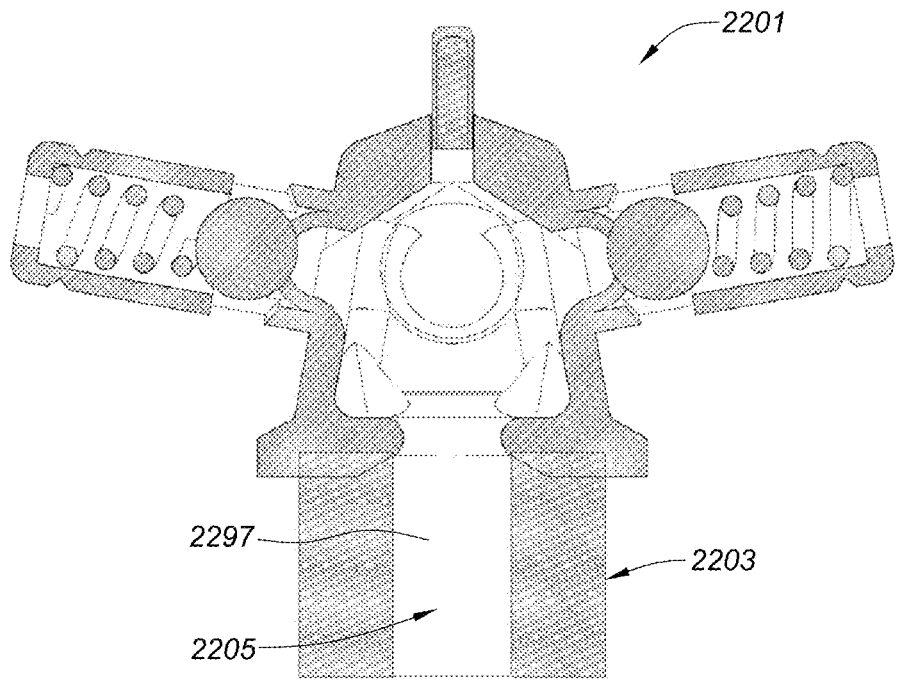
FIG. 22B is a side cutaway view of the attachment device of FIG. 22A.

Referring now to FIGS. 22A-22B there is shown a perspective cutaway view and side cutaway view of an attachment device 2201 formed according to a further alternative embodiment of the invention, respectively. In this embodiment, the attachment device 2201 comprising a body 2203 having a fluid outlet port 2205; the body 2203 comprising a push-fit mechanism 2297 that is connectable to a pressure regulator (not shown) having a corresponding engagement mechanism.

Figure 23A:
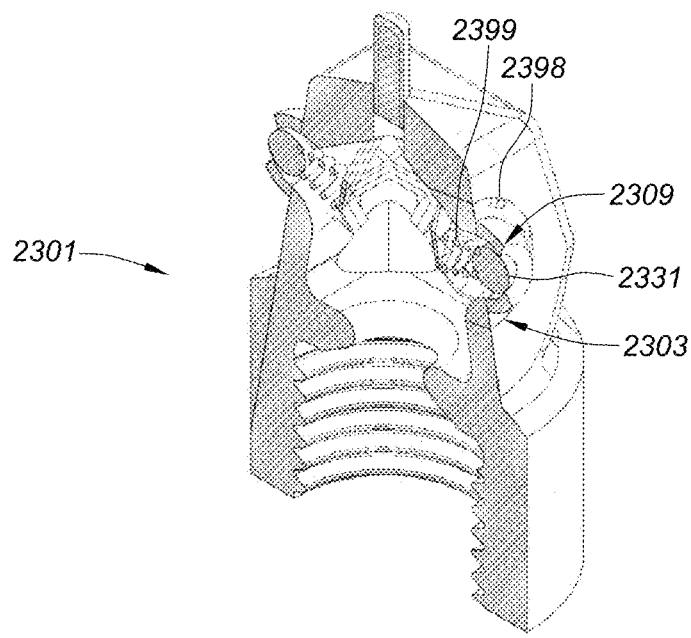
FIG. 23A is a perspective cutaway view of an attachment device formed according to a further alternative embodiment of the invention.
Figure 23B:
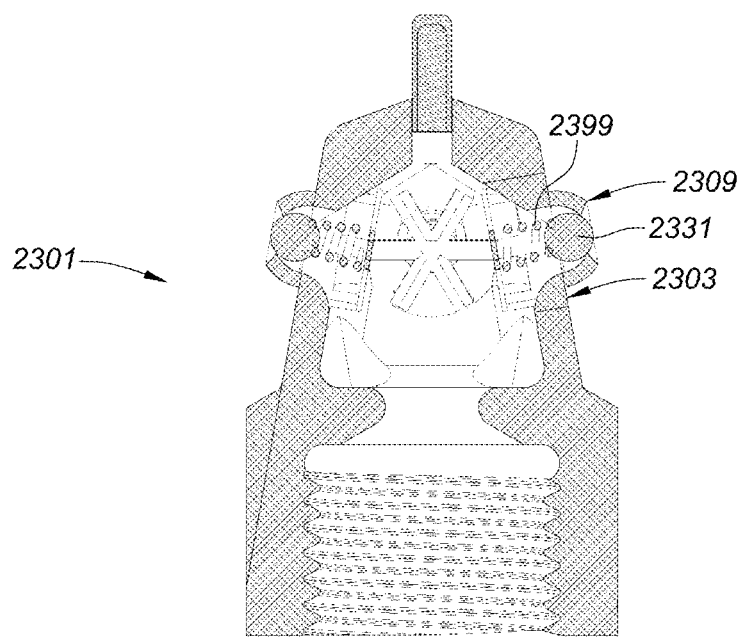
FIG. 23B is a side cutaway view of the attachment device of FIG. 23A.

Referring now to FIGS. 23A-23B there is shown a perspective cutaway view and side cutaway view of an attachment device 2301 formed according to a further alternative embodiment of the invention, respectively. In this embodiment, the attachment device 2301 comprises an attachment device mechanism 2309 which comprises a ball 2331 proximal the body 2303. The ball 2331 resides partially inside the body 2303 and partially protrudes outwardly from the body 2303. The ball 2331 is moveable between a fluid start flow position and fluid stop flow position by mechanically or magnetically moving the ball 2331 towards the interior of the body 2303 by way of a connector described hereinafter. The attachment device mechanism 2309 comprises a spring 2399 for biasing the ball 2331 to the stop flow position; that is to close the seal to avoid escape of fluid from the attachment device 2301. The attachment device 2301 comprises six attachment device coupling magnets 2398 arranged in a circular shape on the body 2303 adjacent the ball 2331 which can be used to couple with magnets from a connector, for instance.

Figure 24A:
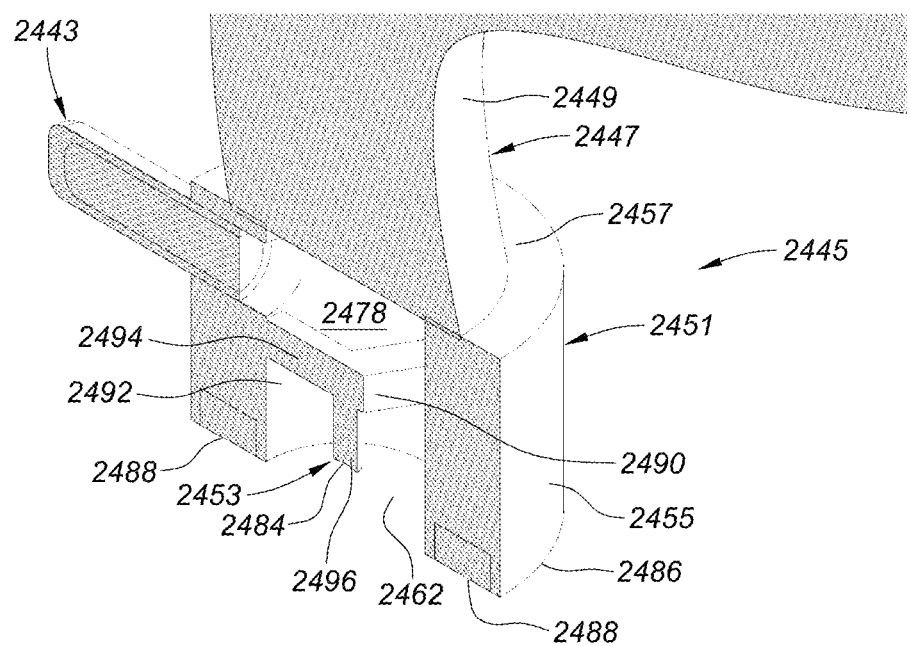
FIG. 24A is a perspective cutaway view of a connector formed according to an embodiment of the invention.
Figure 24B:
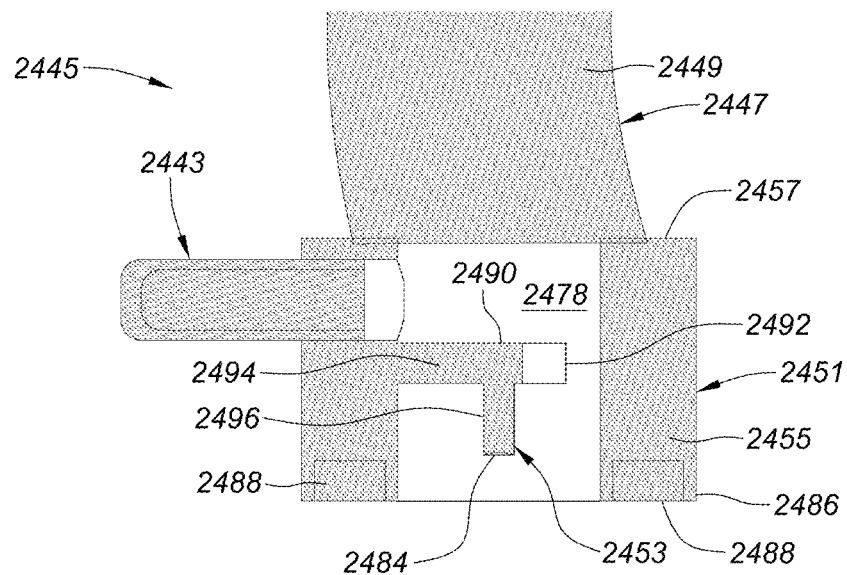
FIG. 24B is a side cutaway view of the connector of FIG. 24A.

Referring now to FIGS. 24A-24B there is shown a perspective cutaway view and side cutaway view of a connector formed according to an alternative embodiment of the invention, respectively.

The connector 2445 is for connecting a fluid source 2447 and an attachment device (not shown in FIG. 24A/24B), the connector being attachable to the fluid source 2447 and an attachment device (not shown in FIG. 24A/24B). In this embodiment, the fluid source 2447 is a tubular fluid pipe 2449 and is attached to the connector 2445 by a hose barb (not shown). The connector 2445 comprising a housing 2451 and a connector mechanism 2453 for selectively starting and stopping the flow of fluid from the fluid source 2447 (tubular fluid pipe 2449) to the attachment device (not shown in FIG. 24A/24B).

In this embodiment, the housing 2451 is a short hollow cylinder 2455 with the tubular fluid pipe 2449 attached at one end 2457 acting as a fluid access end, wherein the opposite end 2459 comprises a connector exit hole 2462 through which fluid can exit the connector towards and into an attachment device (not shown in FIG. 24A/24B), for example. The housing 2451 has a hollow interior 2478.

The connector mechanism 2453 comprises, in this embodiment, a push-rod 2496. Of course, it will be understood, in other embodiments, the connector mechanism may comprise more than one push-rod. More specifically, in this embodiment, the push-rod 2496 is elongate in form and is centrally positioned and substantially longitudinally aligned with a longitudinal direction of the short hollow cylinder 2455. The push-rod 2496 is suspended in position by an L-shape frame 2494 which is arranged orthogonally with respect to the push-rod 2496. The V-shape frame 2494 is connected to and extend from two points on the interior wall 2492 of the short hollow cylinder 2455 so that the apex 2490 of the V-shape frame 2494 is centrally radially positioned, and the push-rod 2496 is suspended from the apex 2490. The push-rod 2496 has a concave end 2484 adapted to receive a ball, for instance. This aspect of the connector mechanism 2453 is described in greater detail hereinafter.

The connector mechanism 2453 also comprises six connector coupling magnets 2488 arranged in a circular shape on the end 2486 of the short hollow cylinder 2455 which can be used to couple with magnets from an attachment device (not shown in FIGS. 24A/24B), for instance.

The connector 2445 also comprises a bleeder valve 2443 that comprises a fluid pressure indicator which aids an operator in ensuring that the correct/minimum fluid pressure/flow is present before disengaging a fluid source 2447/connector 2445 from an attachment device (not shown in FIG. 24A/24B), thereby maintaining the fluid pressure/flow of fluid entering and exiting the connector and thus the attachment device (not shown in FIG. 24A/24B). The bleeder valve 2443 extends orthogonally outwardly from the short hollow cylinder 2455.

Figure 25A:
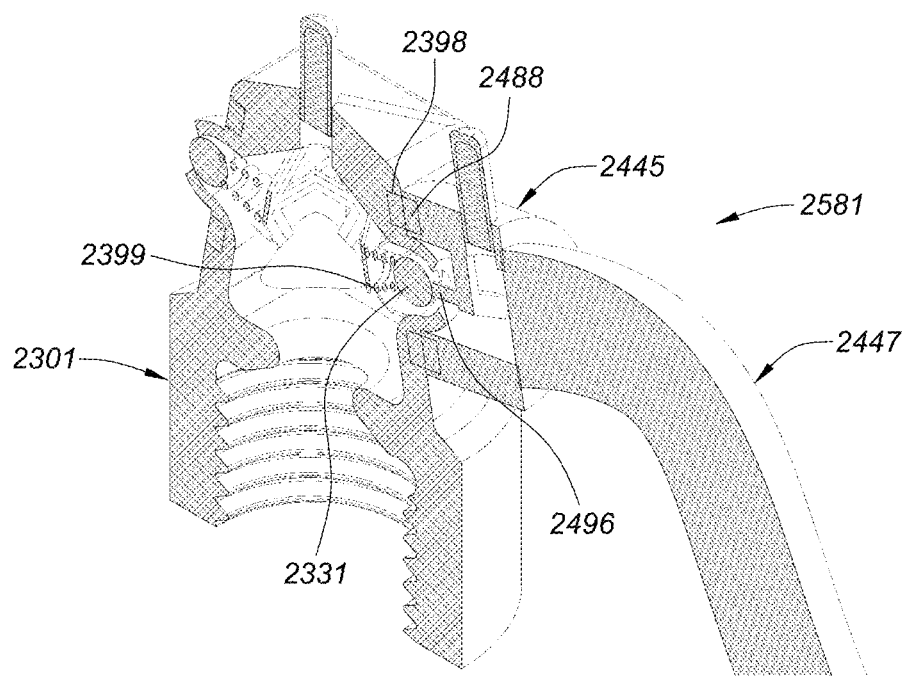
FIG. 25A is a perspective cutaway view of an assembly formed according to an embodiment of the invention in an engaged position.
Figure 25B:
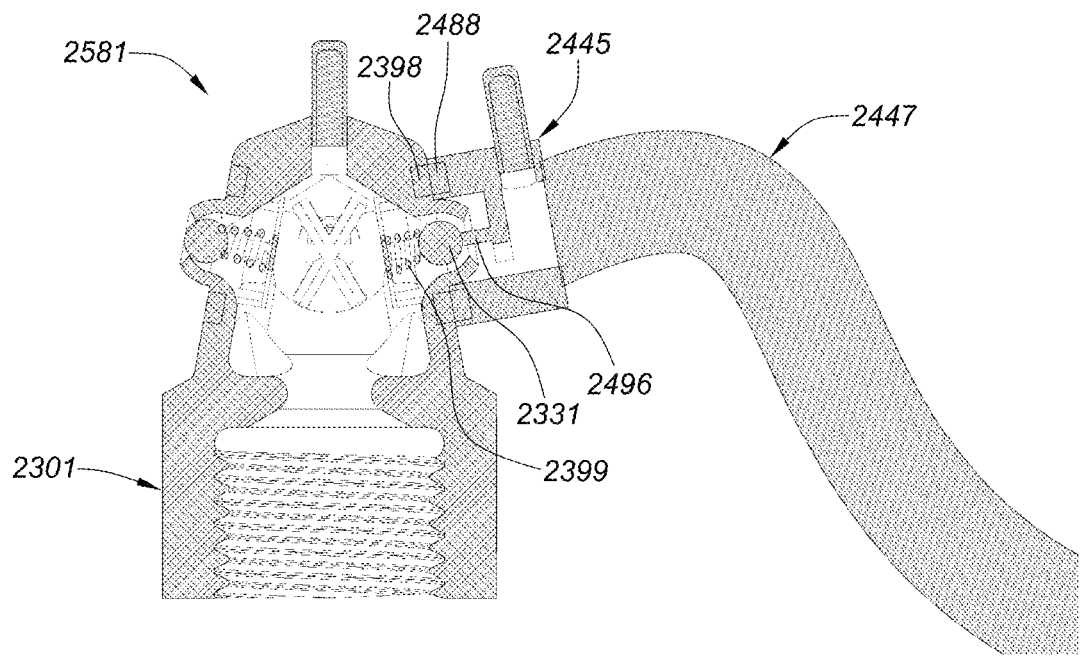
FIG. 25B is a side cutaway view of the assembly of FIG. 25A in the engaged position.

Referring now to FIGS. 25A-25B, there is shown a perspective cutaway view and side cutaway view of an assembly generally indicated 2581 formed according to an embodiment of the invention, respectively. The assembly 2581 comprising the attachment device 2301 of FIGS. 23A-23B, and the connector 2445 of FIGS. 24A-24B for connecting a fluid source 2447 to the attachment device 2301. In this embodiment, the push-rod 2496 of the connector mechanism 2453 having the concave end 2484 mechanically pushes the ball 2331 (of the attachment device mechanism 2309) inwardly towards the interior of the body 2303. The ball 2331 therefore moves from a stop flow position to a start flow position. Although the movement of the ball 2331 in this embodiment is by a mechanical force, it will be appreciated that in other embodiments the push-rod 2496 may be formed from a magnetic material so that it may magnetically repel the ball 2331 (of the attachment device mechanism 2309) inwardly towards the interior of the body 2303. The attachment device mechanism 2309 comprises a spring 2399 which is shown compressed by the ball 2331 in the start flow position so that fluid is able to flow from the fluid source 2447, to the connector 2451, and through to the attachment device 2301. In this way, the connector mechanism 2453 and attachment device mechanism 2309 are able to interconnect for enhanced performance.

The six attachment device coupling magnets 2398 arranged in a circular shape on the body 2303 of the attachment device 2301 mate with the six connector coupling magnets 2488 arranged in a circular shape on the end 2486 of the connector 2445 to provide a strong detachably attachable coupling of the connector 2445 and the attachment device 2301. In this embodiment, the magnets 2398 and 2488 are neodymium magnets.

Figure 26A:
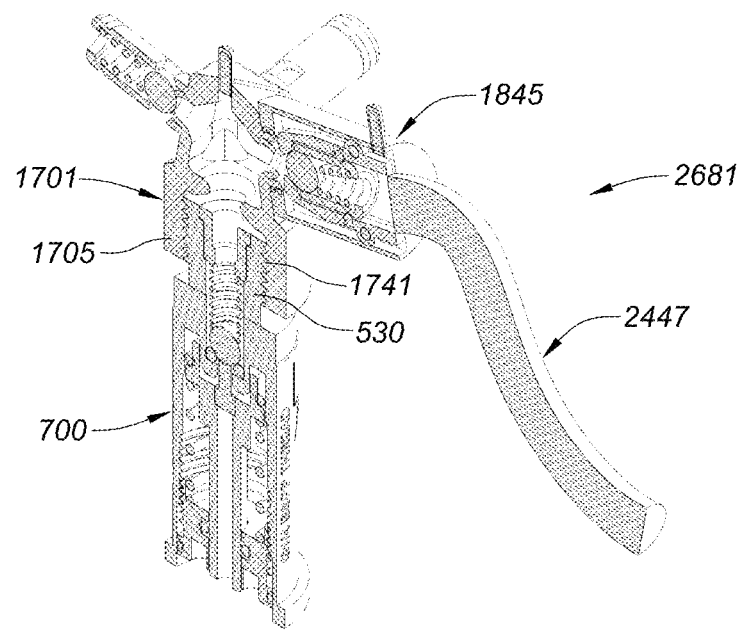
FIG. 26A is a perspective cutaway view of an assembly formed according to another embodiment of the invention in an engaged position.
Figure 26B:
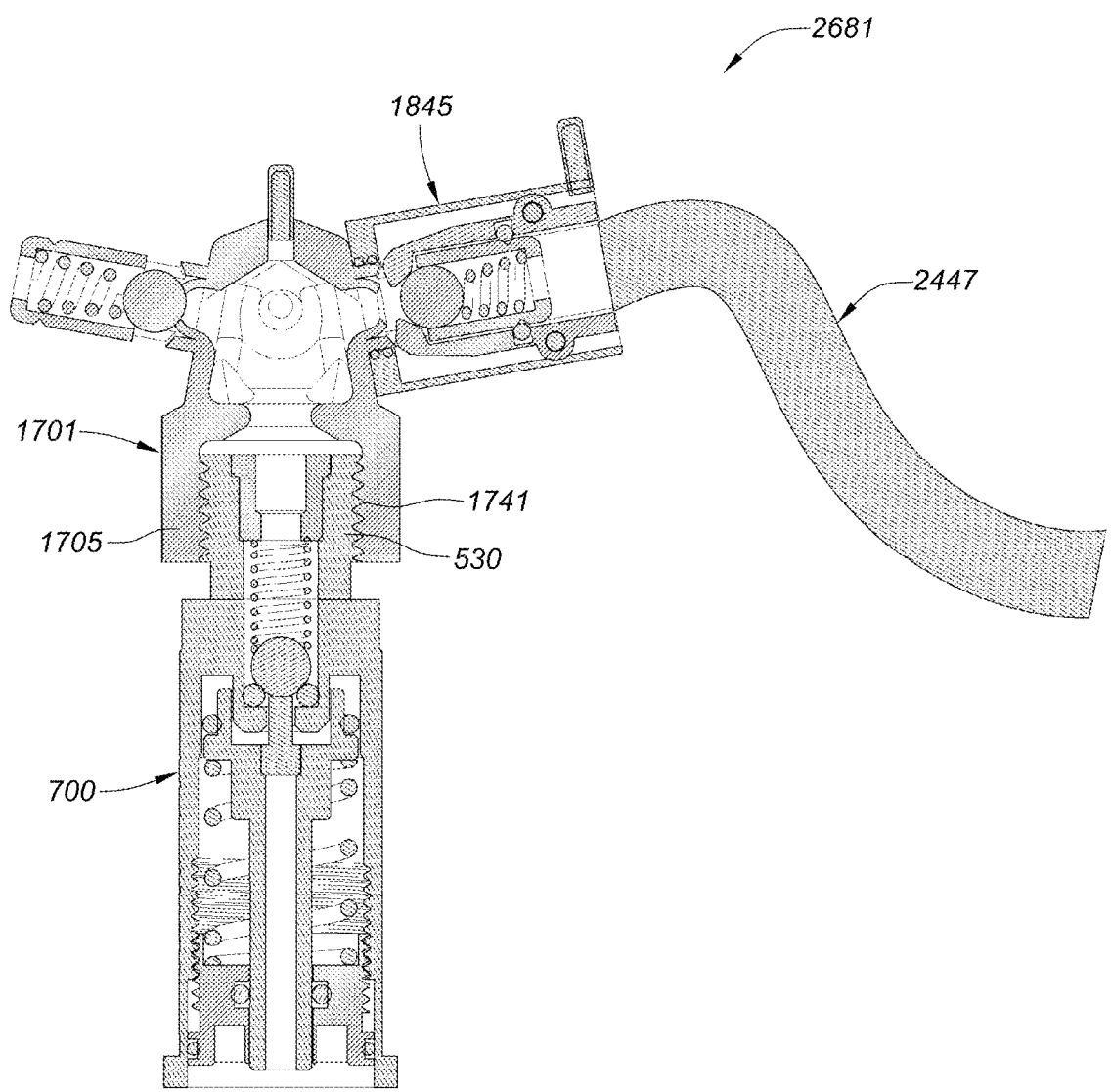
FIG. 26B is a side cutaway view of the assembly of FIG. 26A in the engaged position.

Referring now to FIGS. 26A-26B, there is shown a perspective cutaway view and side cutaway view of an assembly generally indicated 2681 in an engaged position formed according to an embodiment of the invention, respectively. The assembly 2681 is the same as that shown in FIGS. 19C-19D comprising the attachment device 1701 of FIGS. 17A-17G, and the connector 1845 of FIGS. 18A-18B, except the assembly 2681 further comprises the pressure regulator 700 of FIGS. 9-14. The external threading 530 of the pressure regulator 700 engages the internal threading 1741 at the fluid outlet port 1705. During operation, in the open valve/start flow state of the various components described herein, fluid can pass from the fluid source 2447, into the connector 1845, through to the attachment device 1701, and into the pressure regulator 700.

Figure 27A:
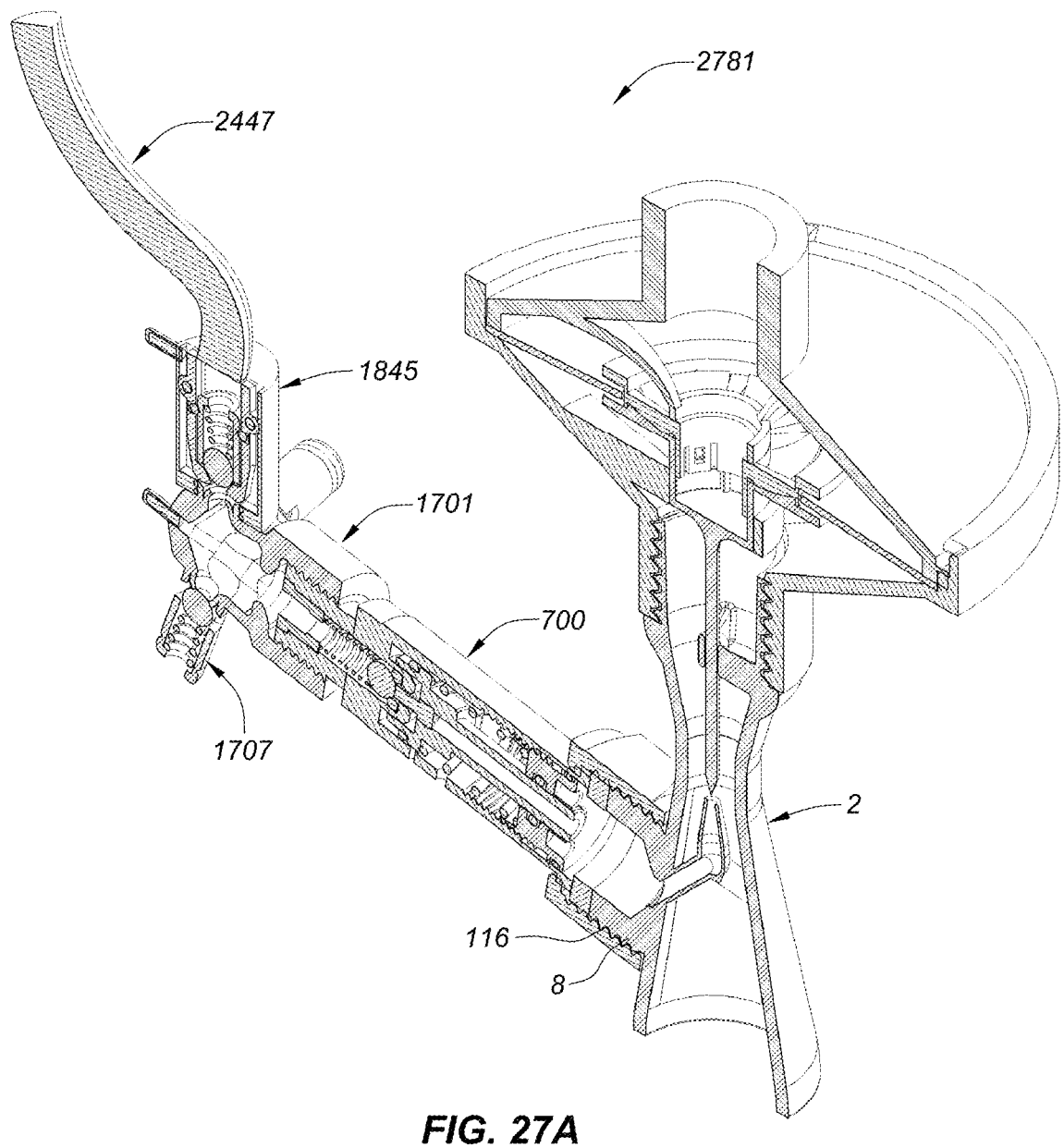
FIG. 27A is a perspective cutaway view of an assembly formed according to an embodiment of the invention comprising a first connector and first fluid source in an engaged position.
Figure 27B:
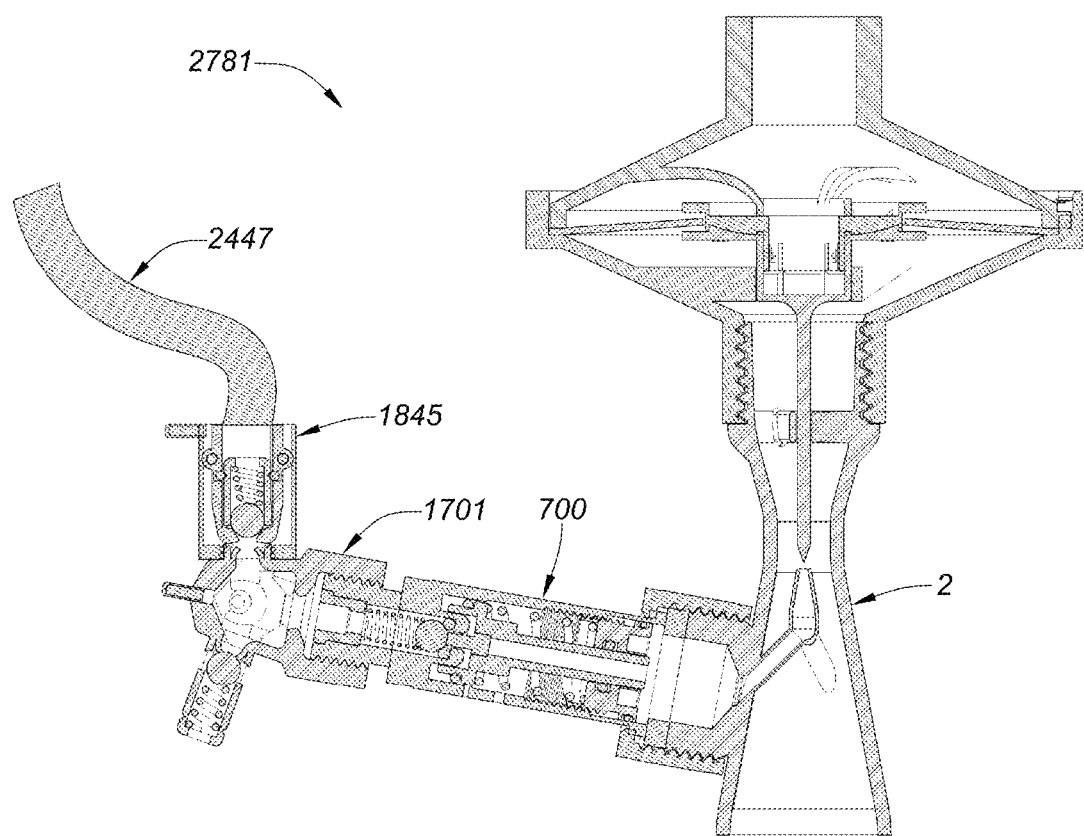
FIG. 27B is a side cutaway view of the assembly of FIG. 27A in the engaged position.

Referring now to FIGS. 27A-27B, there is shown a perspective cutaway view and side cutaway view of an assembly generally indicated 2781 in an engaged position formed according to an embodiment of the invention, respectively. The assembly 2781 is the same as that shown in FIGS. 26A-26B comprising the attachment device 1701 of FIGS. 17A-17G, the connector 1845 of FIGS. 18A-18B, the pressure regulator 700 of FIGS. 9-14, except the assembly 2781 further comprises the ventilator of FIGS. 1-4. The lower internal threading 116 of the pressure regulator 700 engages the threads 8 of the ventilator. During operation, in the open valve/start flow state of the various components described herein, fluid can pass from the fluid source 2447, into the connector 1845, through to the attachment device 1701, through the pressure regulator 700, and into the ventilator. The assembly 2781 is shown in the open flow state.

Figure 27C:
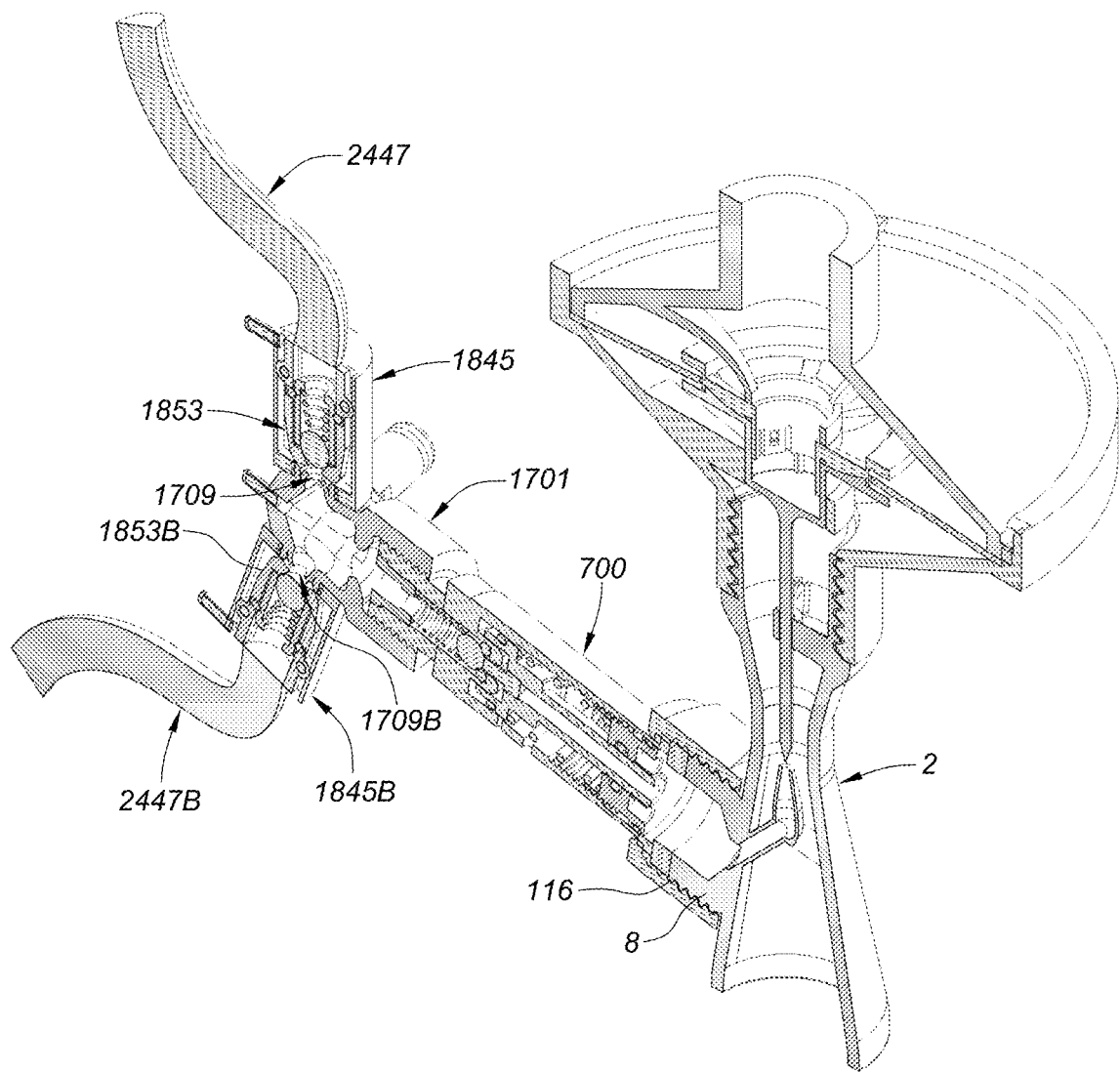
FIG. 27C is a perspective cutaway view of the assembly of FIG. 27A further comprising a second connector and second fluid source in an engaged position.
Figure 27D:
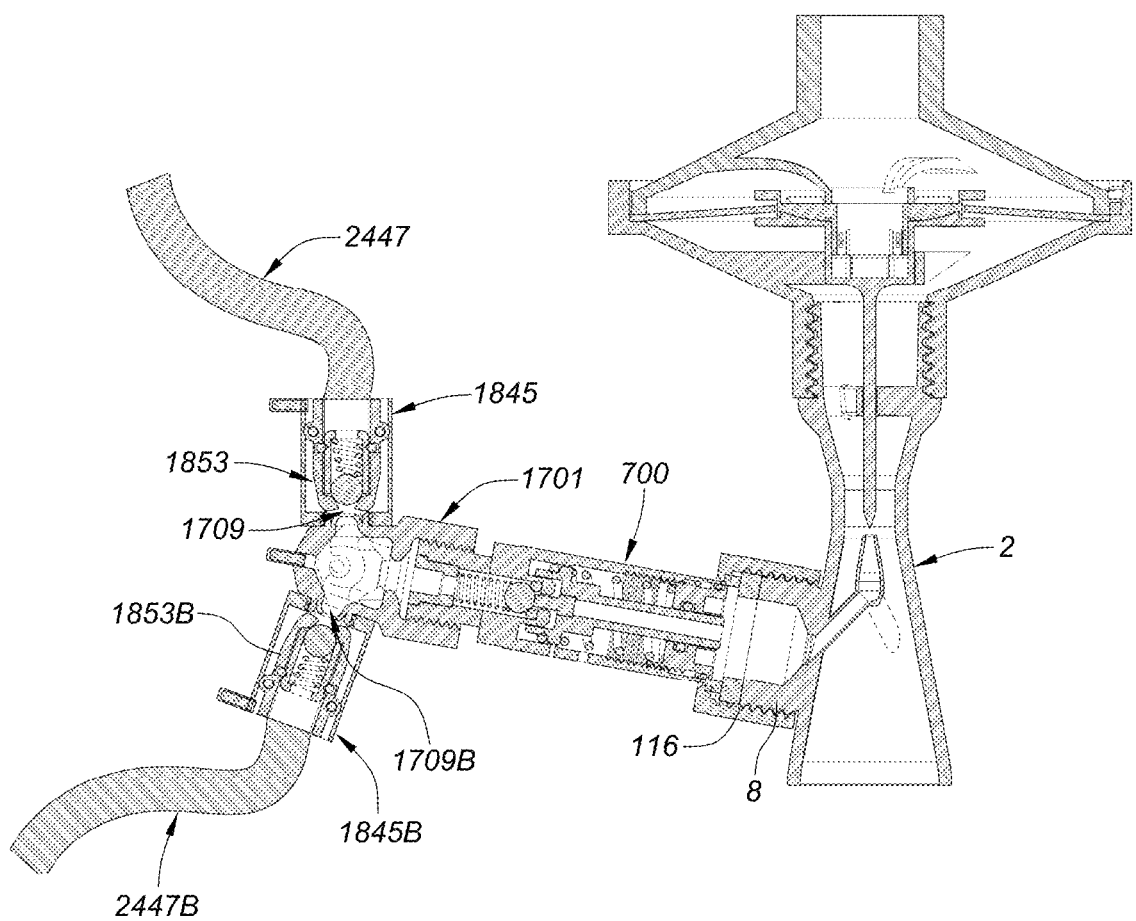
FIG. 27D is a side cutaway view of the assembly of FIG. 27C in the engaged position.

Referring now to FIGS. 27C-27D, there is shown a perspective cutaway view and side cutaway view of the assembly 2781 of FIGS. 27A-27B, but further comprising a second connector and second fluid source in an engaged position. The assembly 2781 is the same as that shown in FIGS. 26A-26B comprising the attachment device 1701 of FIGS. 17A-17G, the connector 1845 of FIGS. 18A-18B, the pressure regulator 700 of FIGS. 9-14, except the assembly 2781 further comprises the ventilator of FIGS. 1-4. The lower internal threading 116 of the pressure regulator 700 engages the threads 8 of the ventilator. During operation, in the open valve/start flow state of the various components described herein, fluid can pass from the fluid source 2447, into the connector 1845, through to the attachment device 1701, through the pressure regulator 700, and into the ventilator 2. The assembly 2781 is shown in the open flow state.

Referring now to FIGS. 27C-27D is a perspective cutaway view and side view, respectively, of the assembly of FIG. 27A further comprising a second connector 1845B and second fluid source 2447 in an engaged position. The second connector is engaged with one of the other fluid inlet ports 1707. The connector mechanism 1853 and 1853B and the attachment device mechanism 2309 and 2309B are in the open state/start flow state.

Figure 27E:
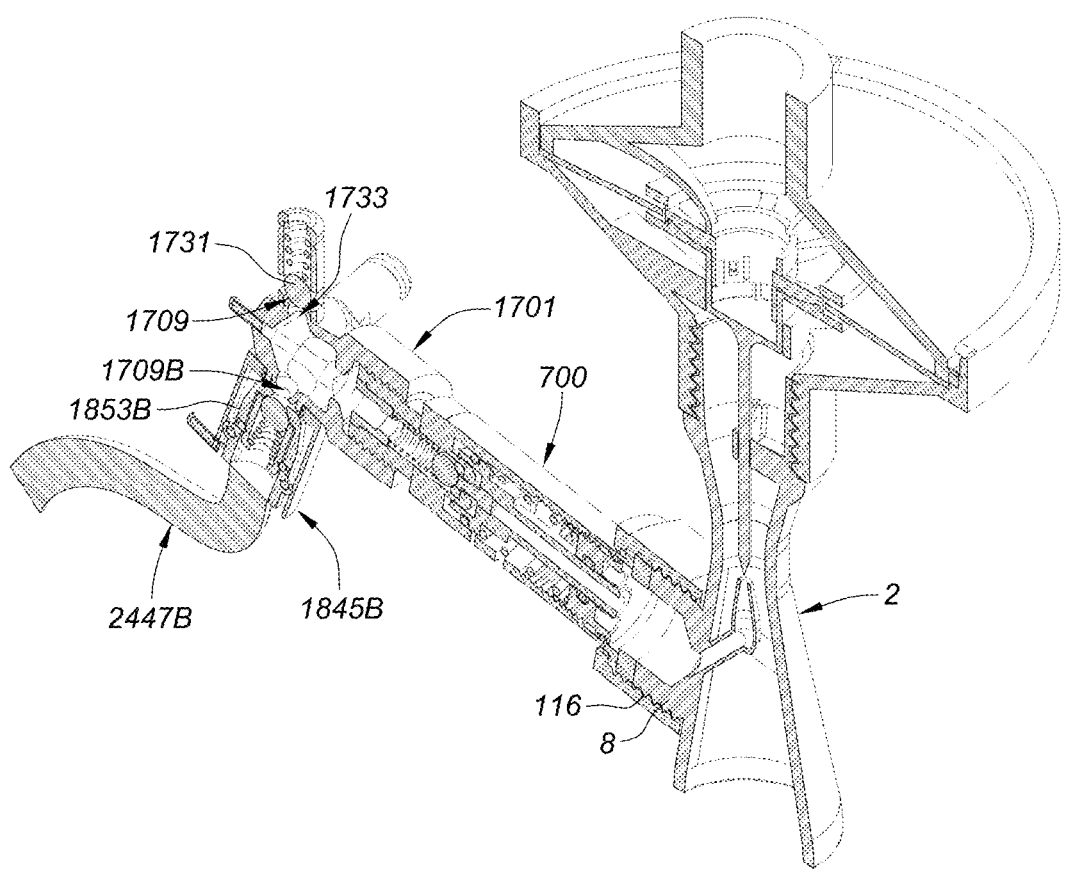
FIG. 27E is a perspective cutaway view of the assembly of FIG. 27C following disconnection of the first connector and first fluid source.
Figure 27F:
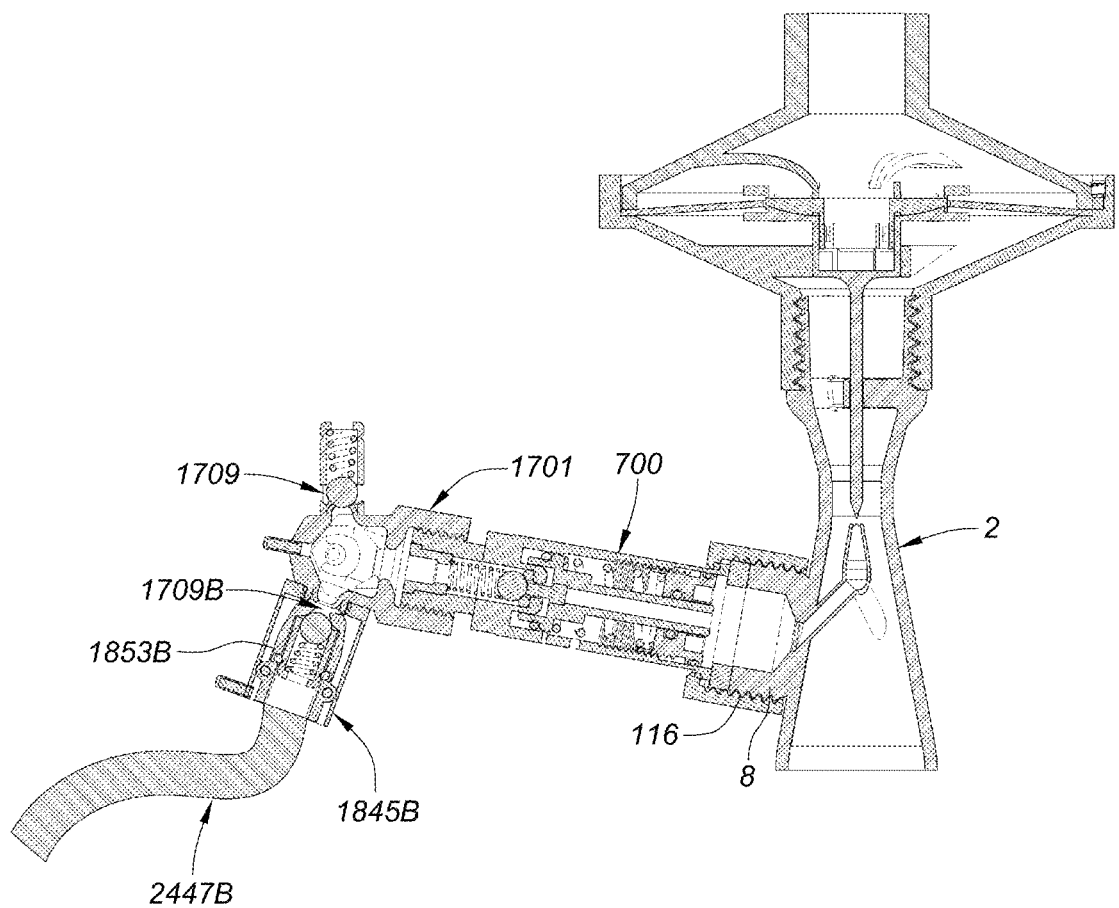
FIG. 27F is a side cutaway view of the assembly of FIG. 27E in the engaged position.

Referring now to FIGS. 27E and 27F is a perspective cutaway view and side view, respectively, following disconnection of the original (first) connector 1845 and first fluid source 2447. Here, it can be seen that the second connector mechanism 1853B and the second attachment device mechanism 1709B remain in the open state/start flow state, while the first attachment device mechanism 1709 reverts to the closed state/stop flow state because valve orifice 1733 is sealed shut by each ball 1731, thereby completing the switch/transfer/transition from one fluid source 2447 to a second fluid source 2447B, without compromising on the pressure and flow speed of the fluid reaching the ventilator 2.

Figure 28:
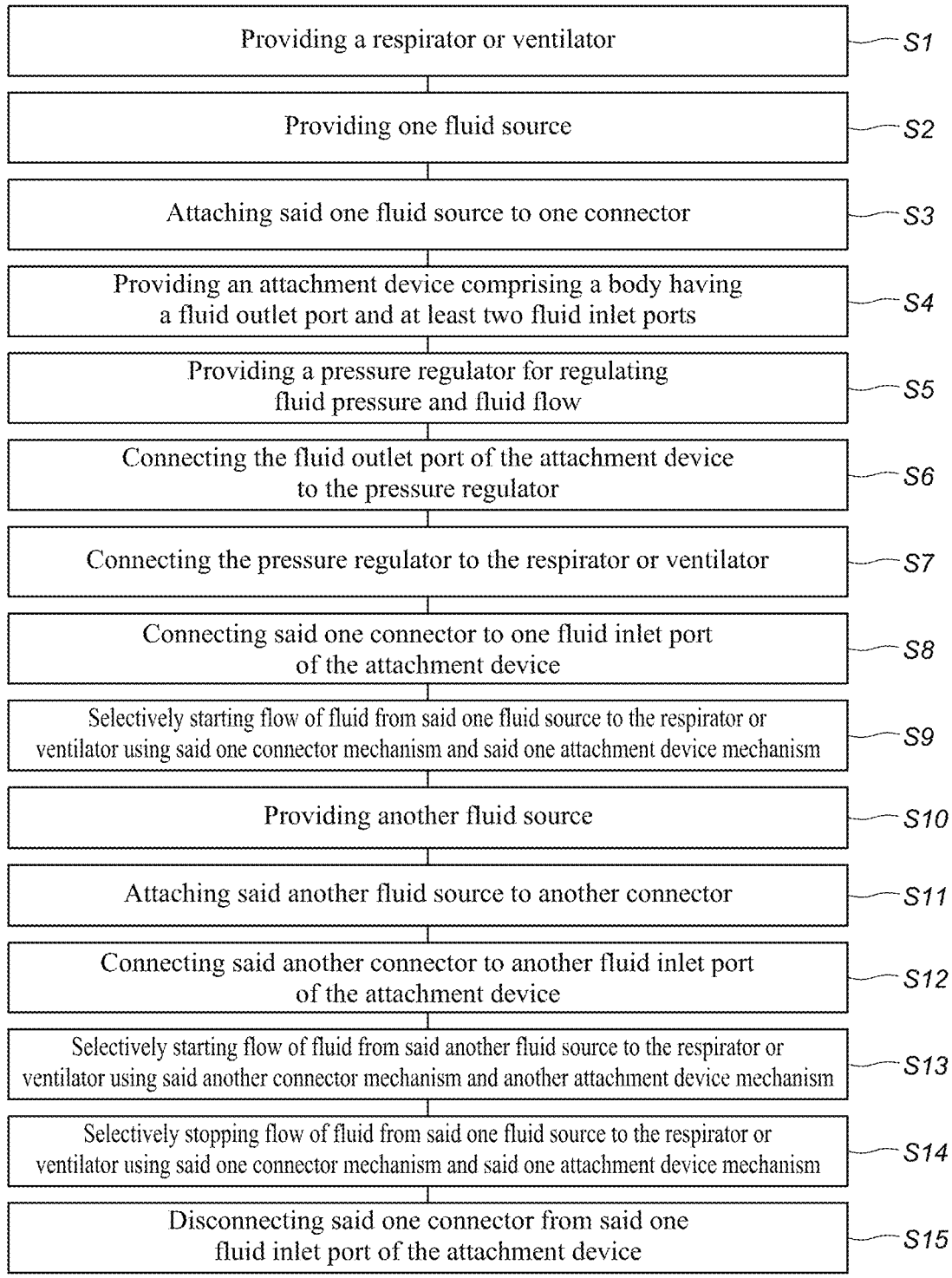
FIG. 28 is a flow diagram of the method according to the invention.
Figure 29A:
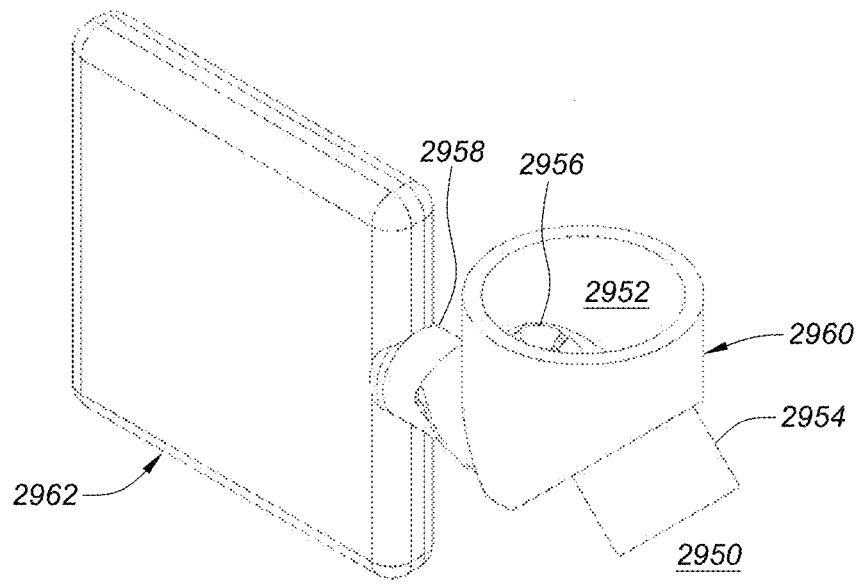
FIG. 29A is an upper perspective view of a reservoir bag apparatus formed according to an embodiment of the invention.
Figure 29B:
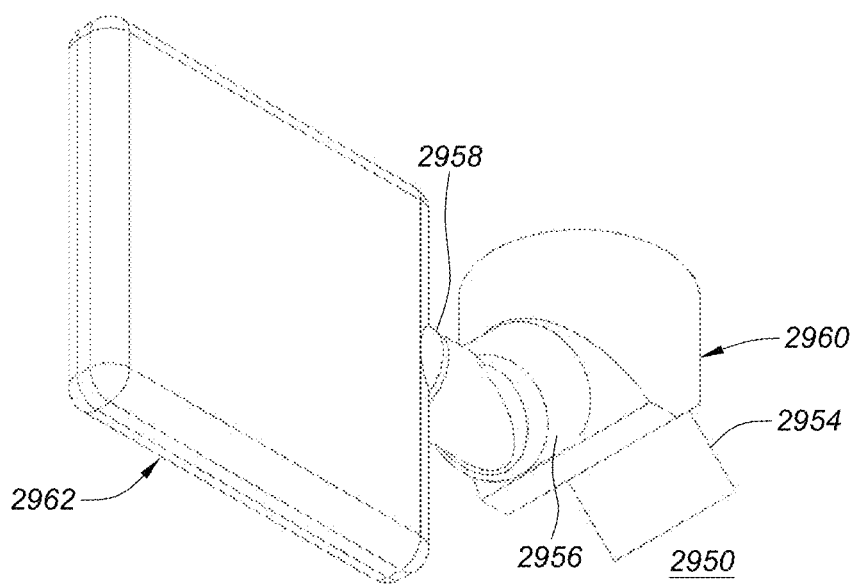
FIG. 29B is a lower perspective view of the reservoir bag and valve apparatus of FIG. 29A.
Figure 29C:
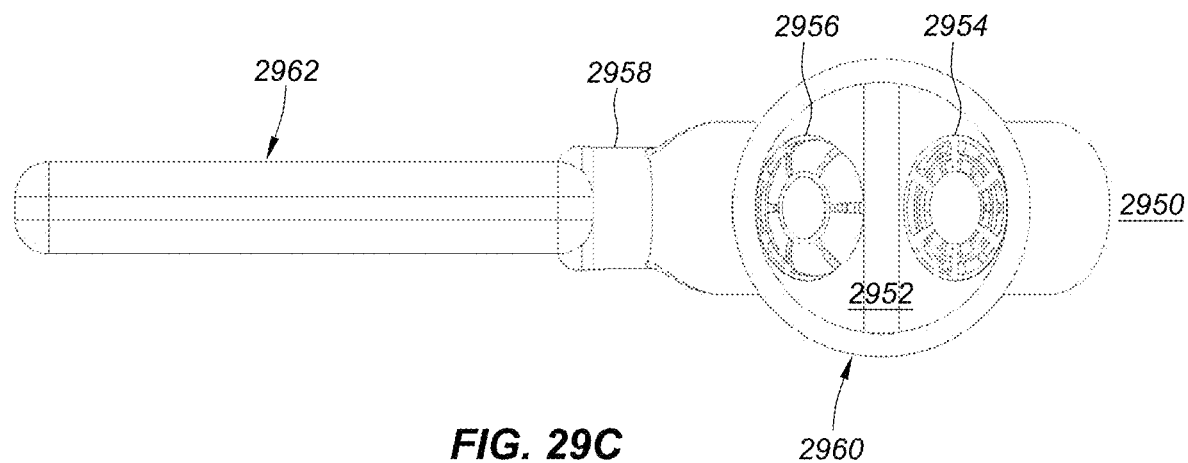
FIG. 29C is a plan view of the reservoir bag and valve apparatus of FIG. 29A.
Figure 29D:
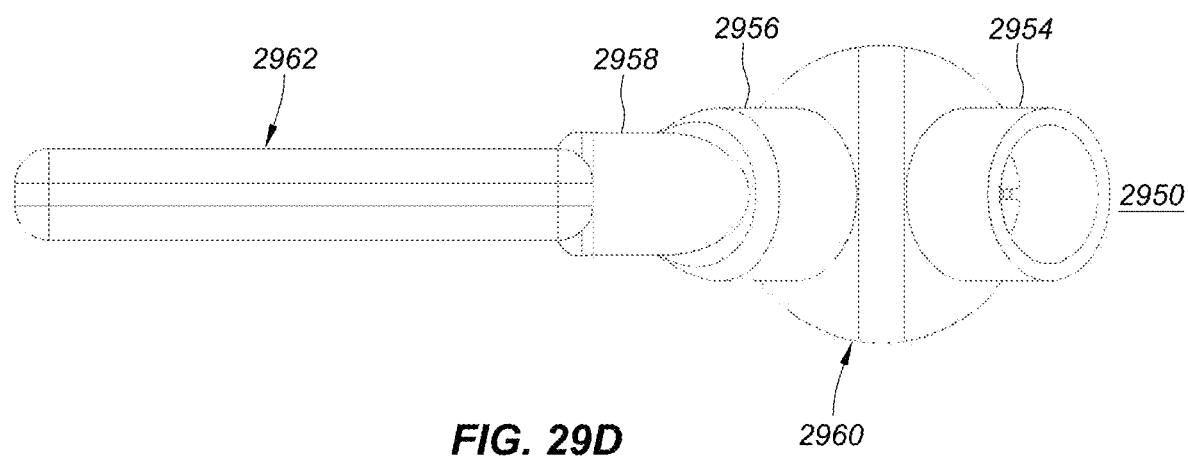
FIG. 29D is a bottom view of the reservoir bag and valve apparatus of FIG. 29A.
Figure 29E:
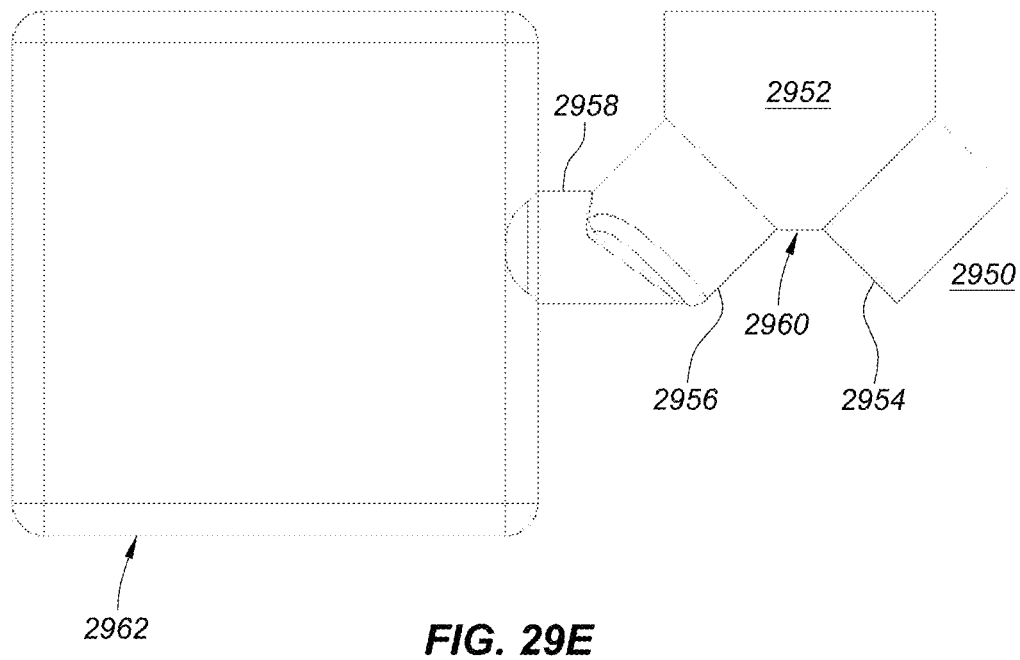
FIG. 29E is a side view of the reservoir bag and valve apparatus of FIG. 29A.
Figure 29F:
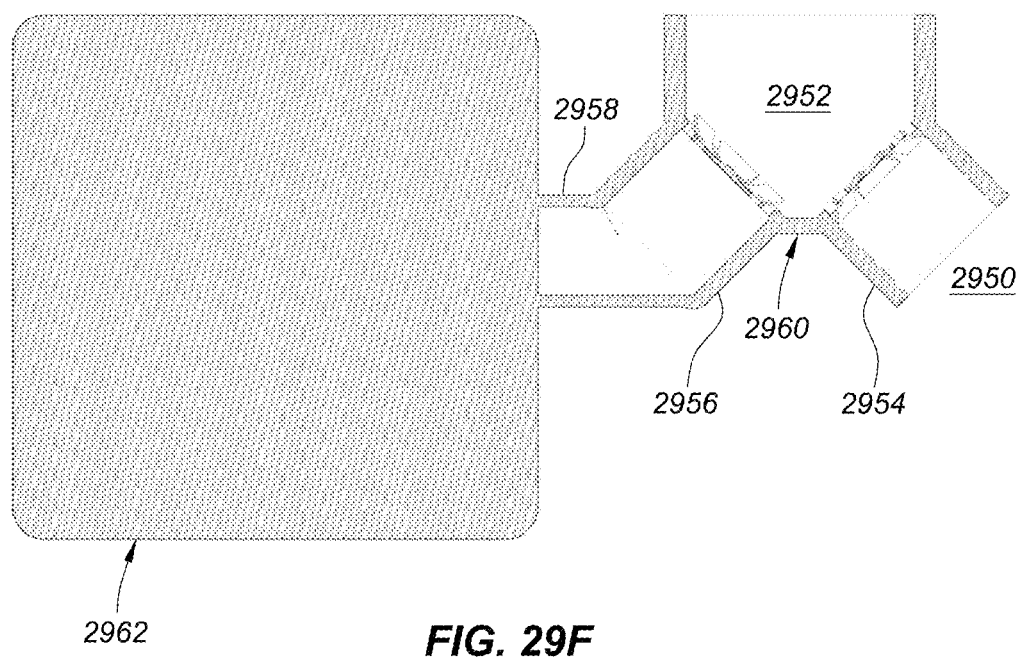
FIG. 29F is a side cutaway view of the reservoir bag and valve apparatus of FIG. 29A.
Figure 29G:
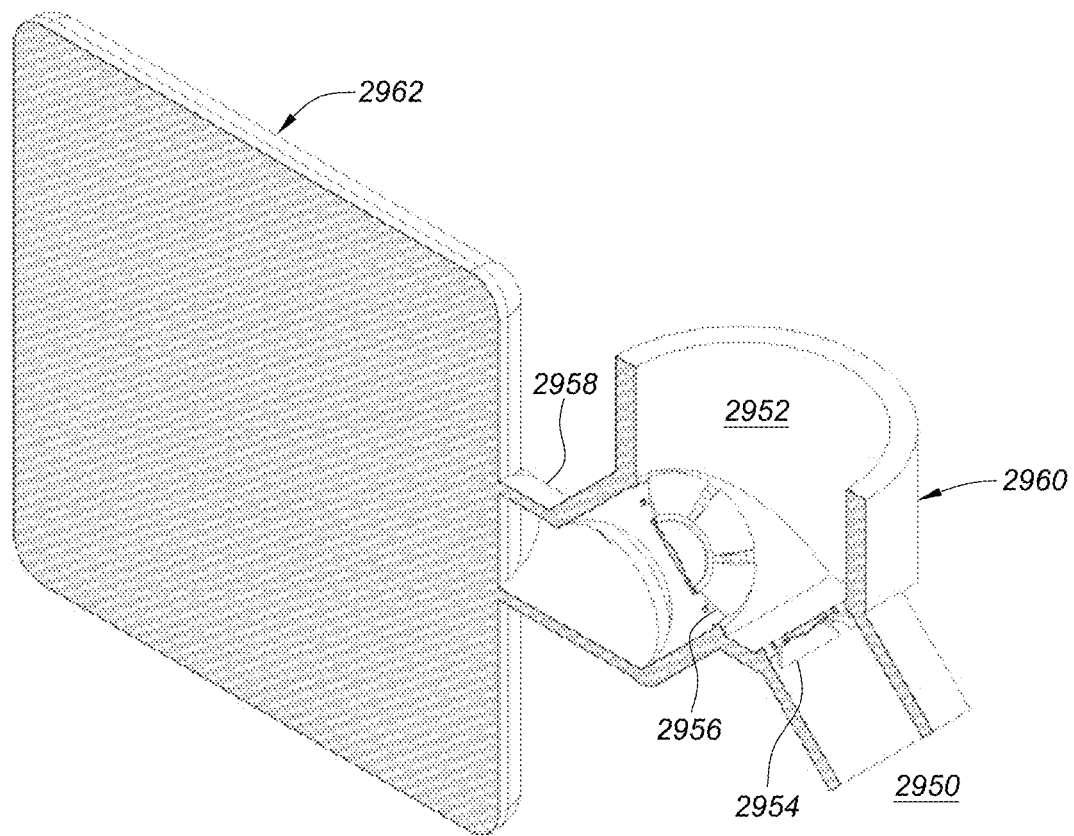
FIG. 29G is an upper perspective cutaway view of the reservoir bag and valve apparatus of FIG. 29A.

Referring now to FIG. 28, there is shown a flow diagram of the method according to the invention. The flow diagram comprises steps S1-S15 of the method. The flow diagram details a method of switching one fluid source with another fluid source and maintaining continuous fluid flow to a respirator or ventilator, comprising the steps of:

S1—providing a respirator or ventilator;
S2—providing one fluid source;
S3—attaching said one fluid source to one connector, said one connector comprising one housing and one connector mechanism for selectively starting and stopping the flow of fluid;
S4—providing an attachment device comprising a body having a fluid outlet port and at least two fluid inlet ports; wherein each fluid inlet port is connectable to a respective fluid source; wherein each fluid inlet port is in fluid communication with the fluid outlet port; and wherein each fluid inlet port comprises an attachment device mechanism for selectively starting and stopping the flow of fluid;

S5—providing a pressure regulator for regulating fluid pressure and fluid flow speed;

S6—connecting the fluid outlet port of the attachment device to the pressure regulator;

S7—connecting the pressure regulator to the respirator or ventilator;

S8—connecting said one connector to one fluid inlet port of the attachment device;

S9—selectively starting flow of fluid from said one fluid source to the respirator or ventilator using said one connector mechanism and one attachment device mechanism;

S10—providing another fluid source;

S11—attaching said another fluid source to another connector, said another connector comprising another housing and another connector mechanism for selectively starting and stopping the flow of fluid;

S12—connecting said another connector to another fluid inlet port of the attachment device;

S13—selectively starting flow of fluid from said another fluid source to the respirator or ventilator using said another connector mechanism and another attachment device mechanism;

S14—selectively stopping flow of fluid from said one fluid source to the respirator or ventilator using said one connector mechanism and said one attachment device mechanism; and S15—disconnecting said one connector from said one fluid inlet port of the attachment device.

In relation to the assembly 2781 shown in FIGS. 27A-27B, steps S1-S9 relate to FIGS. 27A-27B; steps S10-S13 relate to FIGS. 27C-27D, and steps S14-S15 relate to FIGS. 27E-27F.

Referring now to FIGS. 29A-29G, there is shown various views of a reservoir bag 2962 and valve apparatus 2960 formed according to an embodiment of the invention. The reservoir bag 2962 is made from a flexible and non-permeable material. Of course, it will be appreciated that in other embodiments, the bag may be non-flexible. The valve apparatus 2960 is connected to the reservoir bag 2962 by a screw fitting 2958 so that there is fluid communication between the reservoir bag 2962 and the valve apparatus 2960. The valve apparatus 2960 comprises a first one-way valve 2956 that fluidly connects the reservoir bag 2962 and the valve apparatus 2960, such that fluid from the reservoir bag 2962 can pass only in one direction from the reservoir bag 2962 to the valve apparatus 2960. The valve apparatus 2960 also comprises a second one-way valve 2954 so that fluid can only pass in one direction from inside 2952 of the valve apparatus 2960 to outside 2950 of the valve apparatus 2960. The second one-way valve 2954 acts as an exhaust valve. In this embodiment, the reservoir bag 2962 is filled with oxygen. In embodiments, it may be continually re-filled with oxygen to maintain a constant supply to a patient, for instance.

Figure 30A:
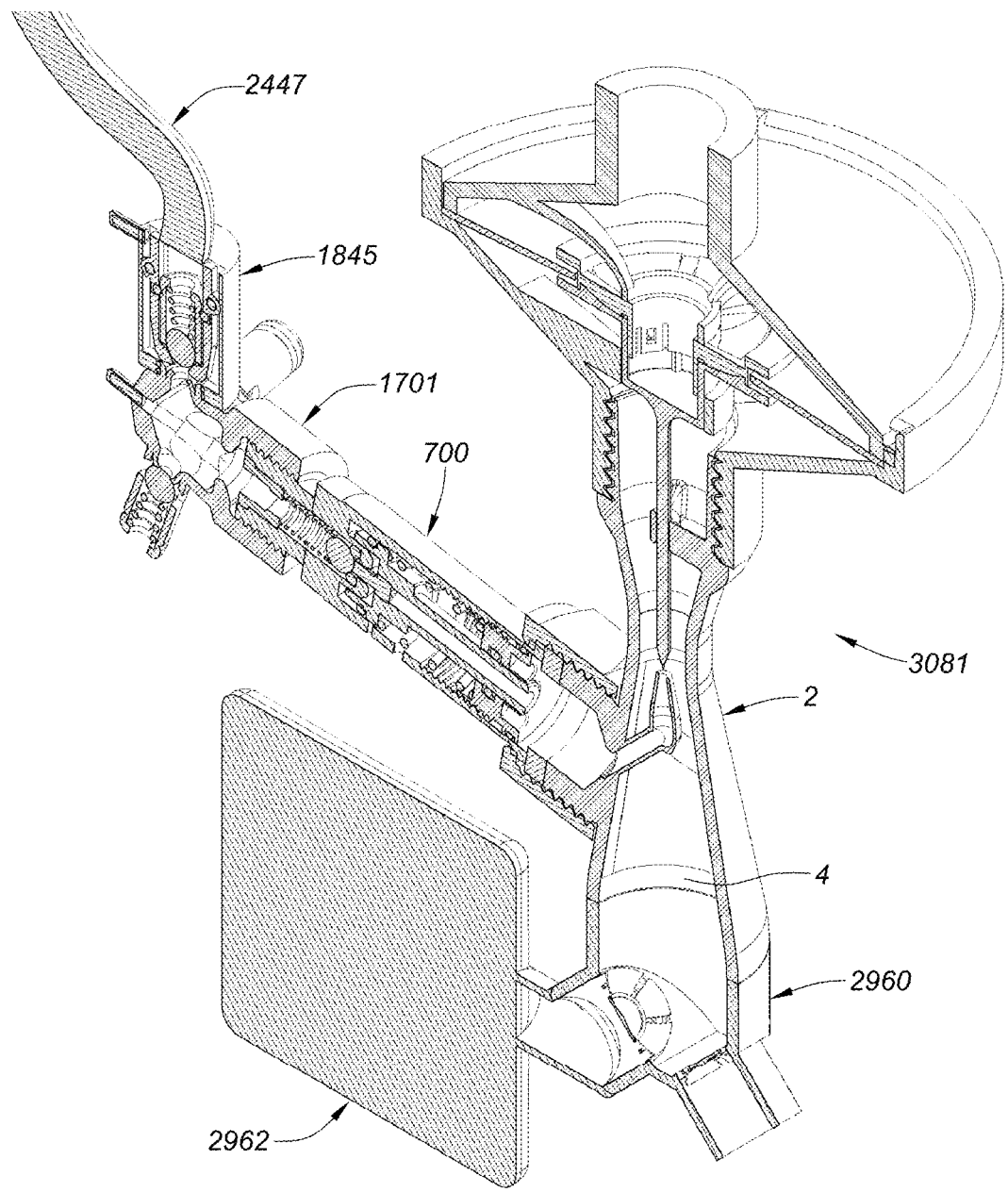
FIG. 30A is a perspective cutaway view of an assembly formed according to an embodiment of the invention comprising a reservoir bag and valve apparatus in an engaged position.
Figure 30B:
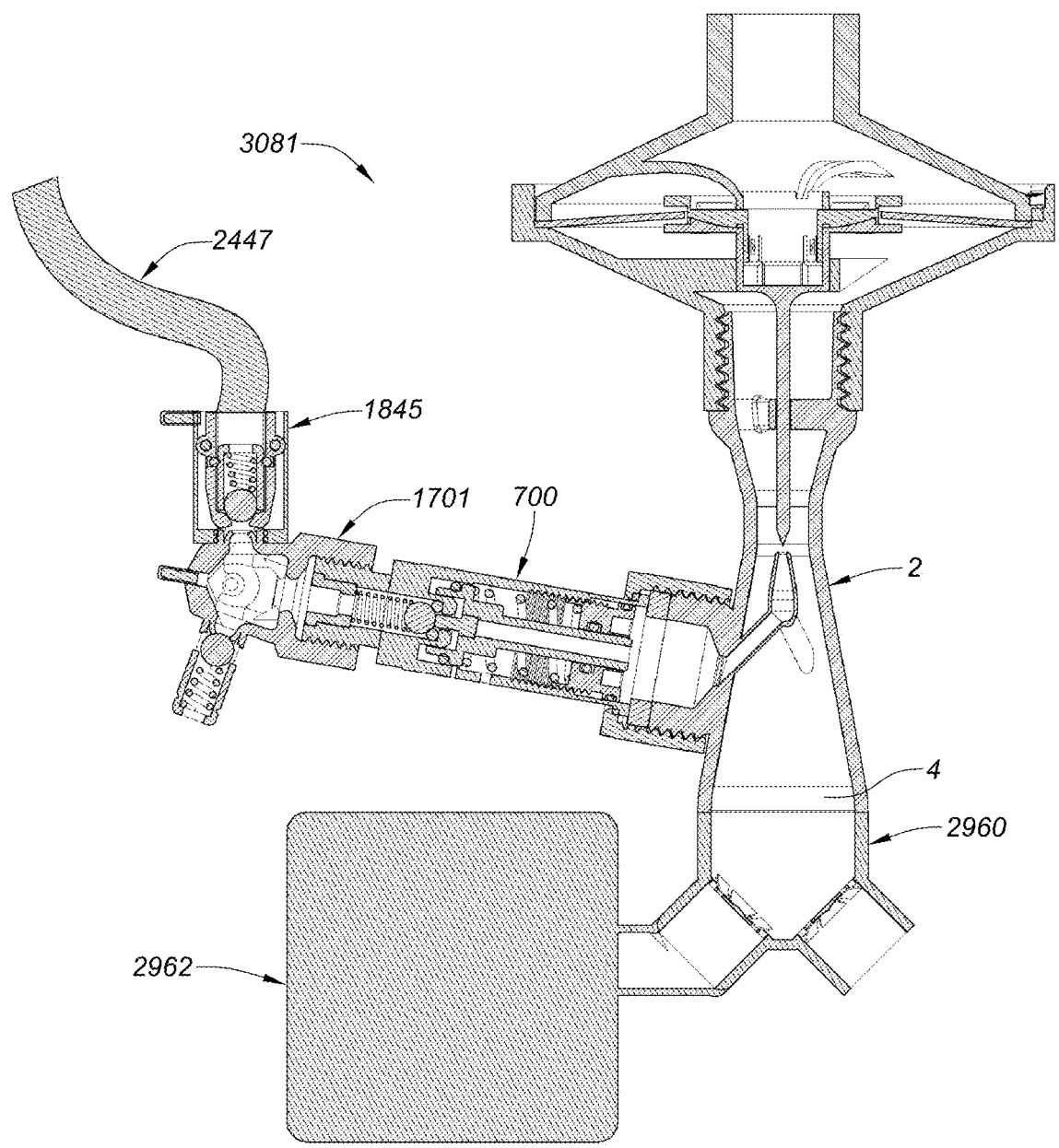
FIG. 30B is a side cutaway view of the assembly of FIG. 30A in the engaged position.

Referring now to FIGS. 30A-30B, there is shown a perspective cutaway view and side cutaway view of an assembly generally indicated 3081 in an engaged position formed according to an embodiment of the invention, respectively. The assembly 3081 is the same as that shown in FIGS. 27A-27F comprising the attachment device 1701 of FIGS. 17A-17G, the connector 1845 of FIGS. 18A-18B, the pressure regulator 700 of FIGS. 9-14, the ventilator of FIGS. 1-4, except the assembly 3081 further comprises the reservoir bag 2962 and valve apparatus 2960 of FIGS. 29A-29G. The ambient fluid aperture 4 of the ventilator 2 is hermetically connected to the valve apparatus 2960. During operation, in the open valve/start flow state of the various components described herein, fluid can pass from the fluid source 2447, into the connector 1845, through to the attachment device 1701, through the pressure regulator 700, and into the ventilator 2. The assembly 3081 is shown in the open flow state. When a patient inhales through the ventilator 2, oxygen from the reservoir bag 2962 is entrained in the pressure-controlled oxygen flow in the venturi instead of the entrainment of ambient fluid, as described in earlier embodiments of the ventilator 2. In this way, the patient can receive a 100% oxygen need based on their needs.

Referring now to FIGS. 31A-31I, there is shown various views of an attachment device generally indicated 3101. The attachment device 3101 comprising a body 3103 having a fluid outlet port 3105 and, in this embodiment, two fluid inlet ports 3107. It will be understood that in other embodiments, the attachment device may have more than two fluid inlet ports. Each fluid inlet port 3107 is connectable to a respective fluid source (not shown). Each fluid inlet port 3107 is in fluid communication with the fluid outlet port 3105. A fluid may thus travel into the attachment device 3101 via one of the fluid inlet ports 3107 and out via the fluid outlet port 3105, when allowed by the attachment device mechanism(s) 3109. Each fluid inlet port 3107 comprises an attachment device mechanism 3109 for selectively starting and stopping the flow of fluid from the respective fluid source (not shown) to the fluid outlet port 3105.

In this embodiment, the body 3103 is in the form of a short hollow cylinder 3111 with a hollow ring 3164 located at the end thereof. The hollow ring 3164 creates a groove on the external surface of the short hollow cylinder 3111 thereby facilitating the attachment of a bronchoscope port plug (not shown) or suction catheter port plug (not shown) in the groove by a connection cable (not shown). Of course, it will be appreciated that the body can take any suitable shape. In this embodiment, each fluid inlet port 3107 comprises an arm 3115 extending from the body 3103. More specifically, each arm 3115 extends laterally from the body 3103 and together they define a T-shape with the body 3103. Each arm 3115 is shaped as an elongate hollow cylinder 3119 having an access hole 3121 at one enlarged cylindrical limiter end 3123 for receiving fluid from a respective fluid source (not shown). Towards the other end 3125 of the elongate hollow cylinder 3119 there is provided a circular aperture 3127, which in this embodiment are circular holes that are cut out of the wall of each of the elongate hollow cylinders 3119. The enlarged cylindrical limiter end 3123 is suitable for use with a ventilator connector, such as an multi adaptor having standard dimensions 15 mm ID×22 mm OD.

The attachment device 3101 also comprises a suction catheter port 3166 having a suction catheter access hole 3168. In this embodiment, the suction catheter port 3166 is a hollow cylinder extending upwardly from the body 3103 so that suction catheter port 3166 and body 3103 lie in the same longitudinal axis. The suction catheter port 3166 is in fluid communication with the fluid outlet port 3105. The suction catheter access hole 3168 is located at the end of the suction catheter port 3166 and provides access to a suction catheter, for instance, during use of the attachment device 3101 by an operator such as a healthcare professional, for instance. The suction catheter port 3166 has a size suitable for fitting to a catheter, such as a closed suction catheter, of French Size 14.

The attachment device 3101 also comprises a bronchoscope port 3170 having a bronchoscope access hole 3172. In this embodiment, the bronchoscope port is a hollow cylinder extending diagonally upwardly from the body 3103 so that bronchoscope port 3166 is slightly angled away from the longitudinal axis of the body 3103. The bronchoscope port 3166 is in fluid communication with the fluid outlet port 3105. The bronchoscope access hole 3168 is located at the end of the bronchoscope port 3166 and provides access to a bronchoscope, for instance, during use of the attachment device 3101 by an operator such as a healthcare professional, for instance.

Figure 31A:
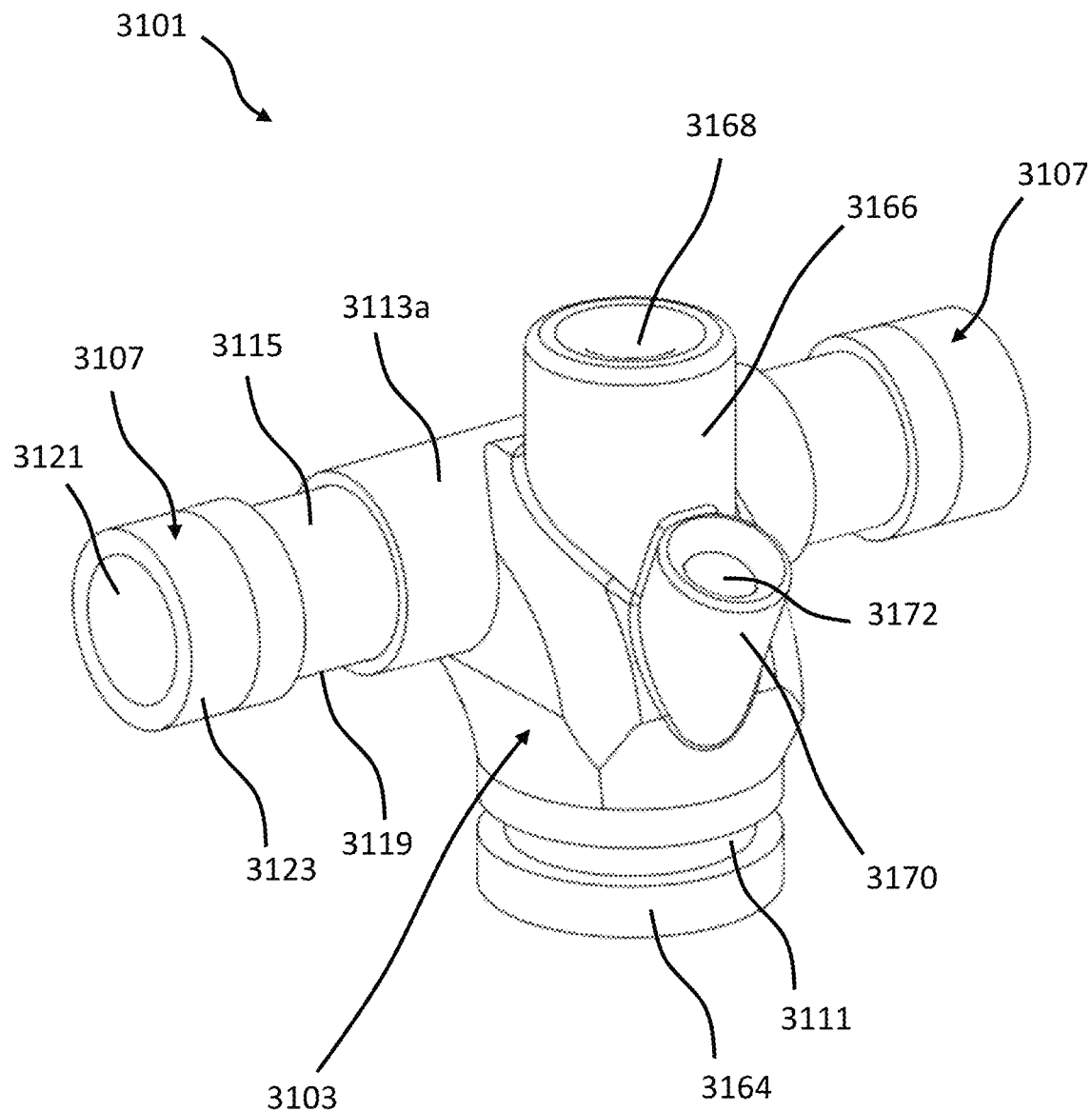
FIG. 31A is an upper perspective front view of an attachment device formed according to an embodiment of the invention in which there are two fluid inlet ports.
Figure 31B:
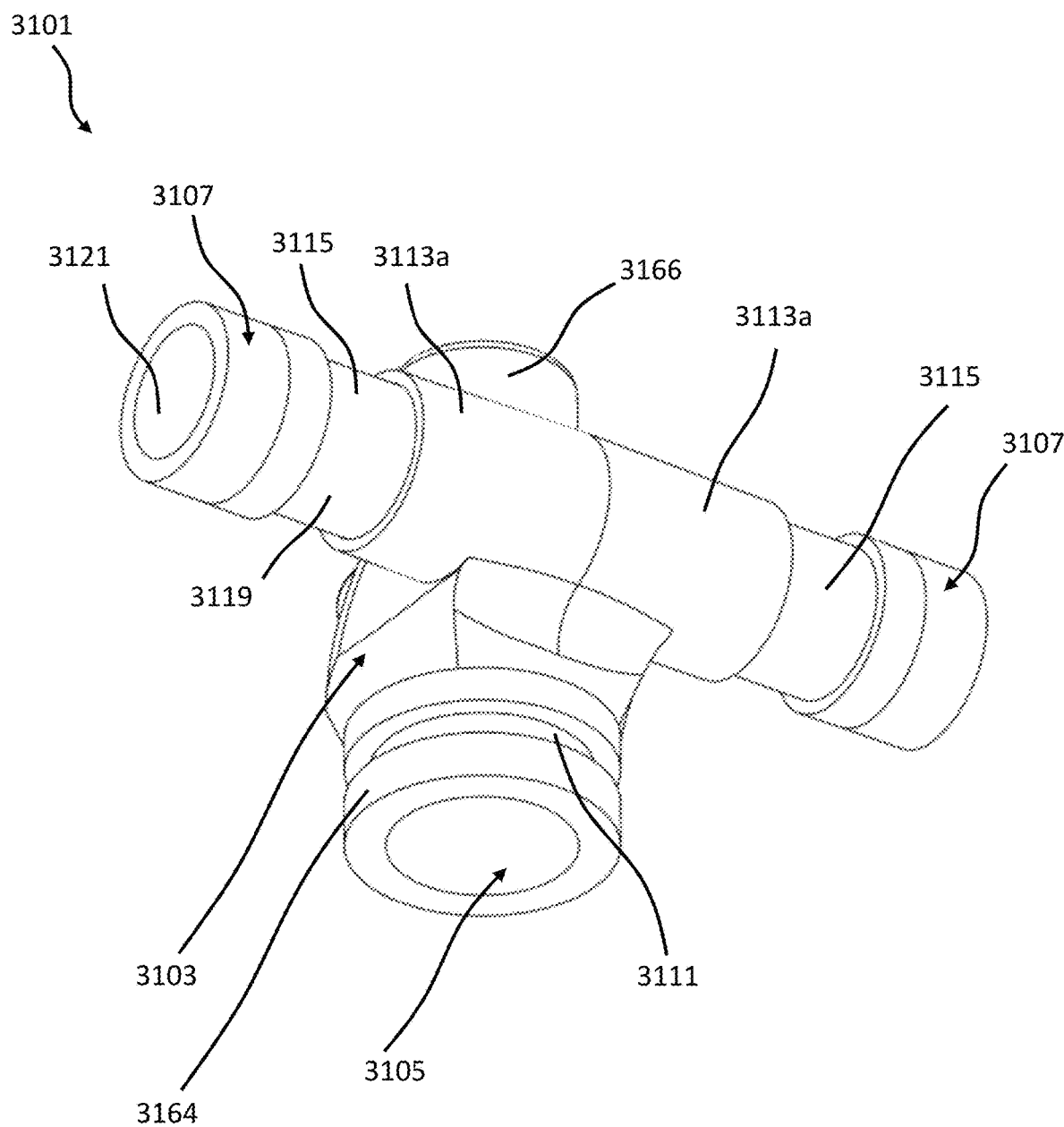
FIG. 31B is a lower perspective rear view of the attachment device of FIG. 31A.
Figure 31C:
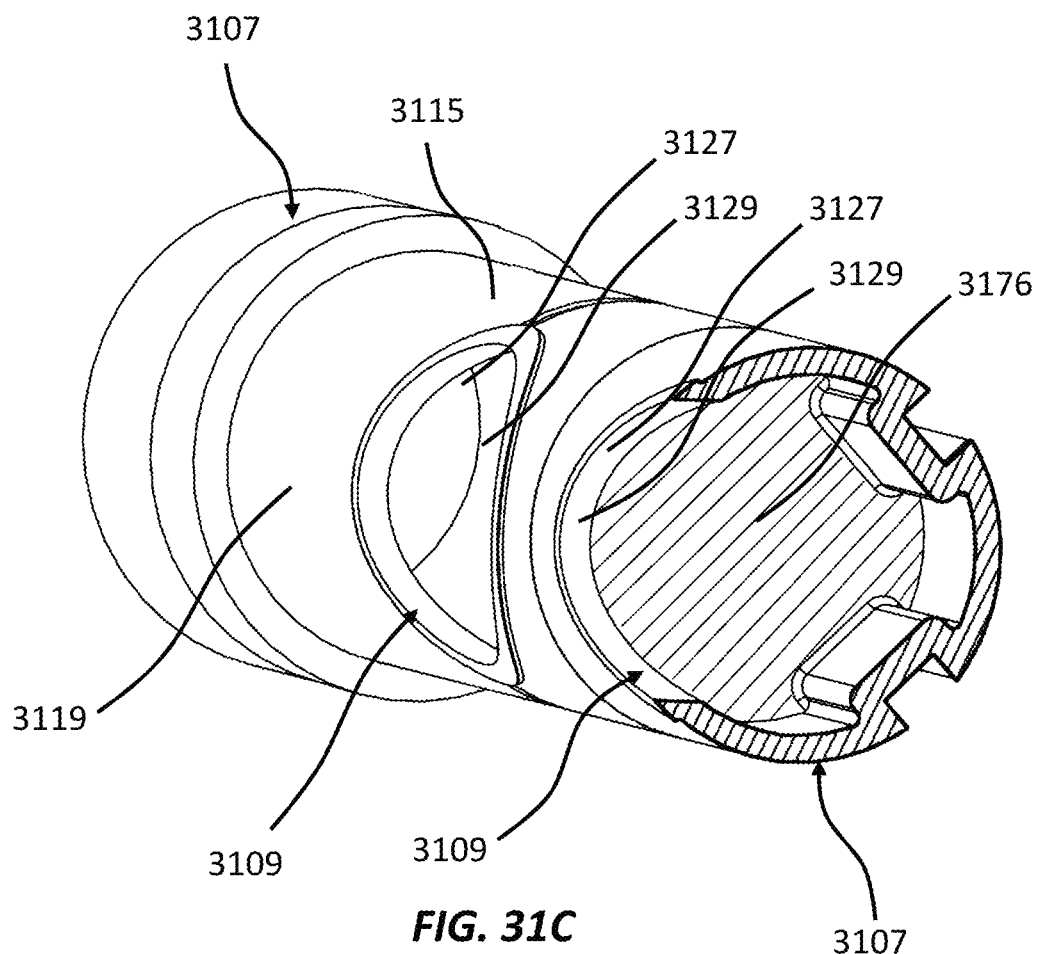
FIG. 31C is an upper perspective rear cutaway view of the obstructor of FIG. 31A.

As best seen in FIG. 31C, there is shown that each fluid inlet port 3107 comprises an attachment device mechanism 3109 for selectively starting and stopping the flow of fluid from the respective fluid source (not shown) to the fluid outlet port 3105. In this embodiment, the attachment device mechanism 3109 comprises a valve 3129 comprising the circular aperture 3127, the obstructor 3119 (constituted in this embodiment by the elongate hollow cylinder 3119) and the fluid access port 3178 (see FIG. 31D), which valve 3129 is moveable between an open valve position (shown in later figures) and a closed valve position (shown in later figures). The two linearly aligned fluid inlet ports 3107 are separated by a partition (wall) 3176 thereby preventing fluid from passing directly from one fluid inlet port 3107 to the other fluid inlet port 3107.

Figure 31D:
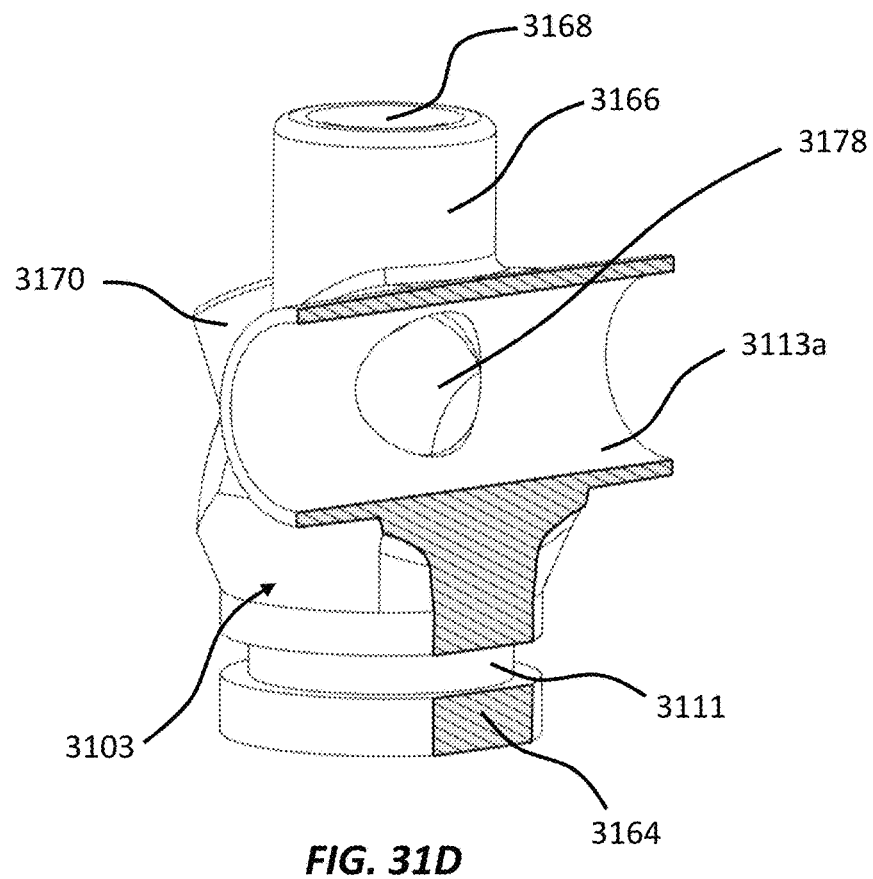
FIG. 31D is an upper perspective rear cutaway view of the body and obstructor holder of FIG. 31A.

Referring now to FIG. 31D, there is shown an upper perspective rear cutaway view of the body 3103 and obstructor holder 3113a of FIG. 31A. The obstructor holder 3113a is short hollow cylinder and sits perpendicularly connected at the top of the body 3103. The obstructor holder's dimensions are such that its diameter is slightly larger than that of the obstructors 3119 so that they may move linearly by sliding within the internal wall of the obstructor holder 3113a.

Figure 31E:
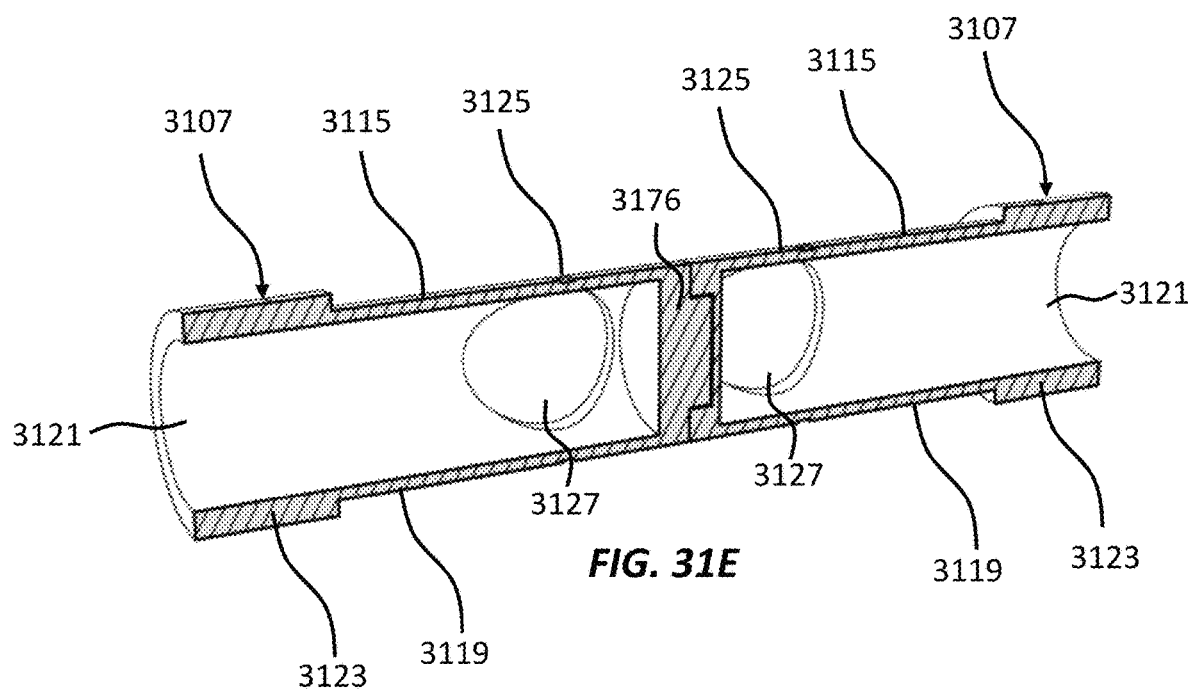
FIG. 31E is an upper perspective rear cutaway view of the obstructor of FIG. 31A.

Referring now to FIG. 31E, there is shown is an upper perspective rear cutaway view of the two linearly aligned and connected obstructors 3107 of FIG. 31A.

Figure 31F:
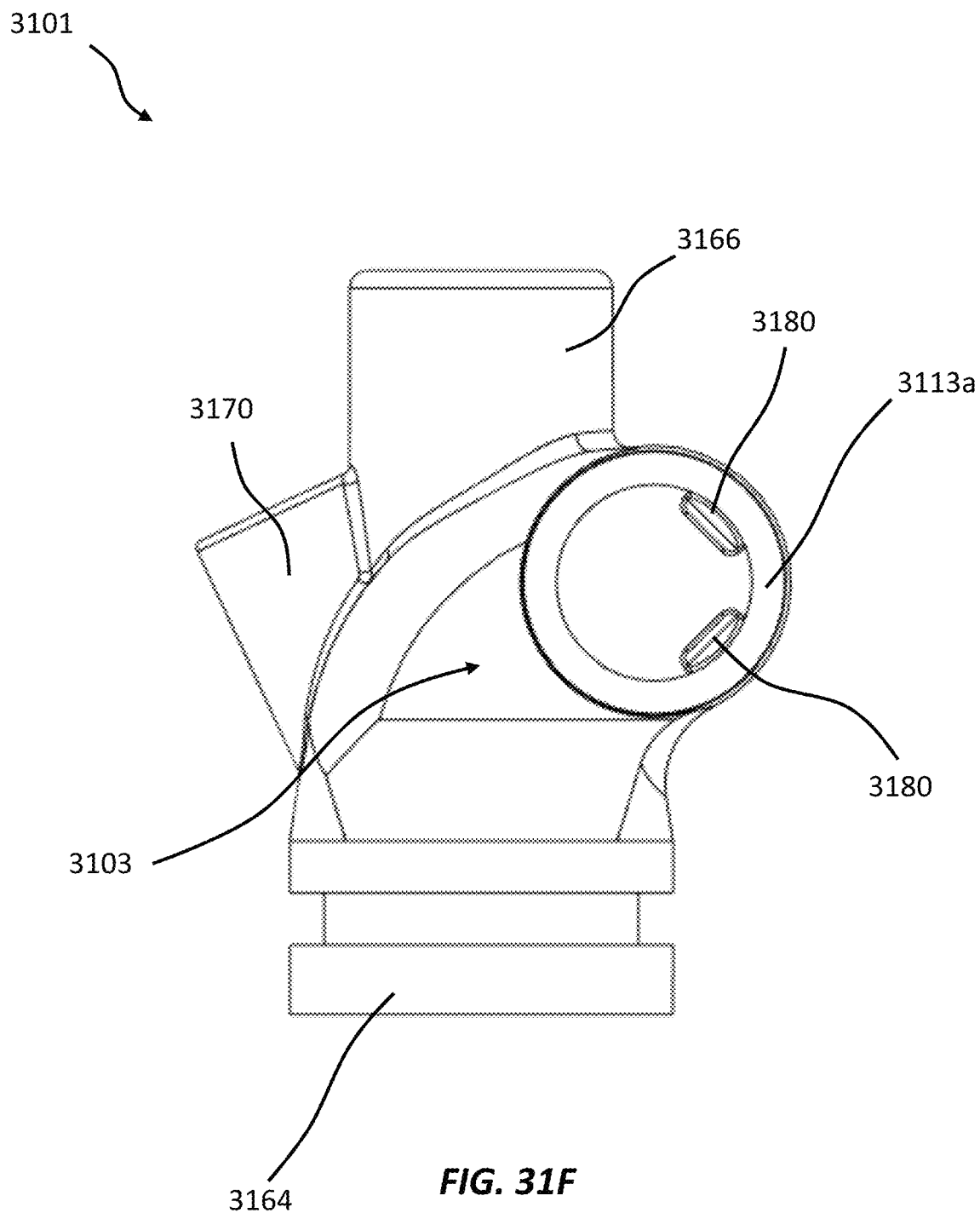
FIG. 31F is a side cutaway view of the attachment device of FIG. 31A.

Referring now to FIG. 31F, there is shown is a side cutaway view of the attachment device of FIG. 31A having the obstructor holder 3113a (obstructors not shown). The internal wall of the obstructor holder 3113a comprises two anti-rotation protrusions 3180 which fit inside two corresponding recesses (not shown) on the external wall of the obstructors 3107.

Figure 31G:
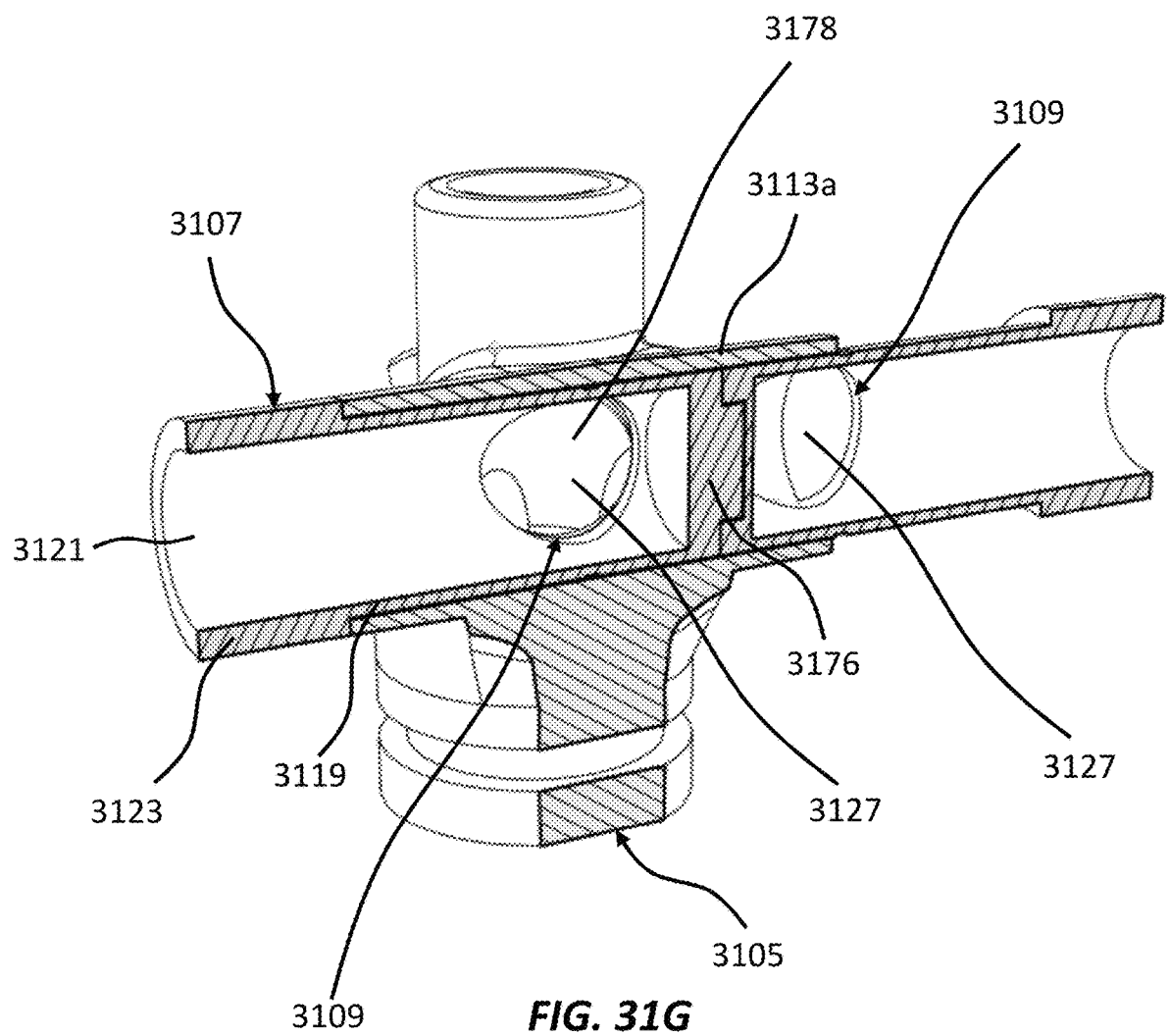
FIG. 31G is an upper perspective rear cutaway view of the attachment device of FIG. 31A in a first position.
Figure 31H:
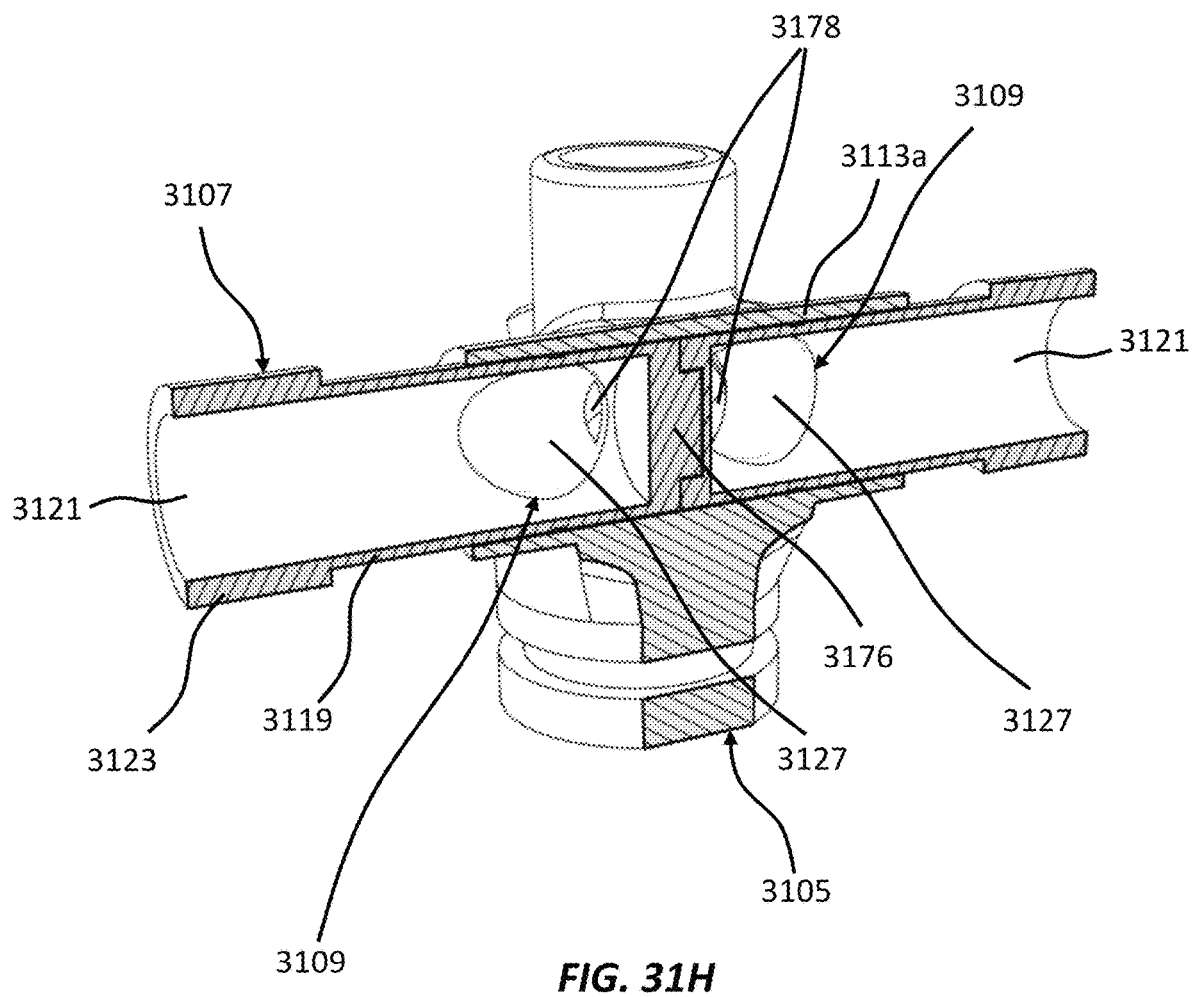
FIG. 31H is an upper perspective rear cutaway view of the attachment device of FIG. 31A in a second position.
Figure 31I:
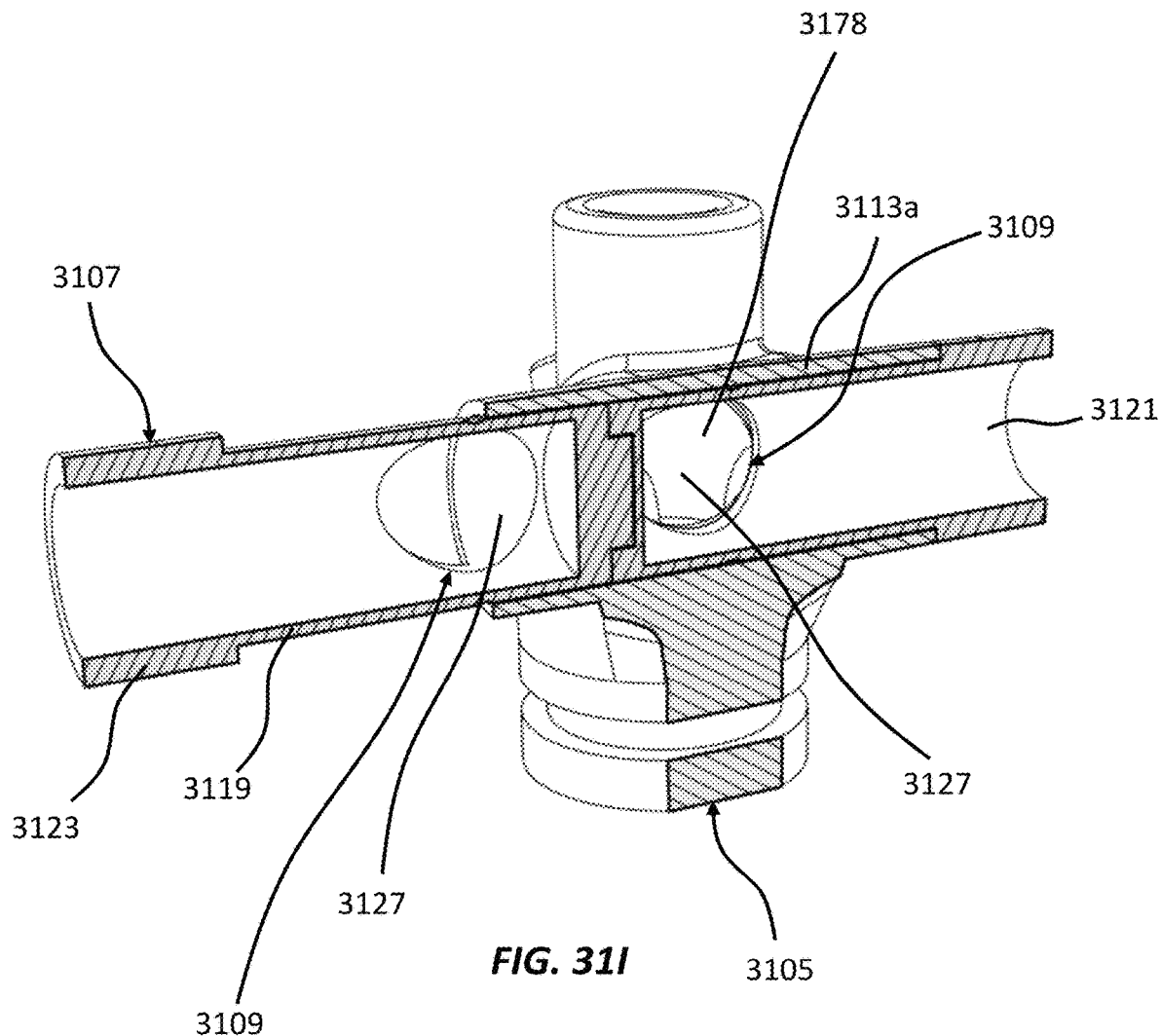
FIG. 31I is an upper perspective rear cutaway view of the attachment device of FIG. 31A in a third position.

Turning now to the operation of the attachment device 3101, this is best seen in FIG. 31G to FIG. 31I, which show an upper perspective rear cutaway view of the attachment device 3101 of FIG. 31A in a first position, second position, and third position, respectively.

FIG. 31G shows the attachment device 3101 in the first position. In the first position, the obstructor 3119 (constituted in this embodiment by the elongate hollow cylinder 3119) sits inside the obstructor holder 3113a and has been slid across to the right hand side as viewed in FIG. 31G. The end position of the obstructor 3119 is governed by the enlarged cylindrical limiter end 3123 of the left hand side obstructor 3119 because the diameter of the enlarged cylindrical limiter end 3123 is the same diameter as that of the obstructor holder 3113a such that once the enlarged cylindrical limiter end 3123 abuts the edge of the obstructor holder 3113a, it restricts any further linear movement of the obstructor 3119 (both fluid inlet ports 3107) in that direction towards the right hand side. In the first position, there is shown both the left hand side and right hand side attachment device mechanisms 3109 for selectively starting and stopping the flow of fluid from the respective fluid source (not shown) to the fluid outlet port 3105. In this embodiment, the left hand side attachment device mechanism 3109 comprises a valve 3129 comprising the circular aperture 3127, the obstructor 3119 (constituted in this embodiment by the elongate hollow cylinder 3119) and the fluid access port 3178, and shows the valve 3129 of the left hand side attachment device mechanism 3109 in the open position because left hand side circular aperture 3127 is aligned with the fluid access port 3178 thereby forming a passage for fluid to flow from a left hand side fluid source (not shown) via access hole 3121, through the left hand side circular aperture 3127, through the fluid access port 3178, and out of the fluid outlet port 3105. In the first position, the right hand side attachment device mechanism 3109 valve 3129 is closed because the right hand side circular aperture 3127 is not aligned with the fluid access port 3178, and due to the partition (wall) 3176 only fluid from the left hand side fluid source (not shown) is able to reach the fluid outlet port 3105 in the first position. In this way, the supply of fluid constitutes a ratio of 100%:0% because the attachment device 3101 is providing the fluid from the first fluid source (100% of first fluid supply and 0% of second fluid supply).

FIG. 31H shows the attachment device 3101 in the second position. In the second position, the obstructor 3119 (constituted in this embodiment by the elongate hollow cylinder 3119) sits inside the obstructor holder 3113a and has been slid from right to left and sits in the middle of the obstructor holder 3113a as viewed in FIG. 31H. In the second position, there is shown both the left hand side and right hand side attachment device mechanisms 3109 for selectively starting and stopping the flow of fluid from the respective fluid source (not shown) to the fluid outlet port 3105. In this embodiment, both the left hand side and right hand side attachment device mechanisms 3109 comprises a respective valve 3129 comprising the circular aperture 3127, the obstructor 3119 (constituted in this embodiment by the elongate hollow cylinder 3119) and the fluid access port 3178, and shows both valves 3129 of the left hand side and right hand side attachment device mechanisms 3109 in the (partially) open position because both the left hand side and right hand side circular apertures 3127 are aligned with the fluid access port 3178 thereby forming a passage for fluid to flow from both the left hand side and right hand side fluid sources (not shown) via left hand side and right hand side access holes 3121, through the left hand side and right hand side circular apertures 3127, through the left hand side and right fluid side access ports 3178, and out of the fluid outlet port 3105. In the second position, both the left hand side and the right hand side attachment device mechanisms 3109 have valves 3129 in the open position (at least partially). In this way, the supply of fluid constitutes a ratio, in this embodiment, of 50%:50% because the attachment device 3101 is concurrently providing the fluid from first fluid source and the second fluid source (i.e 50% of first fluid supply and 50% of second fluid supply).

FIG. 31I shows the attachment device 3101 in the third position. In the third position, the obstructor 3119 (constituted in this embodiment by the elongate hollow cylinder 3119) sits inside the obstructor holder 3113a and has been slid across to the left hand side as viewed in FIG. 31I. The end position of the obstructor 3119 is governed by the enlarged cylindrical limiter end 3123 of the right hand side obstructor 3119 because the diameter of the enlarged cylindrical limiter end 3123 is the same diameter as that of the obstructor holder 3113a such that once the enlarged cylindrical limiter end 3123 abuts the edge of the obstructor holder 3113a, it restricts any further linear movement of the obstructor 3119 (both fluid inlet ports 3107) in that direction towards the left hand side. In the third position, there is shown both the left hand side and right hand side attachment device mechanisms 3109 for selectively starting and stopping the flow of fluid from the respective fluid source (not shown) to the fluid outlet port 3105. In this embodiment, the right hand side attachment device mechanism 3109 comprises a valve 3129 comprising the circular aperture 3127, the obstructor 3119 (constituted in this embodiment by the elongate hollow cylinder 3119) and the fluid access port 3178, and shows the valve 3129 of the right hand side attachment device mechanism 3109 in the open position because right hand side circular aperture 3127 is aligned with the fluid access port 3178 thereby forming a passage for fluid to flow from a right hand side fluid source (not shown) via access hole 3121, through the right hand side circular aperture 3127, through the fluid access port 3178, and out of the fluid outlet port 3105. In the third position, the left hand side attachment device mechanism 3109 valve 3129 is closed because the left hand side circular aperture 3127 is not aligned with the fluid access port 3178, and due to the partition (wall) 3176 only fluid from the right hand side fluid source (not shown) is able to reach the fluid outlet port 3105 in the third position. In this way, the supply of fluid constitutes a ratio of 0%:100% because the attachment device 3101 is providing the fluid from second fluid source (0% of first fluid supply and 100% of second fluid supply).

FIG. 31G to FIG. 31I demonstrate how the attachment device can be used to transfer/switch supply of fluid from a first fluid source to supply from a second fluid source without compromising the fluid flow and/or fluid pressure.

Referring now to FIGS. 32A-32H, there is shown various views of an attachment device generally indicated 3201. The attachment device 3201 comprising a body 3203 having a fluid outlet port 3205 and, in this embodiment, two fluid inlet ports 3207. It will be understood that in other embodiments, the attachment device may have more than two fluid inlet ports. Each fluid inlet port 3207 is connectable to a respective fluid source (not shown). Each fluid inlet port 3207 is in fluid communication with the fluid outlet port 3205. A fluid may thus travel into the attachment device 3201 via one of the fluid inlet ports 3207 and out via the fluid outlet port 3205, when allowed by the attachment device mechanism(s) 3209. Each fluid inlet port 3207 comprises an attachment device mechanism 3209 for selectively starting and stopping the flow of fluid from the respective fluid source (not shown) to the fluid outlet port 3205.

In this embodiment, the body 3203 is in the form of a short hollow cylinder 3211 with a ball handle 3282 located at the top thereof. The ball handle 3283 comprises a proximal end 3286 and distal end 3288 and can be gripped by an operator to turn the ball handle 3282 and consequently the ball 3284. The proximal end 3286 comprises a fluid path indicator 3294 to show the operator which path of the fluid is taking through the attachment device 3201 depending on the current position of the ball handle 3288. The ball handle 3282 facilitates rotational movement of the ball 3284 located inside the body 3203. Of course, it will be appreciated that the body 3203 can take any suitable shape. In this embodiment, each fluid inlet port 3107 comprises an arm 3215 extending from the body 3203. More specifically, each arm 3215 extends laterally from the body 3203, are in the same plane, and angled approximately 120 degrees from one another in the same plane. Each arm 3215 is shaped as an elongate hollow cylinder 3219 having an access hole 3121 for receiving fluid from a respective fluid source (not shown). Each fluid inlet port 3207 is suitable for use with a ventilator connector, such as an multi adaptor having standard dimensions 15 mm ID×22 mm OD.

The attachment device 3201 also comprises a suction catheter port 3266 having a suction catheter access hole 3268. In this embodiment, the suction catheter port 3266 is a hollow cylinder extending upwardly from the body 3203 so that suction catheter port 3266 and body 3203 lie in the same longitudinal axis. The suction catheter port 3266 is in fluid communication with the fluid outlet port 3205. The suction catheter access hole 3268 is located at the end of the suction catheter port 3266 and provides access to a suction catheter, for instance, during use of the attachment device 3201 by an operator such as a healthcare professional, for instance. The suction catheter port 3266 has a size suitable for fitting to a catheter, such as a closed suction catheter, of French Size 14.

The attachment device 3201 also comprises a bronchoscope port 3270 having a bronchoscope access hole 3272. In this embodiment, the bronchoscope port is a hollow cylinder extending diagonally upwardly from the body 3203 so that bronchoscope port 3266 is slightly angled away from the longitudinal axis of the body 3203. The bronchoscope port 3266 is in fluid communication with the fluid outlet port 3205. The bronchoscope access hole 3268 is located at the end of the bronchoscope port 3266 and provides access to a bronchoscope, for instance, during use of the attachment device 3201 by an operator such as a healthcare professional, for instance.

Figure 32A:
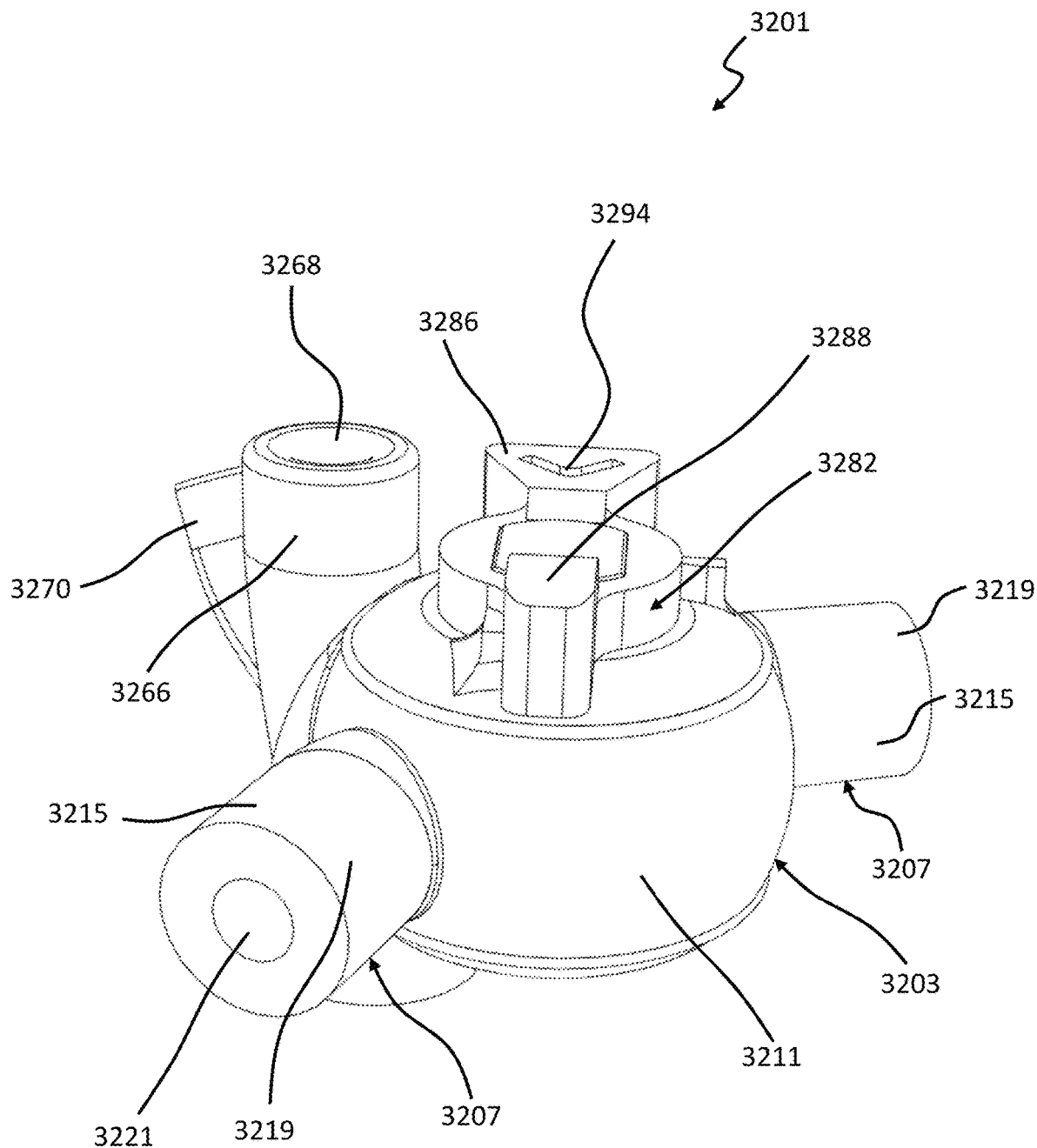
FIG. 32A is an upper perspective front view of an attachment device formed according to an embodiment of the invention in which there are two fluid inlet ports.
Figure 32B:
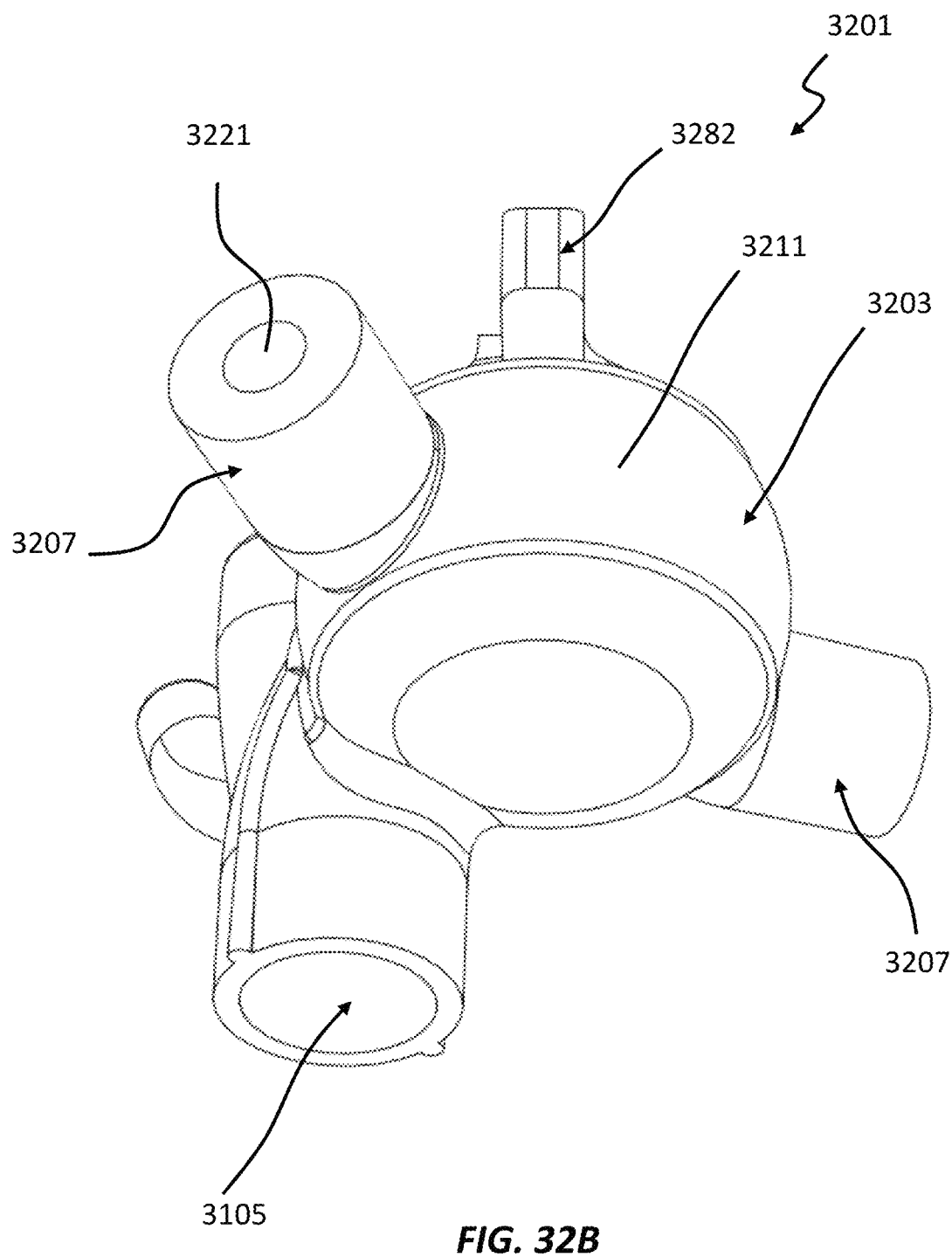
FIG. 32B is a lower perspective rear view of the attachment device of FIG. 32A.
Figure 32C:
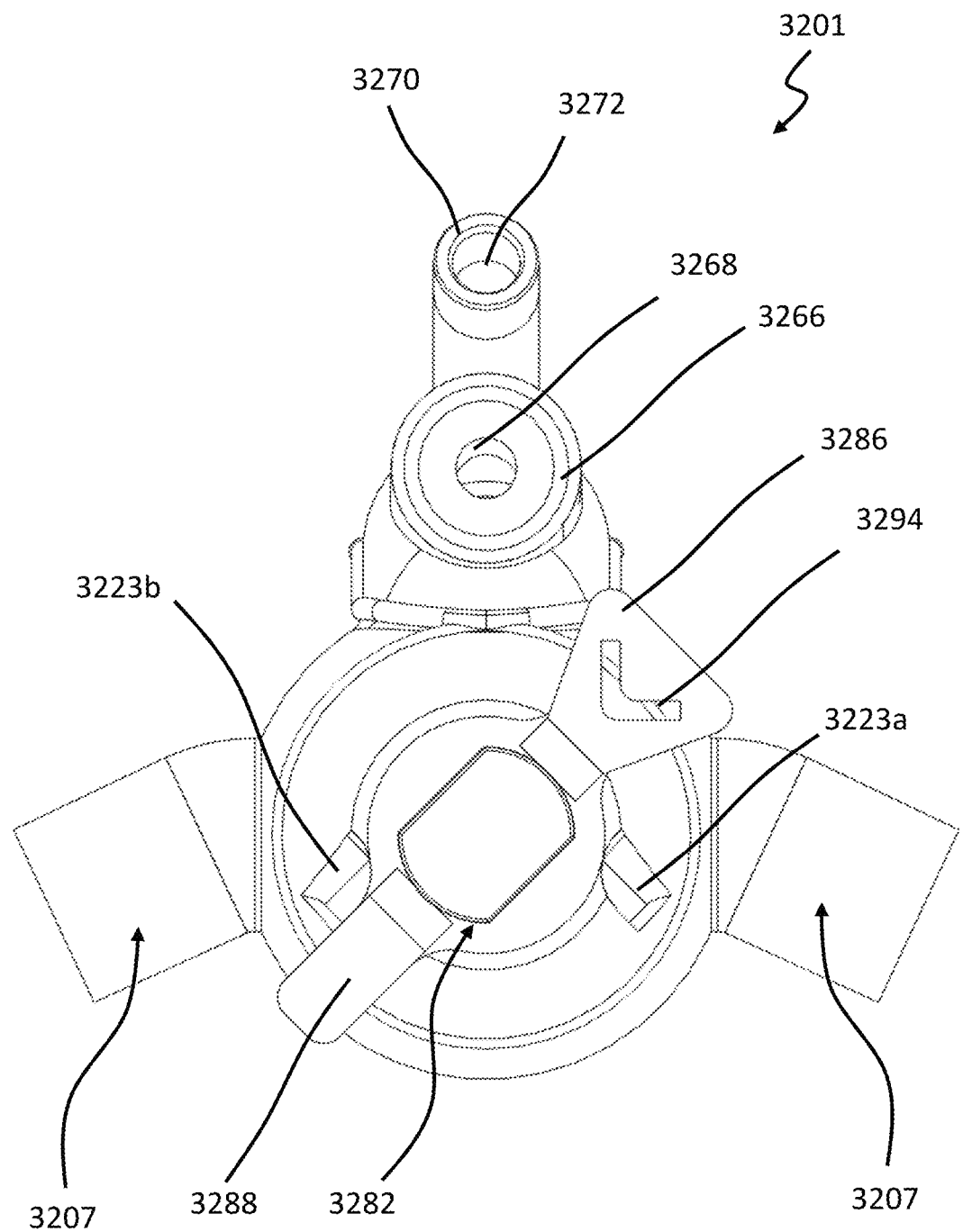
FIG. 32C is a plan view of the attachment device of FIG. 32A.
Figure 32D:
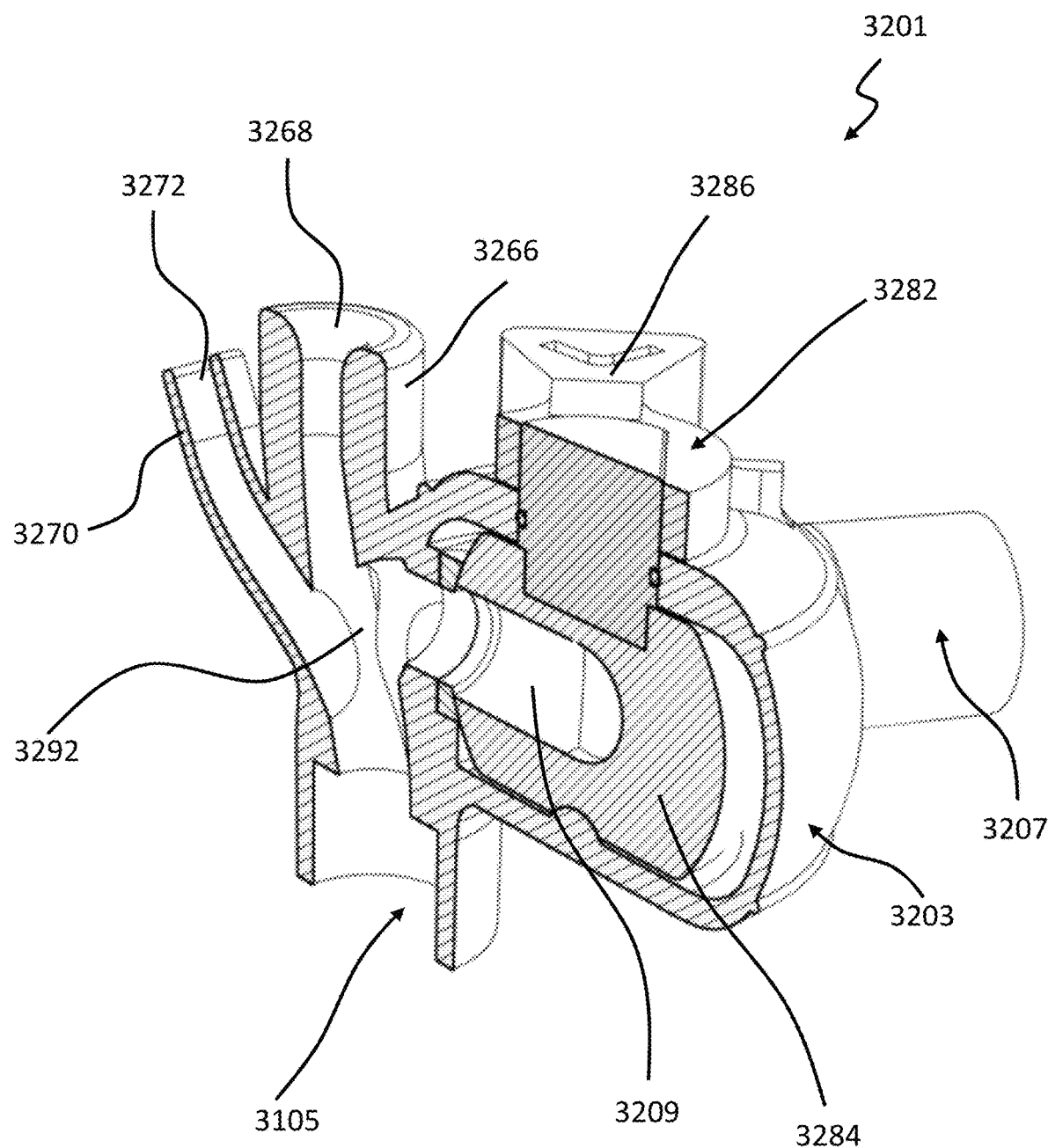
FIG. 32D is an upper perspective front cutaway view of the attachment device of FIG. 32A.
Figure 32E:
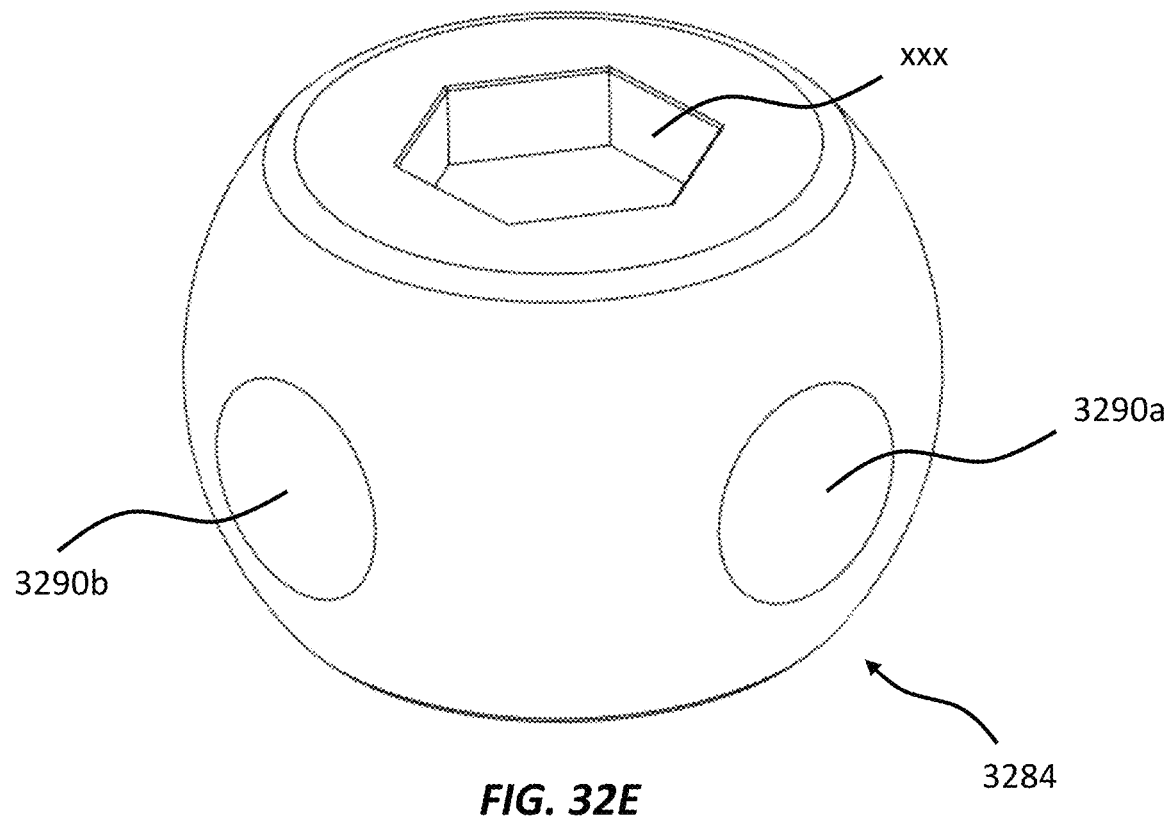
FIG. 32E is an upper perspective front view of the obstructor of FIG. 32A.
Figure 32F:
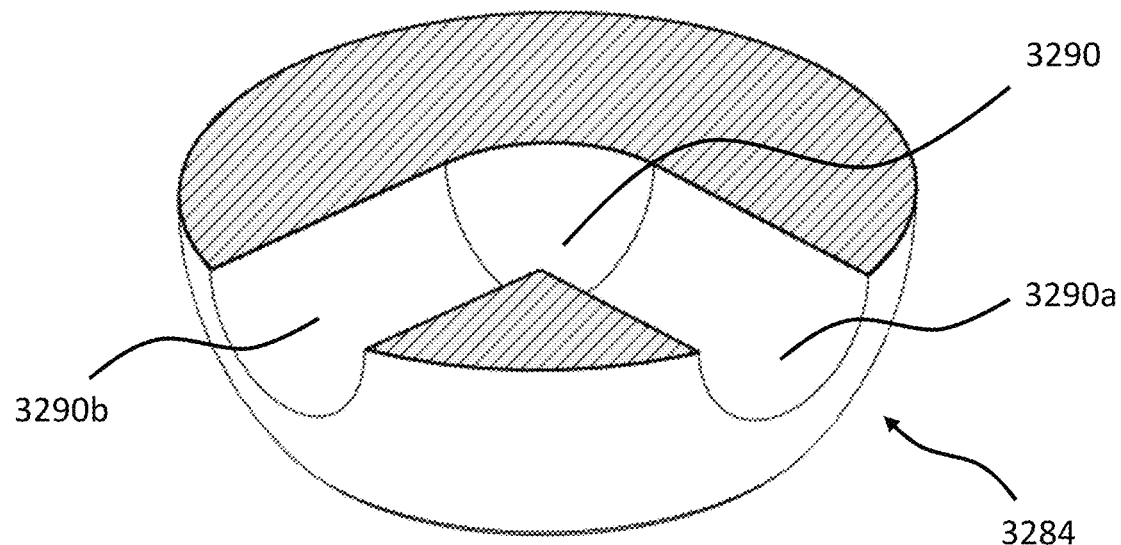
FIG. 32F is an upper perspective front cutaway view of the obstructor of FIG. 32E.
Figure 32G:
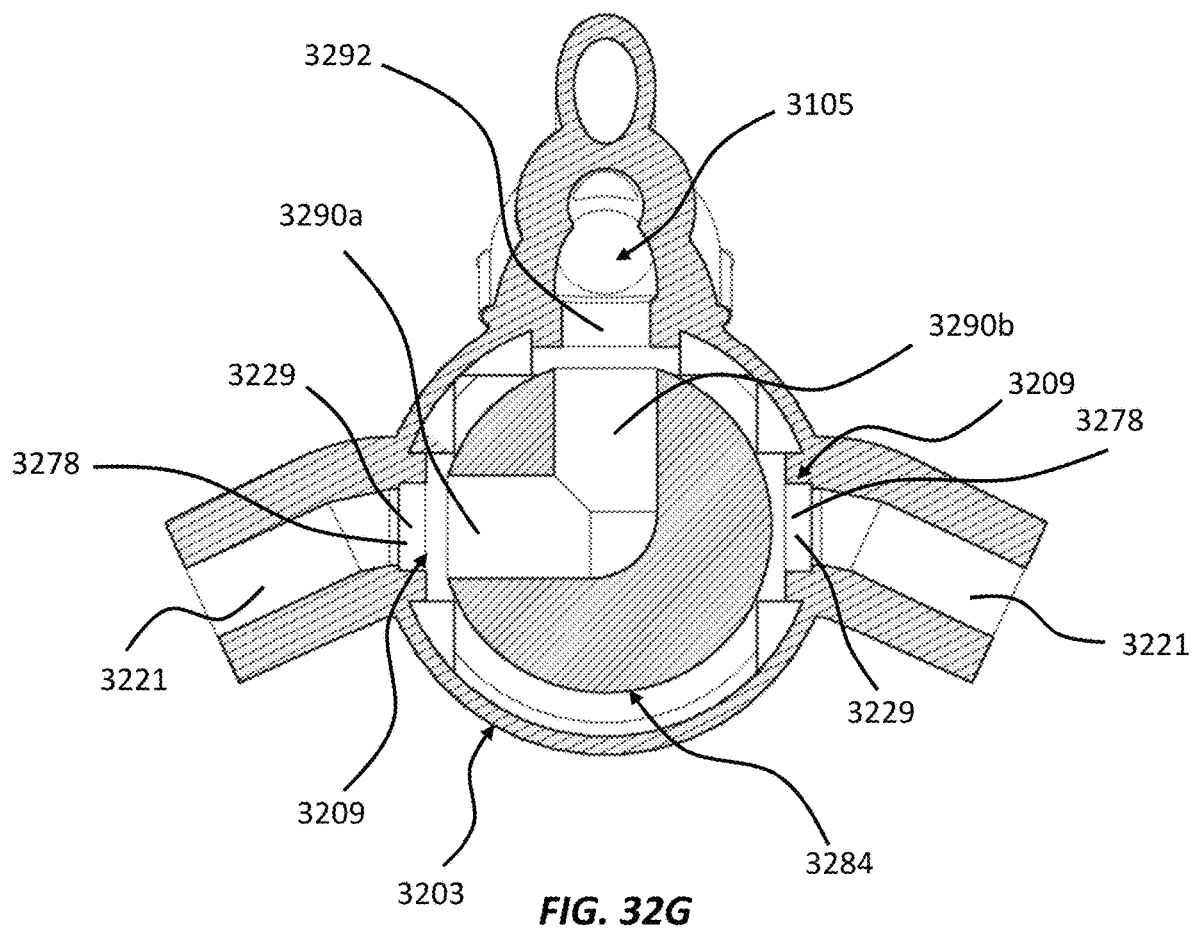
FIG. 32G is a cutaway plan view of the attachment device of FIG. 32A in a first position.
Figure 32H:
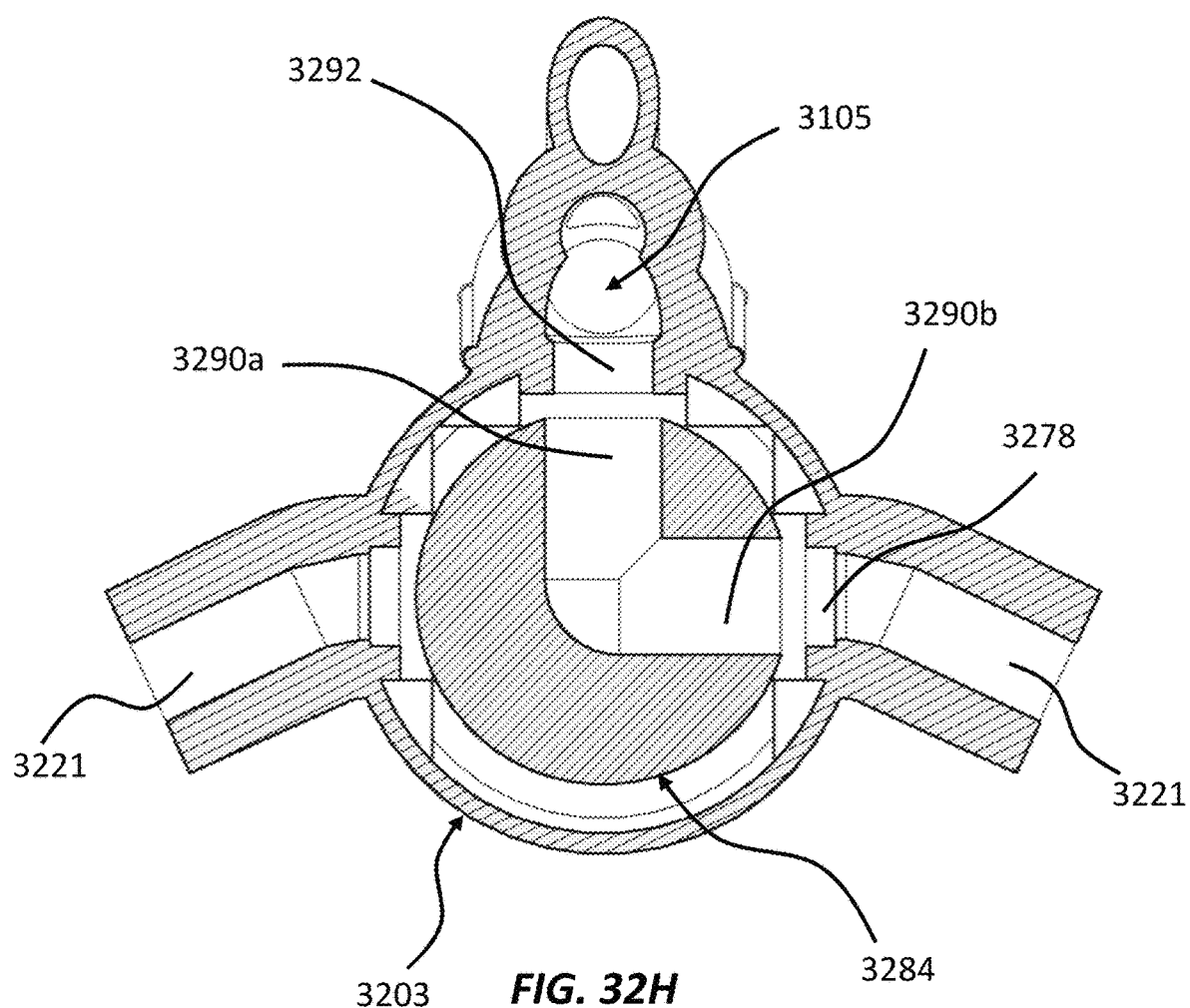
FIG. 32H is a cutaway plan view of the attachment device of FIG. 32A in a second position.

As best seen in FIGS. 32C, 32G, and 32H, there is shown that each fluid inlet port 3207 comprises an attachment device mechanism 3209 for selectively starting and stopping the flow of fluid from the respective fluid source (not shown) to the fluid outlet port 3205. In this embodiment, the attachment device mechanism 3209 comprises a valve 3229 comprising the fluid access port 3278 and the obstructor (constituted in this embodiment by the rotatable ball 3284), which valve 3239 is moveable between an open valve position (shown in later figures) and a closed valve position (shown in later figures). In this embodiment, the valve 3239 is moveable between the open valve position and the closed valve position by rotation of the obstructor 3284 relative to the fluid access port 3278.

Referring now to FIG. 32D, there is shown an upper perspective front cutaway view of the attachment device 3201 of FIG. 32A. Here, it can be seen that the body 3203 holds the obstructor/rotatable ball 3284 inside. The rotatable ball 3284 can be rotated in one plane by use of the rotatable handle 3282. As best seen in FIGS. 32E and 32F, the rotatable ball 3284 is spherical and comprises an L-shaped fluid passage 3290 therethrough. The L-shaped fluid passage comprises a first end 3290a located on the surface of the rotatable ball 3284, and a second end 3290b located on the surface of the rotatable ball 3284 at an angle of 90 degrees from the position of the first end 3290b. The rotatable ball 3284 also comprises a hexagonal recess for housing a shaft (not shown) that connects the handle 3282 to the rotatable ball 3284.

Turning now to the operation of the attachment device 3201, this is best seen in FIGS. 32G and 32H, which show a cutaway plan view of the attachment device 3201 of FIG. 32A in a first position and a second position, respectively.

FIG. 32G shows the attachment device 3201 in the first position. In the first position, the obstructor (constituted in this embodiment by the rotatable ball 3284) sits inside the body 3203 and has been rotated such that the left hand side fluid access port 3278 is aligned with the first end 3290a of the L-shaped fluid passage 3290 belonging to the rotatable ball 3284. The end position of the rotatable ball 3284 is governed by the two rotational limiters 3223*a* and 3223*b* located on the top of the body 3203 (best seen in FIG. 32C) and restrict the movement of the handle 3282 to a rotation of 90 degree between a first position and second position. In the first position, there is shown both the left hand side and right hand side attachment device mechanisms 3209 for selectively starting and stopping the flow of fluid from the respective fluid source (not shown) to the fluid outlet port 3205. In this embodiment, the left hand side attachment device mechanism 3209 comprises a valve 3229 comprising the obstructor (constituted in this embodiment by the rotatable ball 3284) and the fluid access port 3278, and shows the valve 3229 of the left hand side attachment device mechanism 3209 in the open position because the first end 3290*a* of the L-shaped fluid passage 3290 is aligned with the fluid access port 3278 thereby forming a passage for fluid to flow from a left hand side fluid source (not shown) via access hole 3221, through the left hand side fluid access port 3278, through a fluid exit passage 3292 aligned with the second end 3290*b* of the L-shaped fluid passage 3290, and out of the fluid outlet port 3205. In the first position, the right hand side attachment device mechanism 3209 valve 3229 is closed because the second end 3290*b* of the L-shaped fluid passage 3290 is not aligned with the fluid access port 3278, and due to the L-shaped fluid passage 3290 only fluid from the left hand side fluid source (not shown) is able to reach the fluid outlet port 3205 in the first position. In this way, the supply of fluid constitutes a ratio of 100%:0% because the attachment device 3201 is providing the fluid from the first fluid source (100% of first fluid supply and 0% of second fluid supply).

FIG. 32H shows the attachment device 3201 in the second position. In the second position, the obstructor (constituted in this embodiment by the rotatable ball 3284) sits inside the body 3203 and has been rotated clockwise by 90 degrees compared with the view of FIG. 32G.

The 90 degree turn is governed by the two rotational limiters 3223*a* and 3223*b*, as discussed above. In the third position, there is shown both the left hand side and right hand side attachment device mechanisms 3209 for selectively starting and stopping the flow of fluid from the respective fluid source (not shown) to the fluid outlet port 3205. In this embodiment, the right side attachment device mechanism 3209 comprises a valve 3229 comprising the obstructor (constituted in this embodiment by the rotatable ball 3284) and the fluid access port 3278, and shows the valve 3229 of the right hand side attachment device mechanism 3209 in the open position because the second end 3290*b* of the L-shaped fluid passage 3290 is aligned with the fluid access port 3278 thereby forming a passage for fluid to flow from a right hand side fluid source (not shown) via access hole 3221, through the right hand side fluid access port 3278, through a fluid exit passage 3292 aligned with the first end 3290*a* of the L-shaped fluid passage 3290, and out of the fluid outlet port 3205. In the second position, the left hand side attachment device mechanism 3209 valve 3229 is closed because the first end 3290*a* of the L-shaped fluid passage 3290 is not aligned with the fluid access port 3278, and due to the L-shaped fluid passage 3290 only fluid from the right hand side fluid source (not shown) is able to reach the fluid outlet port 3205 in the second position. In this way, the supply of fluid constitutes a ratio of 0%:100% because the attachment device 3201 is providing the fluid from the second fluid source (0% of first fluid supply and 100% of second fluid supply).

FIGS. 32G and 32H demonstrate how the attachment device can be used to transfer/switch supply of fluid from a first fluid source to supply from a second fluid source without compromising the fluid flow and/or fluid pressure.

Figure 33:
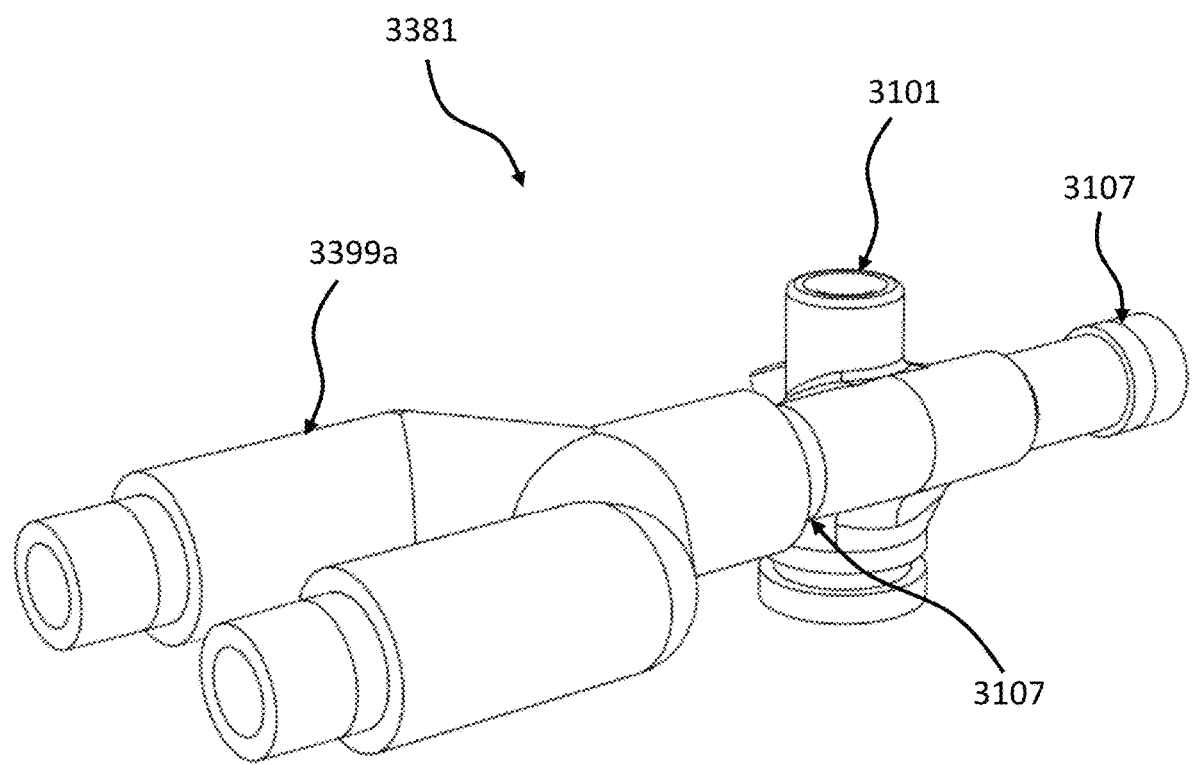
FIG. 33 is upper perspective rear view of an assembly comprising the attachment device of FIGS. 31A-31I connected to a wye connector.

Referring now to FIG. 33, there is shown a perspective view of an assembly generally indicated 3381 formed according to an embodiment of the invention. The assembly 3381 comprising the attachment device 3101 of FIGS. 31A-31I, and a wye connector 3399*a* (connected to a ventilator, for example—which may thereby constitute the fluid source, for instance). In this embodiment, the wye connector 3399*a* is connected to the left hand side positive pressure fluid inlet port 3107 of the attachment device 3101. The assembly is thus shown in the first position of the attachment device 3101, as that displayed and demonstrated in FIG. 31G. It will be understood that a further wye connector, for example, may be attached to the right hand side positive pressure fluid inlet port 3107 to realize the second and third positions of the attachment device 3101, as those displayed and demonstrated in FIGS. 31H and 31I. In this way, the wye connector 3399*a* and attachment device mechanism 3109 are able to interconnect for enhanced performance.

Figure 34:
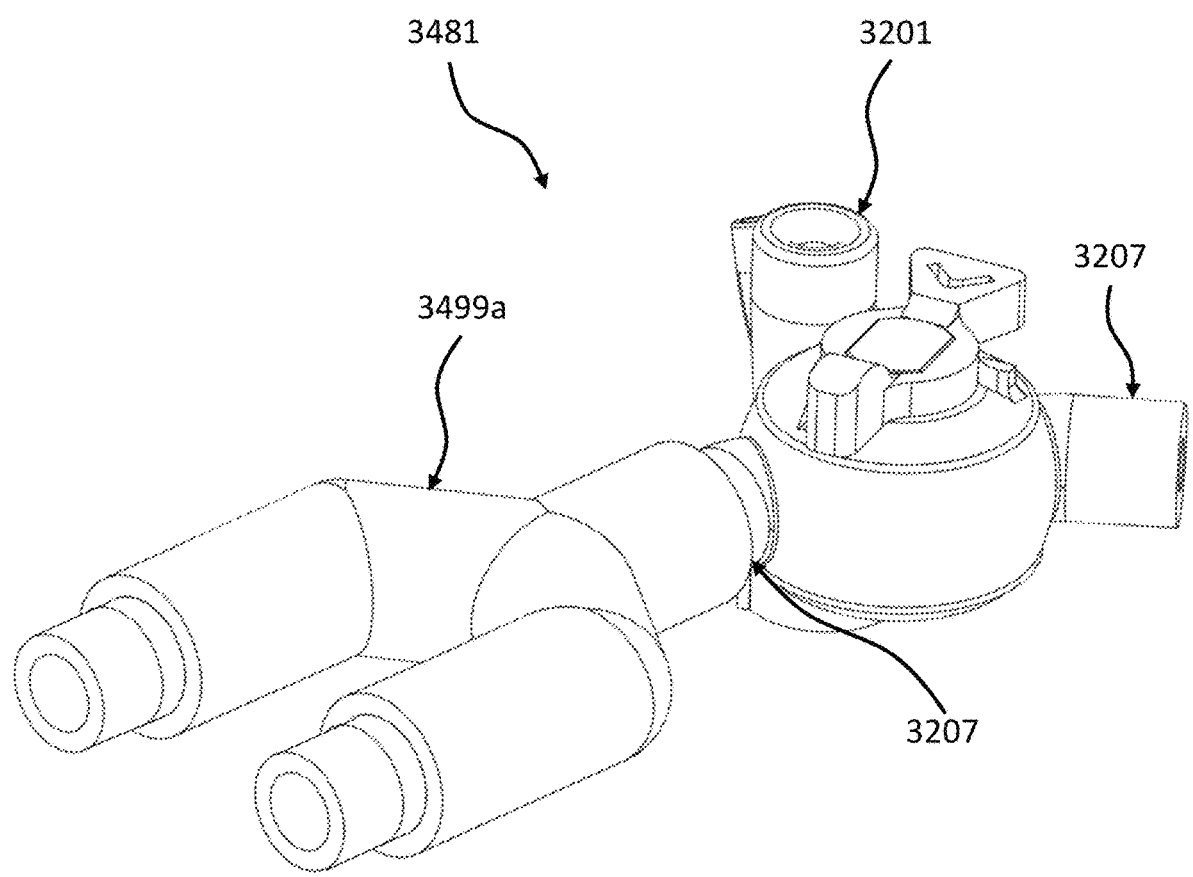
FIG. 34 is upper perspective front view of an assembly comprising the attachment device of FIGS. 32A-32H connected to a wye connector.

Referring now to FIG. 34, there is shown a perspective view of an assembly generally indicated 3481 formed according to an embodiment of the invention. The assembly 3481 comprising the attachment device 3201 of FIGS. 32A-31G, and a wye connector 3499*a* (connected to a ventilator, for example—which may thereby constitute the fluid source, for instance). In this embodiment, the wye connector 3499*a* is connected to the left hand side positive pressure fluid inlet port 3207 of the attachment device 3201. The assembly is thus shown in the first position of the attachment device 3201, as that displayed and demonstrated in FIG. 32G. It will be understood that a further wye connector, for example, may be attached to the right hand side positive pressure fluid inlet port 3207 to realize the second position of the attachment device 3201, as that displayed and demonstrated in FIG. 32H. In this way, the wye connector 3499*a* and attachment device mechanism 3209 are able to interconnect for enhanced performance.

Figure 35:
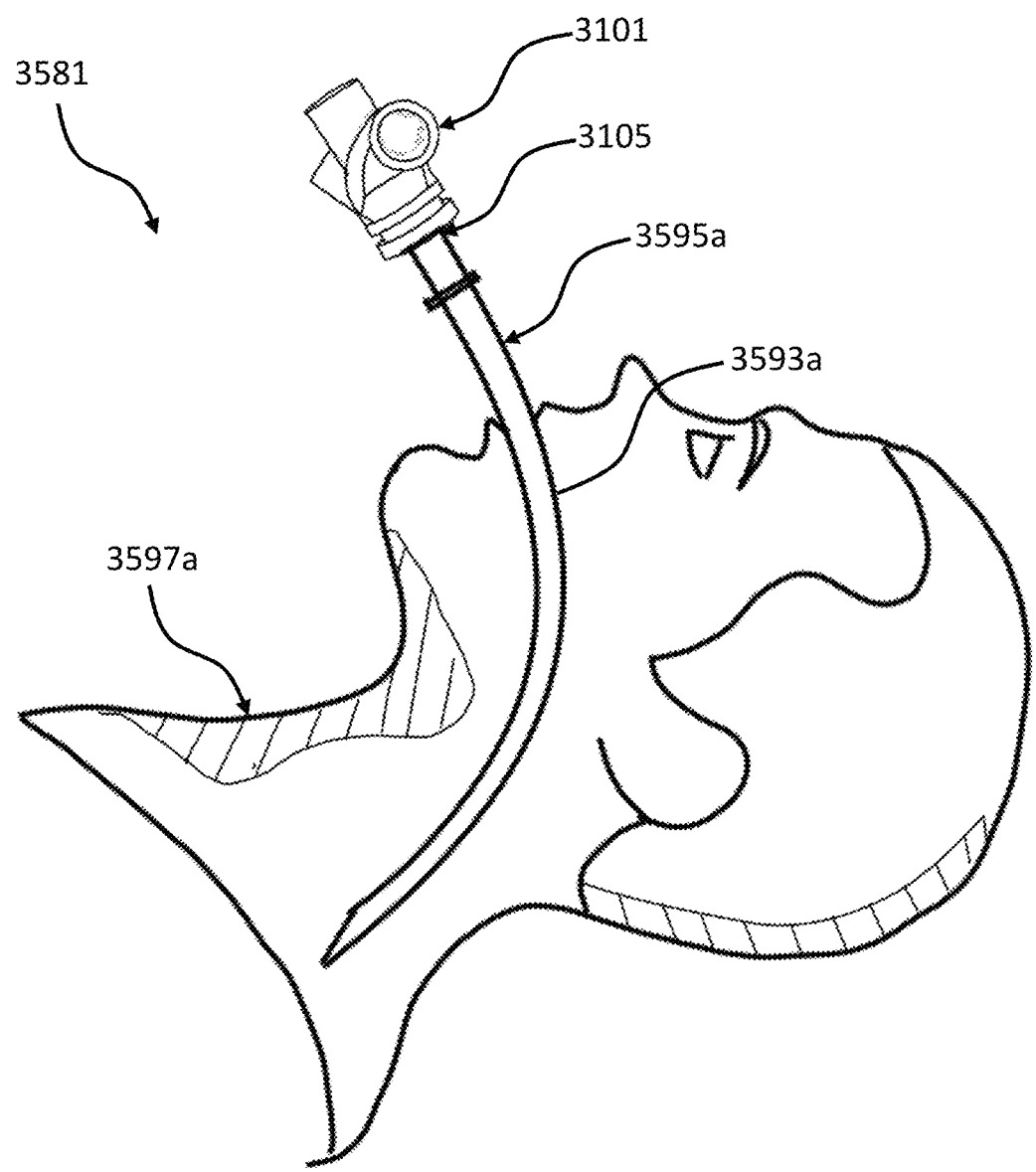
FIG. 35 is a schematic side view of an assembly comprising the attachment device of FIGS. 31A-31I connected to an endotracheal tube, in-situ.

Referring now to FIG. 35, there is shown a schematic side view of an assembly generally indicated 3581 comprising the attachment device 3101 of FIGS. 31A-31I connected to an endotracheal tube 3595*a*. In this embodiment, the endotracheal tube 3595*a* is shown, in-situ, inserted down the trachea 3593*a* of a human patient 3597*a* providing intubation thereto to maintain an open airway and to facilitate ventilation of the lungs of the patient 3597*a*, for example. In this embodiment, the fluid outlet port 3105 (of the attachment device 3101) is connected to the endotracheal tube 3595*a*. It will be understood that any suitable attachment device can be connected to the endotracheal tube 3595*a* in this manner; for instance, the attachment device 3201 of FIGS. 32A-31G can be connected to the endotracheal tube 3595*a* in this manner. It will be understood that the attachment device may also be utilized with animals, and a similar procedure involving an assembly comprising an attachment device and an endotracheal tube may be employed by a healthcare professional for an animal.

CLAUSES

It will be understood that the following clauses form part of the specification and disclosure of the invention defined herein. More particularly, the invention herein may be defined by the combination of the features of the clauses as detailed below, and such clauses may be utilized to amend the combination of the features within the claims of this application.

1. An attachment device for maintaining positive fluid pressure, the attachment device comprising a body having a fluid outlet port and at least two positive pressure fluid inlet ports;
   wherein each of the at least two positive pressure fluid inlet ports is connectable to a respective fluid source;
   wherein each of the at least two positive pressure fluid inlet ports is in fluid communication with the fluid outlet port;
   wherein each of the at least two positive pressure fluid inlet ports comprises an attachment device mechanism for selectively starting and stopping a flow of fluid from the respective fluid source to the fluid outlet port, and
   wherein the attachment device mechanism comprises a valve moveable between an open valve position and a closed valve position.

2. The attachment device of Clause 1, wherein the at least two positive pressure fluid inlet ports comprise a first positive pressure fluid inlet port having a first attachment device mechanism, and a second positive pressure fluid inlet port having a second attachment device mechanism,
   wherein the first attachment device mechanism actuates the flow of fluid from a first fluid source to the fluid outlet port, and the second attachment device mechanism actuates the flow of fluid from a second fluid source to the fluid outlet port, and
   wherein the ratio of the flow of fluid from the first fluid source to the fluid outlet port and the flow of fluid from the second fluid source to the fluid outlet port ranges from 100%:0% to 0%/100%.

3. The attachment device of Clause 1, wherein the ratio of the flow of fluid from the first fluid source to the fluid outlet port and the flow of fluid from the second fluid source to the fluid outlet port is at least one selected from: 90%:10%, 80%:20%, 70%:30%, 60%:40%, 50%:50%, 40%:60%, 30%:70%, 20%:80%, and 10%:90%.

4. The attachment device of any of Clauses 1 to 3, wherein the valve comprises a fluid access port.

5. The attachment device of any of Clauses 1 to 4, wherein the valve comprises an obstructor.

6. The attachment device of Clause 5, wherein the obstructor and the fluid access port are rotatably engaged.

7. The attachment device of Clause 5 or Clause 6, wherein the valve is moveable between the open valve position and the closed valve position by rotation of the obstructor relative to the fluid access port.

8. The attachment device of Clause 7, wherein the valve is moveable between the open valve position and the closed valve position by a rotation of approximately 90 degrees of the obstructor relative to the fluid access port.

9. The attachment device of any of Clauses 5 to 8, wherein the obstructor comprises a rotatable ball having a fluid passage therethrough.

10. The attachment device of Clause 9, wherein the fluid passage is L-shaped.

11. The attachment device of any of Clauses 5 to 10, wherein the obstructor comprises a rotatable handle.

12. The attachment device of Clause 5, wherein the obstructor and the fluid access port are linearly engaged.

13. The attachment device of Clause 5 or Clause 12, wherein the valve is moveable between the open valve position and the closed valve position by a linear movement of the obstructor relative to the fluid access port.

14. The attachment device of Clause 13, wherein the obstructor comprises a hollow tube having at least one fluid passage therethrough.

15. The attachment device of Clause 14, wherein the obstructor comprises a hollow tube having a first fluid passage and second fluid passage separated by a partition.

16. The attachment device of Clause 15, wherein the first fluid passage is alignable with the fluid access port towards or at the open valve position by a linear movement of the obstructor relative to the fluid access port.

17. The attachment device of Clause 15, wherein the second fluid passage is alignable with the fluid access port towards or at the open valve position by a linear movement of the obstructor relative to the fluid access port.

18. The attachment device of any of Clauses 12 to 17, comprising an obstructor holder connected to the body, and said obstructor holder comprising the fluid access port.

19. The attachment device of Clause 18, wherein the obstructor holder is slidably engaged with the obstructor.

20. The attachment device of any of Clauses 14 to 19, wherein the obstructor holder comprises at least two anti-rotation internal protrusions.

21. The attachment device of any of Clauses 14 to 20, wherein the obstructor comprises at least two anti-rotation external recesses.

22. The attachment device of any of Clauses 1 to 21, comprising a bronchoscope port in fluid communication with the fluid outlet port.

23. The attachment device of any of Clauses 1 to 22, comprising a suction catheter port in fluid communication with the fluid outlet port.

24. The attachment device of Clause 23, wherein the bronchoscope port is in fluid communication with the suction catheter port.

25. The attachment device of any of Clauses 1 to 24, wherein each of the at least two positive pressure fluid inlet ports comprises an arm, said arm extending from the body.

26. The attachment device of any of Clauses 1 to 25, wherein the body comprises internal threading at the fluid outlet port that is connectable to a pressure regulator having external threading.

27. The attachment device of any of Clauses 1 to 25, wherein the body comprises external threading at the fluid outlet port that is connectable to a pressure regulator having internal threading.

28. The attachment device of any of Clauses 1 to 25, wherein the body comprises a push-fit mechanism.

29. The attachment device of any of Clauses 1 to 28, wherein at least one of the at least two positive pressure fluid inlet ports is detachably attached to the body.

30. The attachment device of any of Clauses 1 to 29, wherein the fluid outlet port is connectable to an endotracheal tube.

31. The attachment device of any of Clauses 1 to 30, wherein at least one of the at least two positive pressure fluid inlet ports is connectable to a ventilator or ventilator tube.

32. The attachment device of any of Clauses 1 to 31 for use in a medical application.

33. The attachment device of any of Clauses 1 to 31 for use in at least one of spooling up a turbocharger, changing cam timing in an engine, operating as an injector or a valve, generating downforce in a car chassis, dispersion of carbon dioxide, controlling humidity by atomizing water, pressure positive transport ventilation, switching fluids from the respective fluid sources in transport ventilation, enabling an uninterrupted flow of the fluid in transport ventilation, and nutrient distribution.

34. An assembly comprising an attachment device, and a connector for connecting at least one fluid source to the attachment device;
  wherein the attachment device comprising a body having a fluid outlet port and at least two positive pressure fluid inlet ports;
    wherein each of the at least two positive pressure fluid inlet ports is connectable to a respective fluid source;
    wherein each of the at least two positive pressure fluid inlet ports is in fluid communication with the fluid outlet port;
    wherein each of the at least two positive pressure fluid inlet ports comprises an attachment device mechanism for selectively starting and stopping a flow of fluid from the respective fluid source to the fluid outlet port; and
    wherein the attachment device mechanism comprises a valve moveable between an open valve position and a closed valve position; and
  wherein the connector being attachable to the at least one fluid source and the attachment device, the connecter connector comprising a housing and a connector mechanism for selectively starting and stopping the flow of fluid from the at least one fluid source to the attachment device.

35. The assembly of Clause 34, further comprising a pressure regulator for regulating fluid pressure and fluid flow speed from the fluid outlet port.

36. The assembly of Clause 35, wherein the pressure regulator comprises external threading that is connectable to internal threading of the fluid outlet port.

37. The assembly of Clause 35, wherein the pressure regulator comprises internal threading that is connectable to external threading of the fluid outlet port.

38. The assembly of any of Clauses 35 to 37, wherein the pressure regulator comprises:
  a housing formed to include a bore therein;
  a piston moveably disposed within said bore, wherein said piston comprises an annular lip adjacent a first end thereof;
  a pressure regulator spring disposed within said bore, and comprising a first end and a second end; and
  an adjustment cap moveably disposed in said bore, wherein said adjustment cap is formed to include a plurality of key slots formed therein;
  wherein:
  said first end of said pressure regulator spring is in physical contact with said annular lip; and
  said second end of said pressure regulator spring is in physical contact with said adjustment cap wherein:
  rotating said adjustment cap in a first direction causes said adjustment cap to compress said pressure regulator spring;
  rotating said adjustment cap in a second and opposite direction causes said adjustment cap to decompress said pressure regulator spring;
  rotating said adjustment cap in said first direction increases the output pressure of the pressure regulator;
  rotating said adjustment cap in said second direction decreases the output pressure of the pressure regulator;
  said bore is defined by a cylindrical wall;
  said cylindrical wall is formed to include a first threading therein;
  said adjustment cap is formed to include a second threading formed on a periphery thereof; and
  said second threading is configured to mesh with said first threading.

39. The assembly of any of Clauses 34 to 38, further comprising a ventilator or ventilator connection tube connectable to the airway of a living patient.

40. The assembly of Clause 39, wherein the ventilator being connectable to the pressure regulator, the ventilator comprising:
  a venturi, comprising a throat;
  a venturi nozzle;
  a venturi opening in the venturi nozzle through which pressure-controlled oxygen flows outward, wherein said venturi opening opens to said throat, and wherein said venturi opening and said throat are substantially longitudinally aligned;
  an ambient air aperture in fluid communication with said venturi nozzle and with ambient air;
  a fluid port in fluid communication with the airway of the patient;
  a pressure force multiplier in fluid communication with said fluid port, wherein said pressure force multiplier includes at least one opening defined therethrough; said pressure force multiplier comprising at least one flap movable between an open position and a closed position relative to said at least one opening; and
  a valve moveable along an axis of movement relative to said venturi opening in said venturi nozzle between a start flow position that causes entrainment of the ambient air by the flow of pressure-controlled oxygen within said throat, and a stop flow position that ceases entrainment of the ambient air by the flow of pressure-controlled oxygen within said throat;
  wherein said pressure force multiplier is configured wherein exhalation of the patient into said fluid port actuates said valve along said axis of movement relative to said venturi nozzle to close said venturi nozzle;
  wherein said pressure force multiplier is configured wherein inhalation of the patient through said fluid port actuates said valve along said axis of movement relative to said venturi nozzle; and
  wherein said axis of movement of said valve is substantially longitudinally aligned with a longitudinal direction of said throat.

41. The assembly of any of Clauses 34 to 38, further comprising an apparatus suitable for use with a respirator.

42. The assembly of Clause 41, wherein the apparatus is connectable to the pressure regulator and comprising:
  a venturi, comprising:
    a throat,
    a venturi nozzle, and;
    a venturi opening in the venturi nozzle through which pressure-controlled fluid flows outward, wherein said venturi opening opens to said throat, and wherein said venturi opening and said throat are substantially longitudinally aligned;
  an ambient fluid aperture in fluid communication with said venturi nozzle and with an ambient fluid;
  a fluid port;
  a pressure force multiplier in fluid communication with said fluid port; and
  a valve moveable along an axis of movement relative to said venturi opening in said venturi nozzle between a start flow position that causes entrainment of the ambient fluid by the flow of pressure-controlled fluid within said throat, and a stop flow position that ceases entrainment of the ambient fluid by the flow of pressure-controlled fluid within said throat;
  wherein said pressure force multiplier is configured such that fluid forced into said fluid port actuates said valve along said axis of movement relative to said venturi nozzle to close said venturi nozzle;

wherein said pressure force multiplier is configured such that fluid withdrawn from said fluid port actuates said valve along said axis of movement relative to said venturi nozzle;

wherein said axis of movement of said valve is substantially longitudinally aligned with a longitudinal direction of said throat; and wherein said pressure force multiplier is positioned between said venturi nozzle and said fluid port.

43. The assembly of Clause 35, further comprising an oxygen-filled reservoir.

44. The assembly of Clause 43, wherein the oxygen-filled reservoir is connected to the ventilator.

45. The assembly of Clause 44, wherein the ventilator comprises a one-way exhaust valve and a one-way reservoir valve, and wherein the one-way reservoir valve fluidly connects the oxygen-filled reservoir to the ventilator.

46. The assembly of Clause 34, wherein the attachment device mechanism and the connector mechanism are interconnected for selectively starting and stopping the flow of fluid from the fluid source to the attachment device.

47. The assembly of Clause 34, further comprising an endotracheal tube that is connected to the fluid outlet port.

48. The assembly of Clause 34, further comprising a ventilator or ventilator connection tube that is connected to at least one of the at least two positive pressure fluid inlet ports.

49. A method of switching one fluid source with another fluid source and maintaining continuous positive pressure fluid flow to a respirator or ventilator, comprising the steps of:

providing the respirator or the ventilator;
providing the one fluid source;
attaching said one fluid source to one connector, said one connector comprising one housing and one connector mechanism for selectively starting and stopping a flow of fluid;
providing an attachment device comprising a body having a fluid outlet port and at least two positive pressure fluid inlet ports;
wherein each of the at least two positive pressure fluid inlet ports is connectable to a respective fluid source;
wherein each of the at least two positive pressure fluid inlet ports is in fluid communication with the fluid outlet port;
wherein each of the at least two positive pressure fluid inlet ports comprises an attachment device mechanism for selectively starting and stopping the flow of fluid; and
wherein the attachment device mechanism comprises a valve moveable between an open valve position and a closed valve position;
providing a pressure regulator for regulating fluid pressure and fluid flow speed;
connecting the fluid outlet port of the attachment device to the pressure regulator;
connecting the pressure regulator to the respirator or the ventilator;
connecting said one connector to one fluid inlet port of the attachment device;
selectively starting the flow of fluid from said one fluid source to the respirator or the ventilator using said one connector mechanism and said one attachment device mechanism;
providing another fluid source;
attaching said another fluid source to another connector, said another connector comprising another housing and another connector mechanism for selectively starting and stopping the flow of fluid;
connecting said another connector to another fluid inlet port of the attachment device;
selectively starting the flow of fluid from said another fluid source to the respirator or the ventilator using said another connector mechanism and another attachment device mechanism;
selectively stopping the flow of fluid from said one fluid source to the respirator or the ventilator using said one connector mechanism and said one attachment device mechanism; and
disconnecting said one connector from said one fluid inlet port of the attachment device.

50. The method of Clause 49, wherein the step of providing the pressure regulator for regulating fluid pressure and fluid flow speed comprises providing the pressure regulator that comprises:

a housing formed to include a bore therein;
a piston moveably disposed within said bore, wherein said piston comprises an annular lip adjacent a first end thereof;
a pressure regulator spring disposed within said bore, and comprising a first end and a second end; and
an adjustment cap moveably disposed in said bore, wherein said adjustment cap is formed to include a plurality of key slots formed therein;
wherein:
said first end of said pressure regulator spring is in physical contact with said annular lip; and
said second end of said pressure regulator spring is in physical contact with said adjustment cap wherein:
rotating said adjustment cap in a first direction causes said adjustment cap to compress said pressure regulator spring;
rotating said adjustment cap in a second and opposite direction causes said adjustment cap to decompress said pressure regulator spring;
rotating said adjustment cap in said first direction increases the output pressure of the pressure regulator;
rotating said adjustment cap in said second direction decreases the output pressure of the pressure regulator;
said bore is defined by a cylindrical wall;
said cylindrical wall is formed to include a first threading therein;
said adjustment cap is formed to include a second threading formed on a periphery thereof; and
said second threading is configured to mesh with said first threading.

51. The method of Clause 49, wherein the step of providing the ventilator comprises providing the ventilator that is connectable to the airway of a living patient, the ventilator comprising:

a venturi, comprising a throat;
a venturi nozzle;
a venturi opening in the venturi nozzle through which pressure-controlled oxygen flows outward, wherein said venturi opening opens to said throat, and wherein said venturi opening and said throat are substantially longitudinally aligned;
an ambient air aperture in fluid communication with said venturi nozzle and with ambient air;
a fluid port in fluid communication with the airway of the patient;

a pressure force multiplier in fluid communication with said fluid port, wherein said pressure force multiplier includes at least one opening defined therethrough; said pressure force multiplier comprising at least one flap movable between an open position and a closed position relative to said at least one opening; and a valve moveable along an axis of movement relative to said venturi opening in said venturi nozzle between a start flow position that causes entrainment of the ambient air by the flow of pressure-controlled oxygen within said throat, and a stop flow position that ceases entrainment of the ambient air by the flow of pressure-controlled oxygen within said throat; wherein said pressure force multiplier is configured wherein exhalation of the patient into said fluid port actuates said valve along said axis of movement relative to said venturi nozzle to close said venturi nozzle;

wherein said pressure force multiplier is configured wherein inhalation of the patient through said fluid port actuates said valve along said axis of movement relative to said venturi nozzle; and wherein said axis of movement of said valve is substantially longitudinally aligned with a longitudinal direction of said throat.

As used in this document, both in the description and in the claims, and as customarily used in the art, the words "substantially," "approximately," and similar terms of approximation are used to account for manufacturing tolerances, manufacturing variations, and manufacturing imprecisions that are inescapable parts of fabricating any mechanism or structure in the physical world.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. The purpose of the Abstract of this document is to enable the U.S. Patent and Trademark Office, as well as readers who are not familiar with patent or legal terms or phraseology, to determine quickly from a cursory inspection the nature and essence of the technical disclosure of the application. The Abstract is not intended to define the invention, nor is it intended to limit to the scope of the invention. The purpose of the clauses of this document is to provide support for claims in any later-file foreign patent applications claiming priority to this document. The clauses are not intended to define the invention, nor are they intended to limit to the scope of the invention. Therefore, the invention is not to be restricted or limited except in accordance with the following claims and their legal equivalents.

What is claimed is:

1. A medical attachment device for maintaining positive fluid pressure in a patient, the attachment device comprising a body having a fluid outlet port, at least two positive pressure fluid inlet ports, and an obstructor holder comprising a fluid access port in fluid communication with the fluid outlet port;

wherein each of the at least two positive pressure fluid inlet ports is connectable to a respective first fluid source;

wherein each of the at least two positive pressure fluid inlet ports is in fluid communication with the fluid outlet port via the fluid access port;

wherein each of the at least two positive pressure fluid inlet ports comprises an attachment device mechanism for selectively starting and stopping a flow of fluid from the respective fluid source to the fluid outlet port;

wherein the attachment device mechanism is housed at least partially in the obstructor holder and comprises:
an arm having a first end in fluid communication with a respective one of the at least two positive pressure fluid inlet ports and a second end;
an obstructor in the first end configured to seal the fluid access port in the obstructor holder; and
a circular aperture in the second end to enable, by motion of the arm, selective fluid communication between the respective fluid inlet port and the fluid outlet port via the fluid access port.

2. The medical attachment device of claim 1, wherein the at least two positive pressure fluid inlet ports comprise a first positive pressure fluid inlet port having a first attachment device mechanism, and a second positive pressure fluid inlet port having a second attachment device mechanism, wherein the first attachment device mechanism actuates the flow of fluid from the first fluid source to the fluid outlet port, and the second attachment device mechanism actuates the flow of fluid from the second fluid source to the fluid outlet port, and wherein the ratio of the flow of fluid from the first fluid source to the fluid outlet port and the flow of fluid from the second fluid source to the fluid outlet port ranges from 100%:0% to 0%/100%.

3. The medical attachment device of claim 2, wherein the ratio of the flow of fluid from the first fluid source to the fluid outlet port and the flow of fluid from the second fluid source to the fluid outlet port is at least one selected from: 90%:10%, 80%:20%, 70%:30%, 60%:40%, 50%:50%, 40%:60%, 30%:70%, 20%:80%, and 10%:90%.

4. The medical attachment device of claim 1, wherein the the arm and the fluid access port are linearly engaged.

5. The medical attachment device of claim 1, wherein the attachment device mechanism is moveable between an open valve position and a closed valve position by a linear movement of the arm relative to the fluid access port.

6. The medical attachment device of claim 5, wherein the arm comprises a hollow tube having at least one fluid passage therethrough.

7. The medical attachment device of claim 6, wherein the hollow tube has a partition.

8. The medical attachment device of claim 7, wherein the hollow tube is alignable with the fluid access port towards or at the open valve position by a linear movement of the arm relative to the fluid access port.

9. The medical attachment device of claim 1, wherein the obstructor holder comprises at least two anti-rotation internal protrusions.

10. The medical attachment device of claim 9, wherein the arm comprises at least two anti-rotation external recesses.

11. The medical attachment device of claim 1, comprising a bronchoscope port in fluid communication with the fluid outlet port.

12. The medical attachment device of claim 1, comprising a suction catheter port in fluid communication with the fluid outlet port.

13. The medical attachment device of claim 11, wherein the bronchoscope port is in fluid communication with a suction catheter port.

14. The medical attachment device of claim 1, wherein the fluid outlet port is connectable to an endotracheal tube in situ.

15. The medical attachment device of claim 1, wherein at least one of the at least two positive pressure fluid inlet ports is connectable to a ventilator or ventilator tube.

16. The medical attachment device of claim 1 for use in a medical application.

17. An assembly comprising a medical attachment device, and a connector for connecting at least one fluid source to the attachment device;
 wherein the attachment device comprising a body having a fluid outlet port, at least two positive pressure fluid inlet ports, and an obstructor holder comprising a fluid access port in fluid communication with the fluid outlet port;
 wherein each of the at least two positive pressure fluid inlet ports is connectable to a respective fluid source;
 wherein each of the at least two positive pressure fluid inlet ports is in fluid communication with the fluid outlet port;
 wherein each of the at least two positive pressure fluid inlet ports comprises an attachment device mechanism for selectively starting and stopping a flow of fluid from the respective fluid source to the fluid outlet port; and
 wherein the attachment device mechanism is housed at least partially in the obstructor holder and comprises:
  an arm having a first end in fluid communication with a respective one of the at least two positive pressure fluid inlet ports and a second end;
  an obstructor in the first end configured to seal the fluid access port in the obstructor holder; and
  a circular aperture in the second end to enable, by motion of the arm, selective fluid communication between the respective fluid inlet port and the fluid outlet port via the fluid access port.

18. The assembly of claim 17, further comprising an endotracheal tube in-situ that is connected to the fluid outlet port.

19. A method of switching one fluid source with another fluid source and maintaining continuous positive pressure fluid flow to a respirator or ventilator, comprising the steps of:
 providing the respirator or the ventilator;
 providing the one fluid source;
 attaching said one fluid source to one connector, said one connector comprising one housing and one connector mechanism for selectively starting and stopping a flow of fluid;
 providing an attachment device comprising a body having a fluid outlet port and at least two positive pressure fluid inlet ports;
 wherein each of the at least two positive pressure fluid inlet ports is connectable to a respective fluid source;
 wherein each of the at least two positive pressure fluid inlet ports is in fluid communication with the fluid outlet port;
 wherein each of the at least two positive pressure fluid inlet ports comprises an attachment device mechanism for selectively starting and stopping the flow of fluid; and
 wherein the attachment device mechanism comprises a valve moveable between an open valve position and a closed valve position;
 providing a pressure regulator for regulating fluid pressure and fluid flow speed;
 connecting the fluid outlet port of the attachment device to the pressure regulator;
 connecting the pressure regulator to the respirator or the ventilator;
 connecting said one connector to one fluid inlet port of the attachment device;
 selectively starting the flow of fluid from said one fluid source to the respirator or the ventilator using said one connector mechanism and said one attachment device mechanism;
 providing another fluid source;
 attaching said another fluid source to another connector, said another connector comprising another housing and another connector mechanism for selectively starting and stopping the flow of fluid;
 connecting said another connector to another fluid inlet port of the attachment device;
 selectively starting the flow of fluid from said another fluid source to the respirator or the ventilator using said another connector mechanism and another attachment device mechanism;
 selectively stopping the flow of fluid from said one fluid source to the respirator or the ventilator using said one connector mechanism and said one attachment device mechanism; and
 disconnecting said one connector from said one fluid inlet port of the attachment device.

20. A medical attachment device for maintaining positive fluid pressure in a patient, the attachment device comprising a body having a fluid outlet port, at least one positive pressure fluid inlet port, and an obstructor holder comprising a fluid access port in fluid communication with the fluid outlet port;
 wherein the at least one positive pressure fluid inlet port is connectable to a first fluid source;
 wherein the at least one positive pressure fluid inlet port is in fluid communication with the fluid outlet port via the fluid access port;
 wherein the at least one positive pressure fluid inlet port comprises an attachment device mechanism for selectively starting and stopping a flow of fluid from the respective fluid source to the fluid outlet port;
 wherein the attachment device mechanism is housed at least partially in the obstructor holder and comprises:
  an arm having a first end in fluid communication with the at least one positive pressure fluid inlet port and a second end;
  an obstructor in the first end configured to seal the fluid access port in the obstructor holder; and
  a circular aperture in the second end to enable, by motion of the arm, selective fluid communication between the fluid inlet port and the fluid outlet port via the fluid access port.

* * * * *